United States Patent
Headley et al.

[11] Patent Number: 6,099,491
[45] Date of Patent: *Aug. 8, 2000

[54] FLUID SEPARATION SYSTEM

[75] Inventors: Thomas D. Headley, Wellesley, Mass.; Edward T. Powers, Hampton Falls, N.H.

[73] Assignee: Transfusion Technologies Corporation, Natick, Mass.

[*] Notice: This patent is subject to a terminal disclaimer.

[21] Appl. No.: 08/843,218

[22] Filed: Apr. 14, 1997

Related U.S. Application Data

[63] Continuation of application No. 08/322,601, Oct. 13, 1994, Pat. No. 5,733,253.

[51] Int. Cl.[7] ............. A61M 37/00; B04B 15/00; B04B 11/00; B01D 37/00
[52] U.S. Cl. .......... 604/4; 604/5; 604/6; 494/10; 494/28; 210/767; 210/782
[58] Field of Search ............ 494/10; 210/117, 210/767, 782; 604/6

[56] References Cited

U.S. PATENT DOCUMENTS

| | | | |
|---|---|---|---|
| 5,039,401 | 8/1991 | Columbus et al. | 210/117 |
| 5,387,174 | 2/1995 | Rochat | 494/10 |
| 5,733,253 | 3/1998 | Headley et al. | 604/4 |

*Primary Examiner*—John G. Weiss
*Assistant Examiner*—Miley C. Peppers, III
*Attorney, Agent, or Firm*—Bromberg & Sunstein LLP

[57] ABSTRACT

A system for separating a fluid having heavier and lighter components. The system includes a rotor having a rigid mounting member and an elastic diaphragm attached to the mounting member, the diaphragm defining a chamber. The system also includes a chuck for holding the rigid mounting member of the rotor and for spinning the rotor around an axis. The pressure of a control fluid, preferably a control gas, disposed adjacent the rotor's diaphragm is varied in order to control the volume of the rotor. Pressurizing the control gas causes fluid to flow out of the rotor; applying a vacuum to the diaphragm draws fluid into the rotor.

40 Claims, 36 Drawing Sheets

FLUID SEPARATION SYSTEM

RELATED APPLICATION

This application is a continuation of U.S. patent application Ser. No. 08/322,601, filed Oct. 13, 1994 for an invention by Headley and Powers, issued Mar. 31, 1998 as U.S. Pat. No. 5,733,253. This related application is incorporated herein by reference.

TECHNICAL FIELD

This invention generally relates to systems for processing blood and other biological fluids.

BACKGROUND ART

Centrifugal biological-fluid-processing systems have been in existence for some time. Some are used to collect high concentrations of certain components of a person's blood while others are used to further process blood components by washing, concentrating or otherwise purifying the blood component of interest. Some of these systems are used to process biological fluids other than blood. Filtration systems are also used for processing blood and other biological fluids.

The centrifugal systems (hereinafter called blood-processing systems) generally fall into two categories, continuous-flow devices and discontinuous-flow devices.

In continuous-flow systems, whole blood from the donor or patient flows through one conduit into the spinning rotor where the components are separated. The component of interest is collected and the unwanted components are returned to the donor through a second conduit on a continuous basis as more whole blood is being drawn. Because the rate of drawing and the rate of return are substantially the same, the extracorporeal volume, or the amount of blood that is out of the donor or patient at any given time in the procedure, is relatively small. These systems typically employ a belt-type rotor, which has a relatively large diameter but a relatively small (typically 100 ml or less) processing volume. Although continuous-flow systems have the advantage that the amount of blood that must be outside the donor or patient can be relatively small, they have the disadvantage that the diameter of the rotor is large. These systems are, as a consequence, large; furthermore, they are complicated to set up and use. These devices are used almost exclusively for the collection of platelets.

In discontinuous-flow systems, whole blood from the donor or patient also flows through a conduit into the rotor where component separation takes place. These systems employ a bowl-type rotor with a relatively large (typically 200 ml or more) volume that must be filled with blood before any of the desired components can be harvested. When the bowl is full, the drawing of fresh blood is stopped, and the unwanted components are returned to the donor or patient through the same conduit intermittently, in batches, rather than on a continuous basis. When the return has been completed, whole blood is again drawn from the donor or patient, and a second cycle begins. This process continues until the desired amount of component has been collected.

Discontinuous-flow systems have the advantage that the rotors are relatively small in diameter but have the disadvantage that the extracorporeal volume is large. This, in turn, makes it difficult or impossible to use discontinuous systems on people whose size and weight will not permit the drawing of the amount of blood required to fill the rotor. Discontinuous-flow devices are used for the collection of platelets and/or plasma, and for the concentration and washing of red blood cells (RBCs). They are used to reconstitute previously frozen RBCs and to salvage RBCs lost intraoperatively. Because the bowls in these systems are rigid and have a fixed volume, however, it is difficult to control the hematocrit of the final product, particularly if the amount of blood salvaged is insufficient to fill the bowl with RBCs.

One RBC-washing system marketed by Cobe Laboratories is made almost entirely of flexible PVC. It has the advantage of being able to vary the volume of the rotor to control the final hematocrit but has the disadvantage of being limited to a rather flat, wide pancake-like shape due to manufacturing constrictions. The Cobe system controls the rotor volume by pumping a hydraulic fluid—a liquid—in or out of a bladder that rotates with and squeezes the blood out of rotor. The Cobe system takes up a fairly large amount of space, and its flexible pancake-shaped rotor is awkward to handle. The Cobe system does not permit blood to flow into and out of its rotor at the same time. The Cobe system also does not permit blood to be pulled into the rotor by suction. The Cobe rotor is usually filled with blood by gravity, although the blood may be pumped into the rotor. After the blood has been separated, it is squeezed out of the rotor by pumping hydraulic fluid into the bladder.

Haemonetics Corp. and others have provided systems to collect blood shed during surgery, concentrate and wash the RBCs, and return them to the patient. Existing systems typically use a 3 liter reservoir to collect and coarse filter the blood vacuumed from the surgical site and a separate processing set including a special centrifugal processing chamber to wash and concentrate the red blood cells in order that they may be safely reinfused to the patient. Because of their cost and complexity of use, these systems are used only in operations where relatively large blood loss is expected. The prior-art rotors used for processing blood collected during an operation, made by Haemonetics Corp. and others, must be completely filled with RBCs before any processing can occur, and thus the process takes more time and is not appropriate for use with small people or for an operation with low blood loss. Because the volume of the processing chamber is fixed, the final concentration of the RBCs in the last cycle of the process cannot be easily controlled.

Solco Basel AG makes a filter-based system for wound drains. This wound-drain system has the disadvantage that the blood returned to the patient contains, in addition to the RBCs, substances that may be deleterious to the patient.

There exists the need, therefore, for a centrifugal system for processing blood and other biological fluids, that is compact and easy to use and that does not have the disadvantages of prior-art discontinuous-flow systems. There is also a need for improving the way that blood is processed in a variety of applications, such as apheresis, intraoperative blood-salvage systems, and wound drains, so that the blood processing takes less time, requires less cumbersome equipment, and/or reduces harmful side effects in the patient or donor.

SUMMARY OF THE INVENTION

The present invention provides a container, referred to herein as a rotor, which may be used for collecting and centrifuging biological fluids in a range of volumes. The rotor includes an elastic impermeable wall (diaphragm) which defines at least a portion of a variable-volume processing chamber, where the fluid is centrifuged. The rotor includes a rigid mounting member, to which the diaphragm is mounted and which is held and spun by a chuck.

Preferably, this rigid mounting member includes a wall which together with the elastic diaphragm defines the chamber.

This diaphragm and rigid wall are both referred to herein as boundaries, since each defines a portion of the boundary of the variable-volume processing chamber and each has one side which does not come into contact with the biological fluid. In some embodiments, the diaphragm may be located inside other walls on the exterior of the rotor, such as the rigid boundary wall or an exterior shell.

The rigid boundary wall may be large enough to surround the maximum volume that may be taken up by the chamber, or the rigid mounting member may be only large enough to provide a place where the diaphragm may be mounted and where a chuck can hold and spin the rotor. In a preferred embodiment, the rigid boundary wall is a substantially imperforate circular wall which extends to the periphery of the processing chamber, so as to define the top of the processing chamber; the diaphragm is attached to the perimeter of the wall and defines the remainder of the processing chamber.

As noted above, the rigid wall in one embodiment surrounds the chamber, and the diaphragm is located inside a portion of the rigid boundary wall. In one version of this embodiment, the rotor includes a core located inside the rigid boundary wall and the chamber, and the diaphragm is mounted about the core.

In a preferred embodiment, the rigid boundary wall is substantially imperforate but defines one opening, preferably near the axis of rotation, permitting a conduit or conduits to pass therethrough so as to be in fluid communication with the processing chamber. In another alternative embodiment, the rigid boundary wall has a plurality of openings for controlling the flow into and/or out of the rotor while the rotor is being spun.

Preferably, the rotor includes a separate structure for controlling the flow of liquid out of the chamber into the rotor's (outlet) conduit. In a preferred embodiment, this outlet-control structure is a perforate, substantially rigid wall or plate, located within the processing chamber and mounted adjacent the rigid boundary wall. Since it is located within the processing chamber, and both of its sides come into contact with the biological fluid, this perforate wall is referred to as an interior wall. The perforate interior wall preferably extends substantially to the periphery of the chamber, although in other embodiments it may have a smaller diameter. Although in a preferred embodiment the perforate wall has many holes, in alternative embodiments the perforate wall may have holes located only at a discrete radius or at discrete radii from the axis of rotation. The interior wall may also serve the purpose of protecting the elastic membrane from being abraded from a non-rotating portion of the rotor while the body of the rotor is spun.

In an alternative embodiment, the outlet-control structure for controlling flow from the processing chamber to the conduit includes at least one tube or preferably a set of tubes, wherein each tube provides fluid communication between the chamber and the conduit. The tubes used as the outlet-control structure may have holes along their length to provide additional points of entry for fluid from the processing chamber. In some versions of the rotor, the tube or tubes provide fluid communication from a variety of radii within the chamber; in other versions, the tube or tubes provide fluid communication from a discrete radius or discrete radii within the chamber.

In another preferred embodiment, the outlet-control means may include vertical walls that define channels. These channels may be grooves formed in the interior surface of the rigid boundary wall. As long as the vertical channel walls are spaced close enough to each other (i.e., as long as the grooves are narrow enough), the channels (grooves) will remain open even though the processing chamber is at its lowest volume and the elastic membrane is pressed against the bottom of the vertical walls. Such channels can provide fluid communication to the rotor's outlet conduit from the periphery of the processing chamber to the innermost radius of the processing chamber and all the points in between. The grooves can be shortened so as to provide fluid communication to the outlet conduit from just those points between two radii within the chamber.

In one embodiment of the rotor, a single conduit passes through a portion of the rotor that does not rotate during centrifugation—i.e., the rotor's fixed portion. The fixed portion passes through the rigid boundary wall, and the rigid boundary wall is rotatably mounted around the fixed portion. In another embodiment, two or more conduits pass through a portion of the rotor that does not rotate during centrifugation. This embodiment permits unseparated fluid to flow into the spinning rotor through one conduit, while separated fluid can flow out of the rotor through the other conduit. This embodiment of the rotor may further include a substantially imperforate interior wall, mounted between the boundary wall and the perforate interior wall and around the fixed portion, so as to provide a channel permitting fluid to flow from the rotor's input conduit to the chamber's periphery. This substantially imperforate interior wall does define a center hole through which the rotor's fixed portion passes. The substantially imperforate interior wall may be considered an inlet-control structure which controls the flow of fluid into the rotor—in this case directing the fluid to the rotor's periphery.

Alternative embodiments of the rotor do not have a fixed portion. The conduits extending from these embodiments of the rotor thus spin with the rest of the rotor during centrifugation. A rotary seal may be located at some point in the tubing connecting the rotor with the rest of the processing set. Alternatively, a skip-rope system may be used in lieu of a rotary seal.

The embodiments of the rotor having a fixed portion preferably include a rotary seal that has a base, a spring member, first and second seal faces, which spin in relation to each other, and a flexible seal member. The spring is mounted on the base, and the first seal face is mounted on the spring member so that the spring member presses the first seal face against the second seal face. The seal member prevents flow between the first seal face and the base. Preferably, the flexible seal member and the first seal face are disposed so that the force with which the spring member presses the first seal face against the second seal face is not adversely affected by pressure within the rotor. In a preferred embodiment, the flexible seal member and the spring member are separate members, although they may be made out of different portions of the same piece of material. Alternatively, if the flexible seal member is resilient and rigid enough to apply the proper force between the first and second seal faces, a separate spring member may not be necessary.

In one embodiment, the rotary seal's base is part of the rotor's fixed portion, and the rotary seal's second seal face is attached to the rigid mounting member, which is part of the rotating portion of the rotor. Alternatively, the rotary seal's base may be part of the rotor's rigid mounting member, and the rotary seal's second seal face is attached to the rotor's fixed portion.

The rotor may be spun in a centrifuge system that includes a chuck for holding and spinning the rotor and a pressurized fluid supply for supplying a pressurized control fluid—preferably gas—adjacent the rotor's diaphragm, while the rotor is being spun. The pressurized gas may be used to force fluid out of the rotor's processing chamber. The system preferably includes means for applying a vacuum to the exterior side of the diaphragm (i.e., the side that does not come into contact with the fluid being processed), so as to draw fluid into the processing chamber. In one embodiment, for use with a rotor where the diaphragm is mounted along the bottom of a substantially flat, circular boundary wall, the chuck has extending from a rotatable base an outer peripheral wall, so as to define a cylindrical cavity into which the diaphragm may expand. In one version of this chuck embodiment, the chuck also has extending from its base a core, so that the chuck defines an annular cavity into which the diaphragm may expand. In another embodiment, for use with a rotor that has a core in the rotor's interior, the chuck has extending from a rotatable base a nozzle, through which the pressurized gas is provided through the rotor's core to an area adjacent the rotor's diaphragm. Another embodiment of the chuck holds the rotor from inside a rigid core in the rotor.

In order to make the rotor more portable while biological fluid is being collected in the rotor, a rigid, airtight exterior shell may be attached and sealed to the rigid boundary wall. In one embodiment, the shell may be removably attached to the rotor. The shell permits a vacuum to be applied to the exterior side of the diaphragm when the rotor is not in a chuck. Thus, fluid may be drawn into the processing chamber when the rotor is not in a chuck. A spring bellows may also be used to create a vacuum against the diaphragm.

The system may also include a control system for controlling the rotational speed of the chuck and the gas pressure provided by the gas supply to achieve the most advantageous combination of centrifugal force for separation and gas pressure against the diaphragm required to force fluid out of the rotor. The control system may be programmed to determine the volume of the processing chamber based on the rotational speed of the chuck and the air pressure provided by the chuck.

The rotor and centrifuge systems of the present invention may be used in many different processes involving biological fluid. A method for using the rotor would generally include the steps of introducing an unseparated fluid into the rotor's processing chamber, spinning the rotor so as to separate the fluid into denser and lighter components, and applying pressure to the diaphragm's exterior side so as to force a fluid component—usually the lighter fluid components—through the conduit.

Further aspects of the present invention will be apparent from the following description of specific embodiments, the attached drawings and the appended claims.

DESCRIPTION OF SPECIFIC EMBODIMENTS

Figure 1:
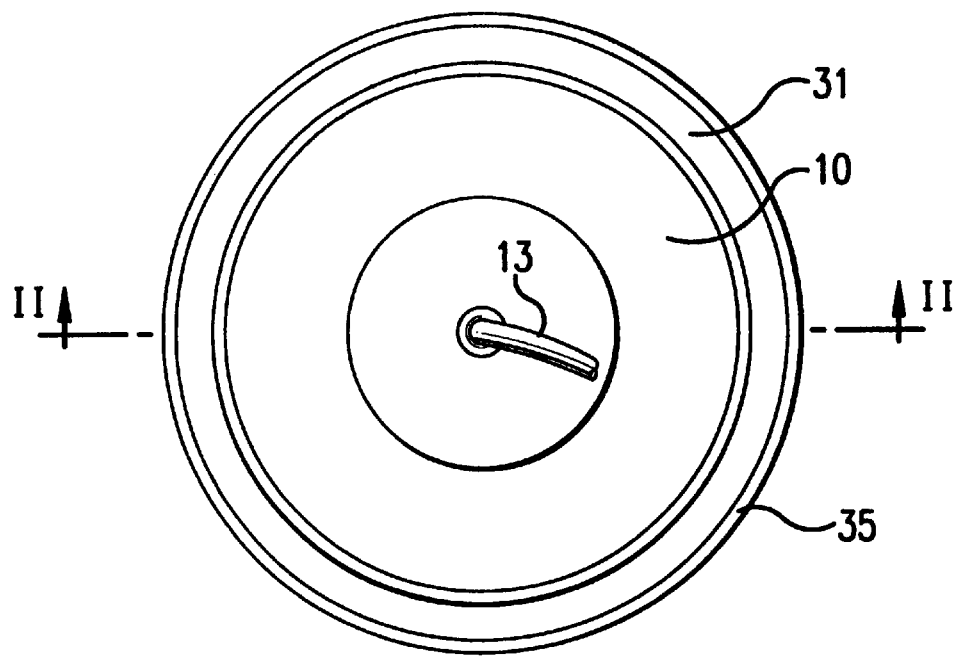
FIG. 1 is a top plan view of a rotor according to the present invention.
Figure 2:
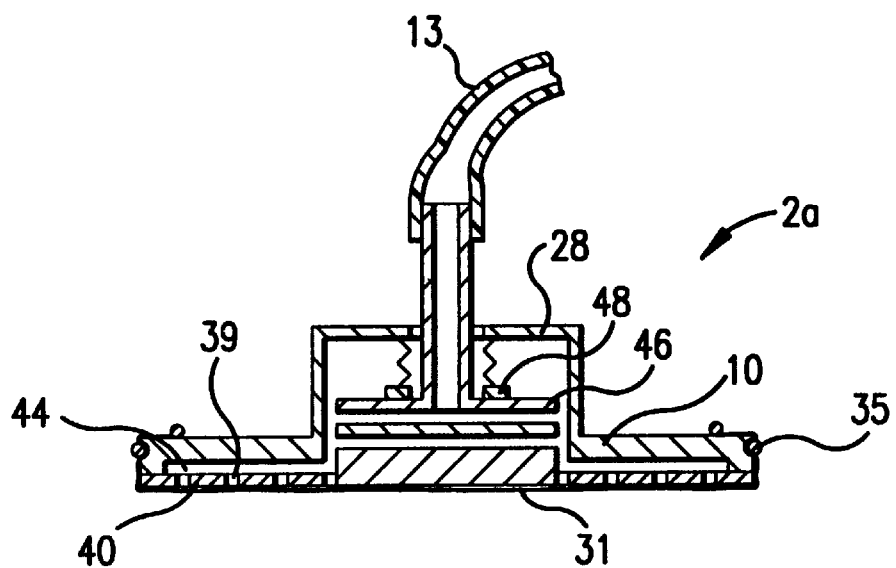
FIG. 2 shows a cross-section of the rotor shown in FIG. 1.

FIGS. 1 and 2 show a version of the centrifuge rotor 2a according to the present invention. The rotor 2a has an elastic boundary, i.e., an impermeable diaphragm 31, which is sealed to a rigid, imperforate boundary wall 10 by an O-ring 35 or other means. The diaphragm 31 is preferably made of an elastic, stretchable and resilient material, such as latex or silicone rubber. A perforate interior wall 40— also referred to as a plate—having holes 39 is attached under the rigid boundary wall 10. Preferably, the boundary wall 10 and the interior wall 40 are made out of a rigid thermoplastic. The perforate interior plate 40 is held a short distance away from the imperforate boundary wall 10 by standoffs (not shown), thereby forming a passage 44.

The rotor 2a also has a collector assembly 46, which is attached to tube 13, and a rotary seal 48, which maintains the sterile environment in the rotor 2a but allows the rotor to turn even while the collector assembly is held stationary. The rotary seal 48 provides a seal between the collector assembly 46 and that portion 28 of the boundary wall 10 that surrounds the collector assembly 46, while permitting the boundary wall 10 to spin around the collector assembly 46 while the collector assembly 46 is held in place.

Figure 5:
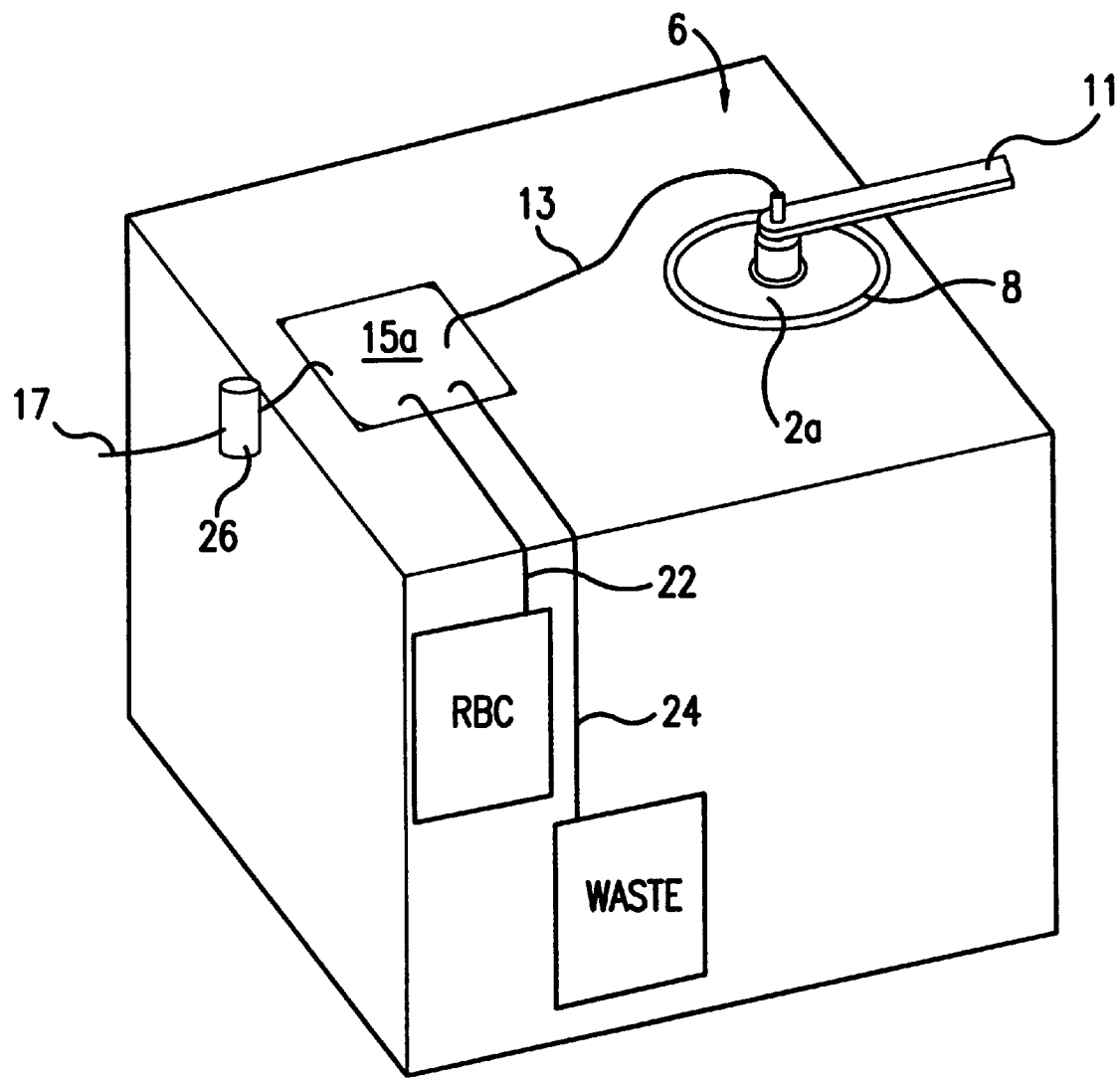
FIG. 5 is a perspective view of a system that may use the rotor in post-operative salvage (i.e., with a wound drain).

Tube 13 is attached to the rest of the disposable processing set (tubing set), which may include a cassette (see item 15a in FIG. 5). The tube 13 and the collector assembly 46 are held fixedly in place, while the rest of the rotor 2a—the rigid boundary wall 10, the diaphragm 31, the plate 40 and any fluids in the variable-volume processing chamber—is spun. Although otherwise imperforate, the boundary wall 10 does of course define a central opening through which the collector assembly 46 can extend to connect with the tube 13.

A variable volume is defined in the rotor 2a between the boundary wall 10 and the diaphragm 31. This variable volume is the processing chamber where the blood is centrifuged and separated. The processing chamber is sealed in by the boundary wall 10 and the diaphragm, so that during centrifugation the only fluid communication between the interior of the processing chamber and outside of the rotor 2a is through the conduit leading to tube 13—or in the embodiments of the rotor having multiple conduits into and out of the rotor (such as those shown in FIGS. 11, 16–18, 19A–19D and 23) through the multiple conduits. The conduit or conduits providing fluid communication with the processing chamber pass through the rotor's fixed portion, which includes the collector assembly 46.

The plate 40 is located within the processing chamber. It is desirable to minimize the volume of the processing chamber above the plate 40 (including the channel), so that as much fluid as possible can be forced out of the processing chamber when the diaphragm 31 is forced against the plate 40. Nevertheless, the passage 44 needs to be wide enough so as to permit sufficiently unrestricted flow from the periphery to the center of the passage 44, even when the diaphragm 31 is forced against the plate 40.

The interior plate's holes 39 allow fluid communication between the areas of the chamber above and below the plate 40. The holes 39 should be small enough to prevent the diaphragm 31 from protruding too far into the passage 44. If they are too large, protrusions of the diaphragm 31 through the plate's holes 39 could restrict flow from the processing chamber's periphery to the center of the channel. The size and placement of the holes 39 may be varied in order to regulate the flow out of the rotor 2a as the rotor 2a is emptied.

If the holes 39 are too large and too close to the collector assembly 46, the portions of the diaphragm could touch the fixed portion's collector assembly 46. Allowing the diaphragm 31 to touch the collector assembly 46 can cause abrasion of the diaphragm if the body of the rotor 2a is being spun while the collector assembly 46 is being held in place, and continual abrasion may cause the diaphragm 31 to eventually rupture. Thus, the plate 40, as well as the top wall 10, separate the spinning diaphragm 31 from the non-spinning tube 13 and the collector assembly 46.

Figure 3:
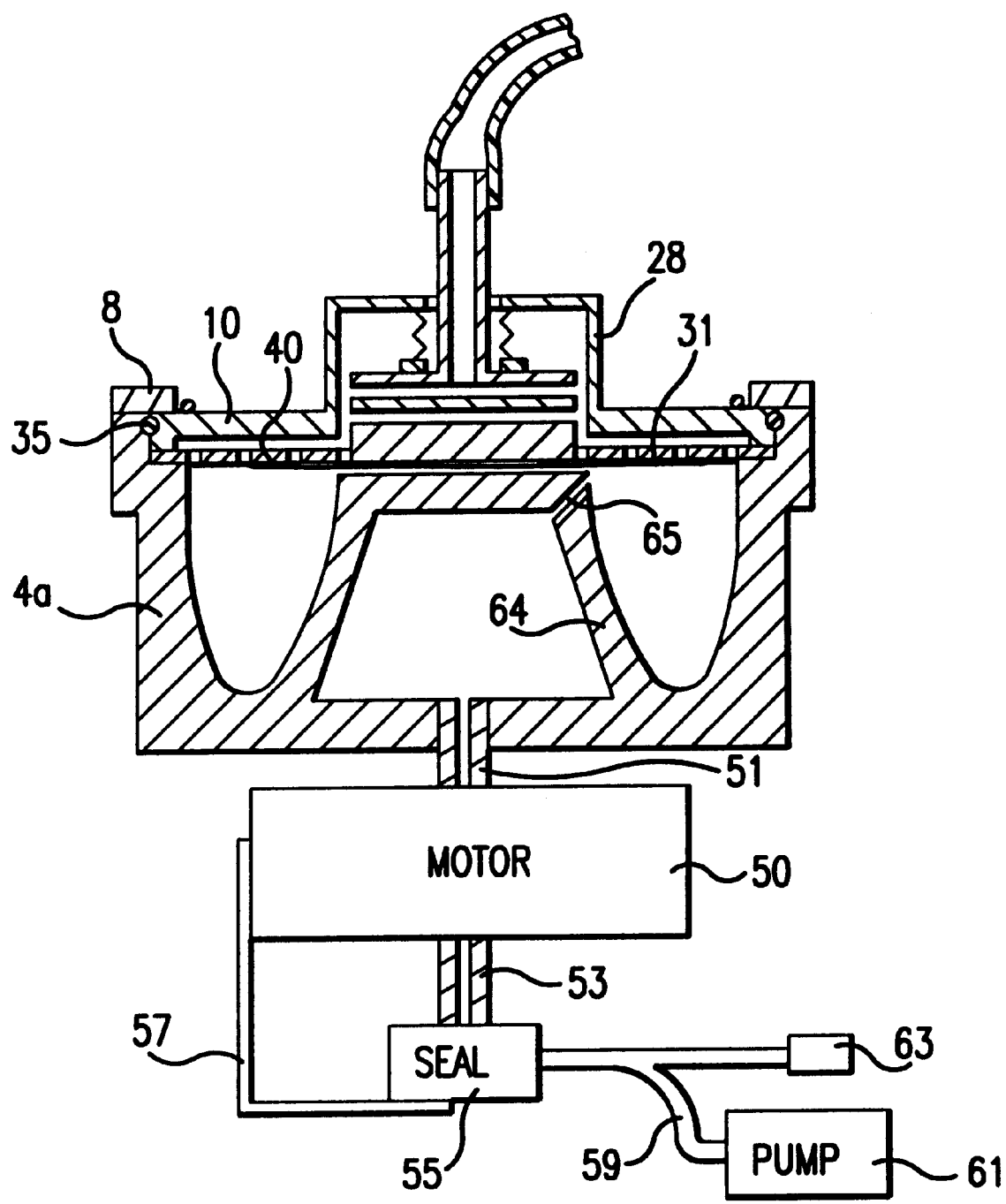
FIG. 3 shows a cross-section of the FIG. 2 rotor and a chuck for holding and spinning the rotor.

In use, the rotor 2a is placed in a centrifuge chuck 4a and held in place by clamp 8, as shown in FIG. 3. O-ring 35 is pressed against an inside wall of the chuck 4a to form an air tight seal. Of course, different configurations may be used in order to create a seal between the rotor 2a and the chuck 4a, such as the use of a lip seal 36 shown in FIG. 12.

In one preferred embodiment, the chuck 4a has a core 64 which limits how far the diaphragm 31 can expand towards the rotor's axis of rotation. Holes 65 in the interior core portion 64 of the chuck 4a allow a control gas, preferably air, to flow from a compressor/vacuum pump 61 to the area of the chuck 4a exposed to the elastic wall 31 of the rotor 2a. Channels extending from the holes 65 may be provided on the inner surface of the chuck, so as to allow air to flow from the holes 65 to various points adjacent the diaphragm 31 when the diaphragm is fully extended (as shown by line 31d in FIG. 4). The chuck 4a is turned by a motor 50 and shaft 51. The shaft 51 has an axial through hole 53 and protrudes below the motor 50. A rotary pneumatic seal 55 is attached to the shaft 51 and is held stationary by a brace 57. The pneumatic rotary seal 55 is connected by tubing 59 to the compressor/vacuum pump 61 and to a controllable exhaust valve 63.

Instead of a rotary pneumatic seal, the tubing 59 may be connected to a compartment attached and sealed to the bottom of the motor 50, so that the bottom of the shaft 51 extends into the compartment; if the motor forms a substantially air-tight barrier enclosing the compartment, this arrangement can be used instead of the rotary pneumatic seal. Instead of using a dual-purpose pump to provide both positive and negative pressure, a separate compressor and vacuum pump may be used to create positive and negative pressures respectively. Alternatively, the negative pressure may be provided by the hospital's vacuum source, which may be supplied to the housing by a vacuum line, while the pump 61 creates the positive pressure.

In the rotor shown in FIG. 2, the imperforate, rigid boundary wall 10 has a diameter substantially equal to the largest diameter of processing chamber, i.e., the space defined by the chuck 4a. In an alternative embodiment, the diameter of the rigid boundary wall 10 may be as small as the collector/rotary-seal area 28. In a rotor having an imperforate wall 10 with a smaller diameter than the perforated interior plate 40, the elastic diaphragm 31 is bent around the periphery of the plate 40 in order to cover that portion of the top of the plate 40 not covered by the imperforate wall 10. (See for example FIG. 35, which shows a rotor that uses tubes to control the flow out of the processing chamber instead of a perforate interior wall.) The chuck for holding and spinning such a rotor should have a lid in order to keep the portion of the diaphragm 31 above the interior plate 40 in the proper shape when the rotor is spun and in order to maintain an air-tight seal. It is desirable that the rigid rotatable portion of the rotor be large enough so that the diaphragm 31 may be mounted on it and so that the chuck 4a may grasp the rigid rotatable portion in order to spin the rotor. In rotors having small-diameter boundary walls, the perforate interior wall 40 or other structure for controlling the flow out of the processing chamber may be modified to fold out of the way when the rotor is being built or stored. During centrifugation, the perforate interior plate 40 should—in a preferred embodiment—extend to the periphery of the processing chamber in order to ensure that fluid can flow from the periphery of the processing chamber to the collector assembly 46, even when the processing chamber is at its smallest volume.

It will be appreciated that using a rotor having a rigid boundary wall extending all the way to the largest diameter of the processing chamber, like that shown in FIG. 2, has the advantages of being easier to use and not requiring the use of a lid on the chuck.

Figure 4:
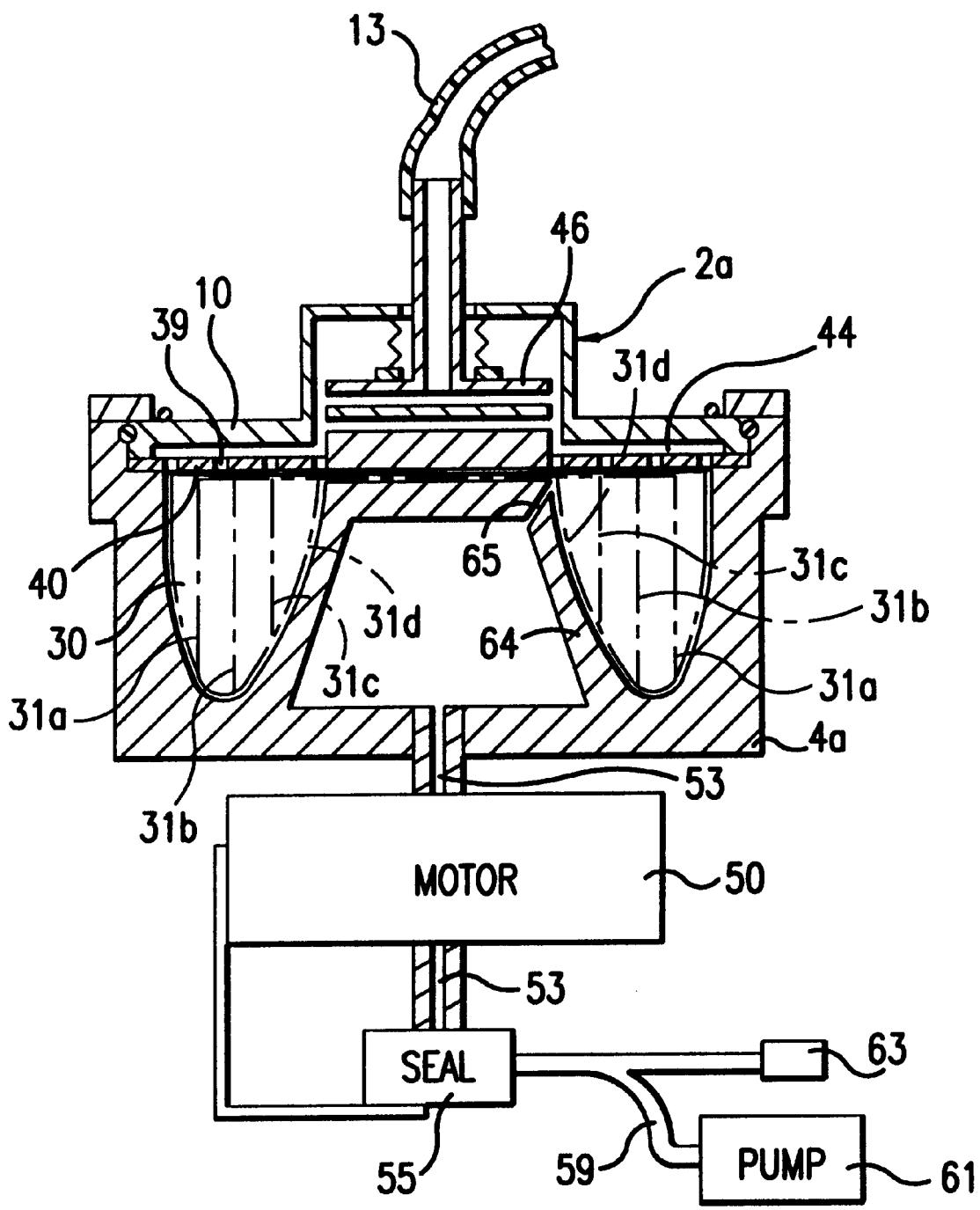
FIG. 4 shows a cross-section of the rotor and chuck system of FIG. 3 showing the shapes of the diaphragm with varying volumes of blood in the rotor.

FIG. 4 shows the rotor 2a while it is spinning and while blood flows into the rotor 2a from the rest of the disposable set. While the body of the rotor 2a is spun by the chuck 4a, the collector assembly 46, including the conduit connected to tube 13, is held in place by a brace (such as brace 11 shown in FIG. 5). When the blood touches either the boundary wall 10 or the interior plate 40, it is propelled by centrifugal force towards the perimeter of the rotor 2a. As more blood enters, it continues to be propelled to the perimeter eventually flowing through the holes in the interior plate 40. As the volume of the blood and the processing chamber 30 increases, the diaphragm stretches to allow the blood to reach the furthest diameter and at some point takes on a shape shown by line 31a. As blood enters the rotor, the air in the chuck 4a that is displaced by the blood escapes through hole 65, down the shaft hole 53 and out exhaust valve 63. If necessary, the blood flow rate can be increased by a vacuum in the chuck 4a generated by the pump 61 or a separate vacuum supply (such as a separate vacuum pump or the hospital vacuum provided through a vacuum line). As more and more blood enters the rotor 2a, the diaphragm changes shape to accommodate the blood. As it is filled further, the diaphragm takes on the shapes shown by line 31b and line 31c and finally, when the rotor is full, takes on the shape of the chuck interior, as shown by line 31d.

As the diaphragm stretches to accommodate the expanding size of the processing chamber 30, it comes into contact with the chuck in a sequential manner. As successive portions of the diaphragm come into contact with the chuck, they may become immobilized and cease to stretch, while those portions of the diaphragm that have not yet come into contact with the chuck continue to stretch, with the consequence that portions of the diaphragm may be subjected to greater stretching than other portions. In order to avoid rupturing of the diaphragm when the processing chamber 30 is filled with blood, the chuck 4a may be shaped so as to minimize variations in the amount of stretching between different portions of the diaphragm.

FIG. 5 shows a system, according to the present invention, for recovering blood drawn by vacuum into a tube 17 from a wound drain. A filter 26 may be provided in the tube 17. This type of system is known as post-operative salvage. A preferred embodiment of the system includes a housing 6, having a small footprint of approximately 8 inches by 11 inches and a height of only about 10 inches. For some applications, even smaller systems, with smaller rotors, may be used. The rotor 2a is held in the chuck, such as the chuck shown in FIGS. 3 and 4, by chuck clamp 8. A vacuum is provided through the chuck to the exterior side of the diaphragm. Because the diaphragm is pulled downward by the vacuum in the chuck, fluid is drawn into the rotor 2a through the rotor tube 13. The blood is thus drawn from the wound-drain site through the tube 17 then through a cassette 15a, which provides valving to control the flow of fluids through the various lines, and then through the rotor tube 13 to the rotor 2a. Standard valves or valving techniques (e.g., pinching a tube) may be used to control fluid flow in the system instead of a cassette 15a. Anticoagulant may be added to the drained blood at some point during the process.

An intermediate wound-drain canister may be placed in the line 17 between the patient and the cassette 15a. The filter 26 may be located adjacent to or in this canister, and anticoagulant may be added to the blood in the canister. Such a canister can hold the whole blood pulled from the patient until the blood is to be processed; at that time, the vacuum generated in the chuck or a pump may be used to pull the blood from the canister to the rotor 2a.

When it is desired to separate the blood in the rotor 2a, the chuck spins the body of the rotor 2a. In a preferred version of the post-operative salvage process using the present invention, blood flow to the rotor 2a is stopped when the desired or the available amount of blood has entered the rotor, or when it is full. Since, in the rotor of the present invention, the processing chamber has a variable volume, the rotor 2a does not have to be filled to its capacity with blood for the process to be done properly. After the flow into the rotor is stopped, the blood is then subjected to centrifugal force as long as is appropriate to separate the various components. The portion of the rotor 2a where the rotor tube 13 enters the rotor 2a (i.e., the fixed portion, which as noted previously in connection with FIG. 4 includes the collector assembly 46) is held and prevented from spinning by a brace 11.

Referring to FIG. 4, when the separation is complete, the compressor begins to pump compressed air into the chuck 4a. When the air pressure acting on the diaphragm's exterior (i.e., the side that does not come into contact with blood) exceeds the fluid head between the collector assembly and the inner vertical face of the diaphragm (lines 31a, 31b, 31c and 31d), fluid begins to flow from the processing area in the rotor through the holes 39 in the interior plate 40 into the area around the collector assembly 46, through the collector assembly and out of the rotor 2a into the rotor tube 13. The fluid head between the collector assembly and the inner vertical face of the diaphragm is created by the centrifugal force acting on the fluid in the channel 44. In order to minimize the amount of air pressure needed to overcome the centrifugal force of the rotor, the rotational speed of the rotor 2a may be reduced—at some point during the process—to a level that is high enough simply to keep the blood components separated.

It should be noted that while the use of air is described herein to apply pressure to the diaphragm 31, other fluids could be used as well. Preferably a gas is used, since a gas will have a lower specific gravity than the lightest separated fluid in the processing chamber and therefore will stay between the liquid being centrifuged and the rotor's axis of rotation. Air is preferred since it is readily available and easily disposed of. Nitrogen or carbon dioxide may be used instead.

The compressed air first pushes the blood element with the lightest specific gravity out of the processing area. the lighter fluid passes through those holes 39 in the plate 40 at the smallest radius not sealed by the diaphragm 31. Each blood element in turn by specific gravity flows through the holes 39 in the plate 40 at the smallest radius not yet sealed by the diaphragm 31 and then out of the rotor.

Referring to FIG. 5 again, the blood elements exiting the rotor can be diverted as desired by the cassette 15a. The fluid flowing out of the rotor's processing chamber may be diverted to a specific container (e.g., a waste bag or an RBC bag) or returned to a donor depending on the purpose of the process, on how the system is configured and on how the cassette 15a or other tubing directs the fluids.

In a typical post-operative salvage process using the present invention, the lighter elements—most of the plasma and platelets—are considered waste and are sent through the cassette 15a (or other valving mechanism) and the tube 24 to a waste bag. The remaining blood elements—mostly concentrated RECs—may then be further processed in the rotor 2a and then forced out of the rotor 2a through the cassette 15a and the tube 22 to an RBC bag. After a sufficient amount of RBCs are sent to the RBC bag, the RBC bag is disconnected from the cassette 15a and may then be attached to the patient in order to return the patient's RBCs.

The emptying of the processing chamber 30 of the rotor 2a can be stopped at any time by stopping the increase in the air pressure inside the chuck 4a, while maintaining the rotational speed of the chuck. If the rotor is processing blood, one likely place to stop might be when the RBC layer begins to exit the rotor and another might be when the rotor is empty.

The cycle of sending fluids into the rotor, centrifuging and forcing fluids out of the rotor 2a can be repeated, for instance for further processing of the blood components left in the rotor (for instance, washing the RBCs or ficol-hypaque separations). Other fluids can be allowed to flow into the rotor and back out again by inflating or deflating the diaphragm 31 and appropriately actuating the cassette 15a (shown in FIG. 5). At the end of the last cycle in the post-operative salvage process, the air pressure in the chuck 4a can be adjusted to the proper level to obtain the desired hematocrit in the final product.

The rotor speed may be changed at different times while the rotor is emptying, in order to achieve the most advantageous combination of centrifugal force for separation and air pressure inside the chuck required to force fluid out of the rotor. It is desirable to avoid applying too much air pressure against the outside of the diaphragm 31, for safety considerations, and for reducing the size of the system components and the power consumed by the system.

Thus, in a preferred embodiment the rotor is emptied in the following manner, with reference to FIG. 4. Initially, the rotor 2a is spinning at full processing speed—say for instance 5000 rpm. The gas in the chuck 4a is positively pressurized, thereby causing fluid to flow out of the rotor's chamber 30 until an equilibrium is reached between the gas pressure in the chuck and the centrifugal force acting on the fluid in the channel 44 above the plate 40 between the outer edge of the collector assembly 46 and the inner vertical face of the diaphragm (lines 31a, 31b, 31c and 31d. The gas may continue to be pressurized until it reaches 2 psi—or whatever pressure limit is chosen. Then, the rotational speed of the rotor 2a is reduced. The rotational speed may be reduced without affecting the separation of the fluids in the rotor if the speed is reduced smoothly and slowly, and as long as the rotational speed does not fall below the minimum speed necessary to maintain separation, which may for example be as low as 500–1500 rpm. Reducing the speed lowers the centrifugal force on the fluid in the channel 44. Thus, additional fluid is forced out of the rotor until a new equilibrium is reached. By continuing to reduce the rotor's rotational speed, additional fluid is forced out of the rotor even though the gas pressure in the chuck 4a is kept constant.

Alternatively, fluid may be forced out of the rotor 2a with low gas pressure by first reducing the rotational speed of the rotor 2a to the desired level—for instance, the lowest speed which will maintain separation—and then increasing the pressure in the chuck 4a. It is also possible to reduce the rotational speed and increase the gas pressure at the same time. An advantage of this technique of emptying the rotor—namely, reducing the rotational speed of the rotor to assist in emptying—is that less gas pressure in the chuck is needed to force liquid out of the rotor.

The chuck's gas pressure and rotational speed may be controlled by a controller (preferably, a digital data processor located in the system housing 6, which housing is shown in FIG. 5), which receives information from a pressure transducer for measuring the gas pressure in the chuck 4a and from an encoder for measuring the rotational speed of the chuck 4a and the rotor 2a. The controller may control the compressor 61 and the motor 50, in addition to valves in the rest of the disposable set. The controller may also be programmed to calculate the volume of liquid in the rotor's processing chamber based on the chuck's gas pressure and the rotational speed.

In order to avoid excessive vibration of the system as the rotor is being spun, the speed of rotation may be varied. For instance, instead of trying to maintain a constant speed of rotation of 5000 rpm, the motor may cycle through a range of speeds around 5000 rpm. This cycling will help avoid the motor staying at a rotational speed that puts the system into a resonant vibration. The rotational speed should be changed quickly enough so that the system does not have an opportunity to resonate at a given speed, yet the speed should not be changed so quickly that the separation of the fluid components is upset.

At some point in the emptying, only one component will remain in the rotor, for instance red blood cells (or only components whose separation is not required will remain in the rotor). At that point, the foregoing process may continue until the rotor 2a is empty or, preferably, the spinning of the rotor 2a may be stopped. The gas pressure necessary to push the remaining liquid out of the rotor 2a when it is stopped must only be greater than the fluid head from the rotor 2a to the highest point in the tubing between the rotor and the collection bag.

Figure 6:
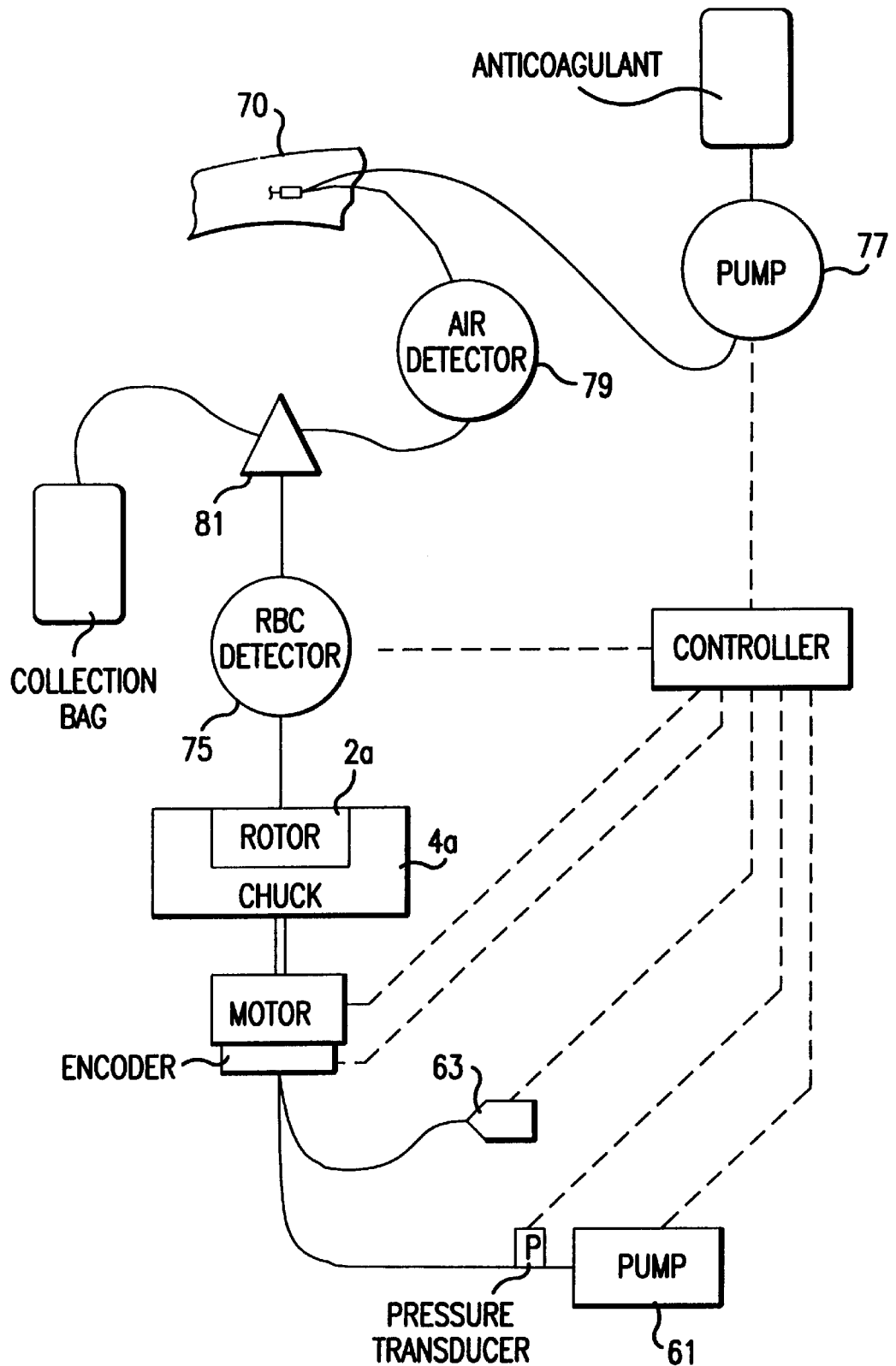
FIG. 6 is a schematic of a system to utilize the rotor as a donor-connected apheresis system for the collection of plasma or RBC.

FIG. 6 is a schematic of a system to utilize the rotor 2a described above in a donor-connected apheresis system for the collection of RBCs. A suitable anticoagulant is metered into the blood at the end of the needle which has been inserted into a vein in an arm of the donor 70. The flow of anticoagulant is controlled by a pump or other metering device 77. The anticoagulated blood flows through the donor tubing and into the rotor by the combination of gravity and venous pressure and, if needed, vacuum from compressor/vacuum pump 61 or a peristaltic pump. At this point during the process, valve 81 closes off the component collection bag and permits flow to the rotor.

After sufficient blood enters the rotor, the rotor is spun quickly enough and long enough to cause adequate separation. The valve 81 remains in the position where the donor tubing is open and the tubing to the collection bag is closed. While the chuck continues to spin the rotor in order to maintain separation (although the rotational speed may be reduced), the compressor 61 pumps air into the chuck forcing plasma to flow back to the donor. The plasma flowing back to the donor is checked for air bubbles by the air detector 79. As the RBCs start to emerge from the rotor, as detected by RBC detector 75, the valve 81 opens the tubing to the collection bag and closes the tubing to the donor. When the rotor is empty, the compressor stops and the pressure in the rotor is vented through vent 63. The process can be repeated as desired.

If plasma is to be collected instead of RBCs, the valve 81 would first shunt the plasma exiting the rotor to the collection bag. Then, when RBCs were detected by the RBC detector 75 the valve 81 would open the donor tubing and permit the RBCs to be sent to the donor. The valve 81 may be placed in a cassette, like cassette 15a (shown in FIG. 5), which may provide chambers for detecting RBCs and air bubbles and which may further provide supplemental pumping means.

FIG. 6 shows a controller regulating the anticoagulant pump 77, the valve 81, the chuck's motor, the vent 63 and the pump 61. The controller is connected to an encoder or tachometer to monitor the motor's speed, and is connected to a pressure transducer to measure the gas pressure being applied to the exterior side of the rotor's diaphragm. The controller also monitors the air detector and the RBC detector. As discussed above in relation to FIG. 5, the controller may increase the gas pressure in the chuck and/or reduce the rotational speed of the chuck in order to force the blood components out of the rotor.

In this embodiment, no separate pump is required to move blood to or from the rotor (although pumps may be used). Standard peristaltic blood pumps can create a large amount of pressure or suction and therefore require special devices to protect the donor from excessive suction while drawing blood and from excessive pressure when returning blood. In this system, the draw and return pressures can be controlled exclusively by the air pressure from the chuck and therefore can be controlled and monitored much more safely and with less cost for both the equipment and the disposables. The potential for runaway blood pumps is also reduced by the system above.

The FIG. 2 rotor 2a may also be used for recovering blood suctioned from the surgery site on a patient during an operation. This type of system is known as intraoperative salvage. A suction canister, which is attached to a hospital's wall vacuum (or which utilizes a vacuum pump in the system housing), draws blood from the patient's surgery site through a suction tube. Anticoagulant may be provided to the canister in order to prevent the blood from clotting. Normally, in the intraoperative salvage process, the suctioned blood has been diluted with saline which was used to irrigate the surgery site.

The blood that has corrected in the canister is drawn from the canister through a cassette or other valving mechanism to the rotor tube 13 and finally to the rotor 2a. Blood flow to the rotor is stopped when the desired or the available amount of blood has entered the rotor, or when it is full. (As noted above, since, in the rotor of the present invention, the processing chamber 30 has a variable volume, the rotor 2a does not have to be filled to its capacity with blood for the process to done properly.) The rotor 2a is spun so as to separate the blood into its components. When the separation is complete, like the post-operative process discussed above in relation to FIG. 5, the compressor (item 61 in FIGS. 3, 4 and 6) may begin to pump compressed air into the chuck, and the rotational speed of the rotor 2a may be reduced to a level that is high enough simply to keep the blood components separated. As discussed above in relation to FIG. 4, when the air pressure acting on the exterior of the diaphragm 31 exceeds the fluid head from the inner radius of the diaphragm 31 to the skirt of the collector 46, fluid begins to flow from the processing area in the rotor 30 through the holes 39 in the plate 40 into the area around the collector assembly 46, through the collector assembly 46 and out of the rotor 2a into the rotor tube 13.

Like the post-operative salvage system discussed above in connection with FIGS. 4 and 5, in an intraoperative salvage process, the lighter components—primarily the saline and the plasma—are the first components to be pushed out of the rotor 2a through the rotor tube 13. In a typical intraoperative process, these components are considered waste and are shunted by the cassette to a waste bag. After the waste components are pulled from the rotor 2a, the remaining blood components, which now have a higher concentration of RBCs, are pushed through the rotor tube 13 and then shunted by a cassette (or other valve means) to an RBC bag. After a sufficient amount of RBCs are sent to the RBC bag, the bag is disconnected from the cassette and connected to the patient in order to return the patient's RBCs. Alternatively, a tube may be connected directly between the patient and the bag so that blood may be returned directly to the patient by gravity without removing the bag.

Figure 7:
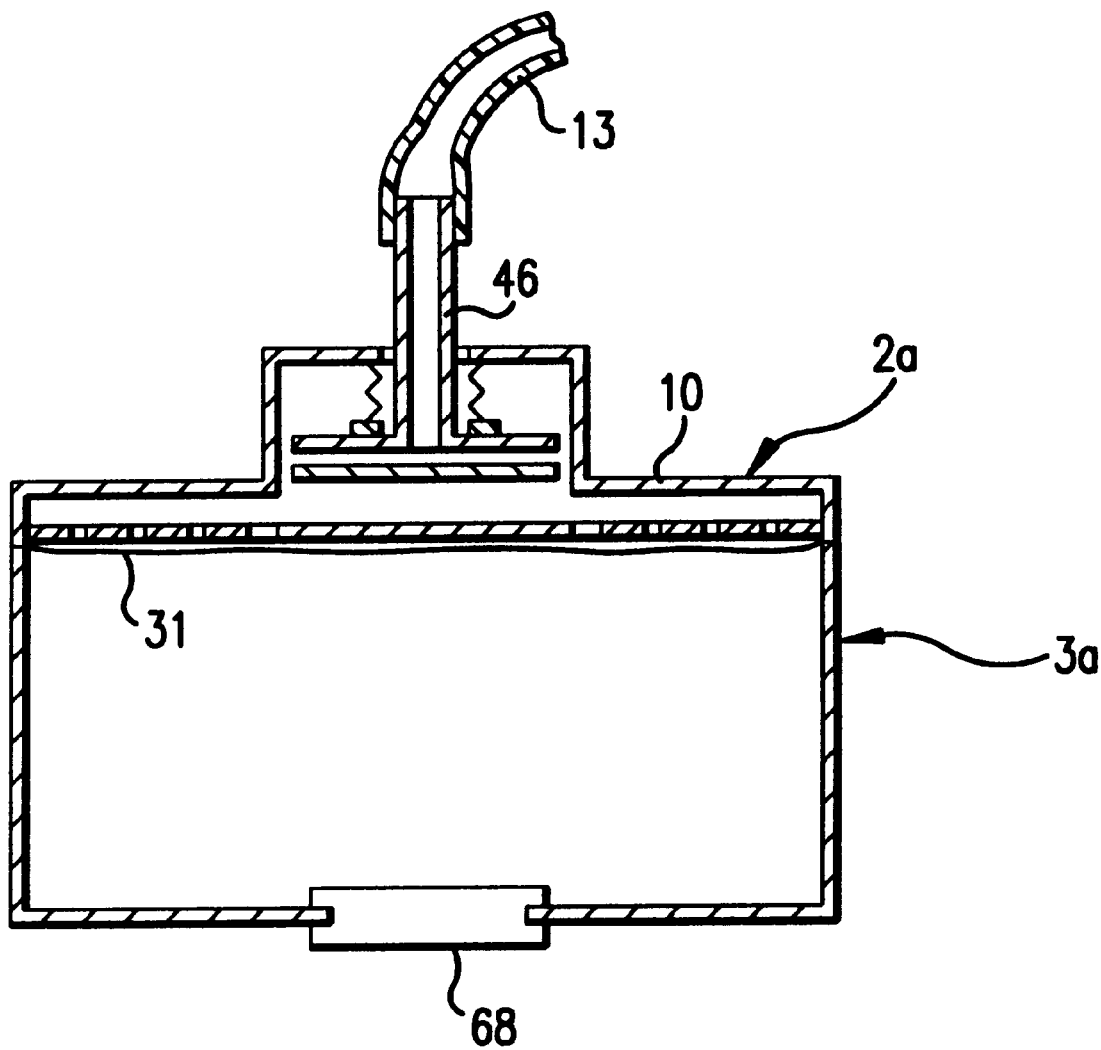
FIG. 7 shows a cross-section of a rotor with an exterior shell.

FIG. 7 shows the rotor 2a of FIG. 2 with an airtight exterior shell 3a attached and sealed to the boundary wall 10. The use of an exterior shell makes the FIG. 2 rotor 2a especially convenient for use as a wound drain. In one embodiment, the shell 3a may be removably attached to the rotor 2a. The shell 3a permits a vacuum to be applied to the exterior side of the diaphragm 31 (i.e., the side that does not come into contact with the blood) without placing the rotor 2a in the chuck 4a. A valve 68 is disposed in the shell 3a. The valve 68 permits the shell 3a to be attached to the hospital vacuum or a vacuum pump. A vacuum is thus introduced into the shell 3a, and the vacuum in the shell 3a draws blood from the wound drain. With the FIG. 7 configuration, the rotor 2a can begin drawing blood from the wound drain as soon as the wound drain is placed in the patient—typically in the operating room—without mounting the rotor 2a in the chuck 4a. Later—when the patient is brought into the recovery room—the rotor 2a can be placed in a chuck to process the drained fluid. If the shell 3a is removable, it may be removed from the rotor 2a, and the rotor 2a may then be placed in the chuck 4a shown in FIG. 3. If the shell 3a is not removable, a different chuck may be used. Such a chuck would have means for opening valve 68 in order to permit fluid communication between the chuck and the interior of the shell 3a. Preferably, such a chuck would provide a compressed gas in order to force fluid out of the rotor 2a. In addition, such a chuck would also preferably be able to provide a vacuum to the interior of the shell 3a in order to draw additional fluid into rotor 2a. The shell 3a also protects the diaphragm 31 from accidental abrasions.

Figure 8A:
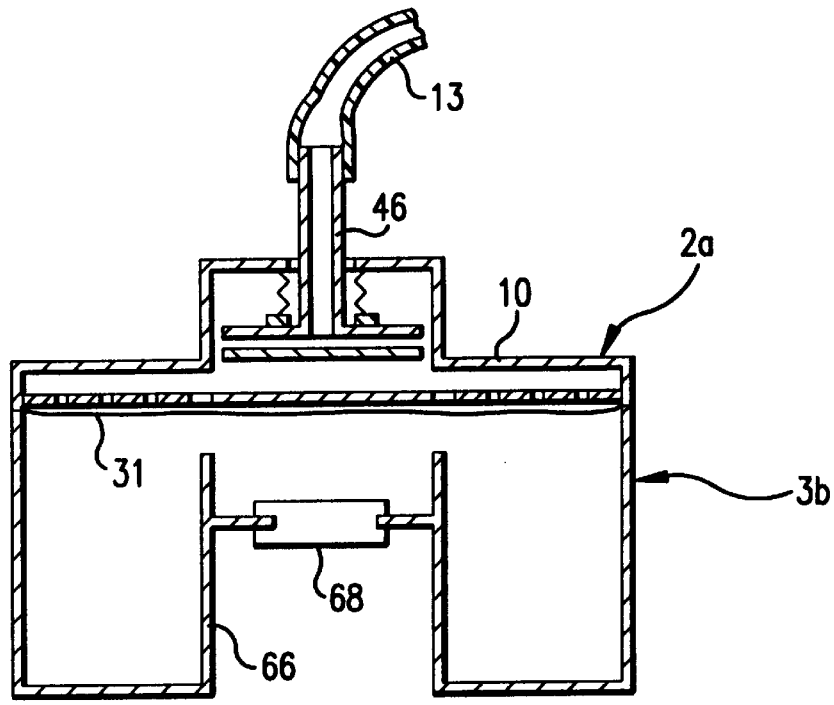
FIG. 8A shows a cross-section of a rotor with an alternative exterior shell.

An alternative shell 3b is shown in FIG. 8A. This alternative shell 3b has a core 66 that extends up from the bottom of the shell 3b around the rotor's axis of rotation. Near the top of this core 66 is the valve 68, which is normally closed but which may be opened for permitting either a vacuum or positive pressure to be introduced into the interior of the shell 3b.

If the shell 3a, 3b remains attached to the rotor 2a during centrifugation, the shell may be shaped so as to reduce variations in the stresses in the diaphragm 31 (like the chuck shown in FIG. 3 for example). Also, if the shell 3a, 3b remains attached to the rotor 2a during centrifugation, the diaphragm 31 may be attached to the bottom of the shell and/or to the core 66.

Figure 8B:
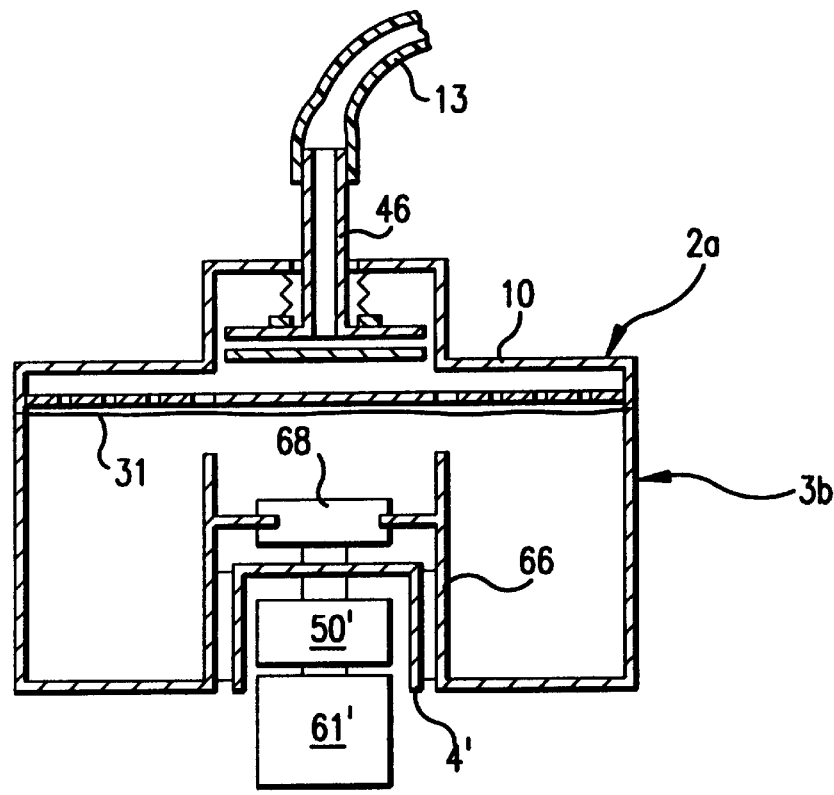
FIG. 8B shows a cross section of the rotor shown in FIG. 8A mounted on a chuck located within the core of the rotor's shell.

As shown in FIG. 8B, using a rotor having a shell 3b with a core 66—or a rotor like rotor 2c shown in FIG. 20 (discussed below) having a core 116 which is part of the rigid boundary wall 10—permits the use of a chuck 4' that fits inside the core 66, so that the rotor 2a and shell 3b may be held from the inside of the core 66, instead of the outside of the rotor like the chucks 4a and 4c shown FIGS. 3 and 21. Such an arrangement permits a smaller system housing to be used, and the motor 50' and perhaps even part of the pump 61' may be located within the rotor's core.

Figure 9:
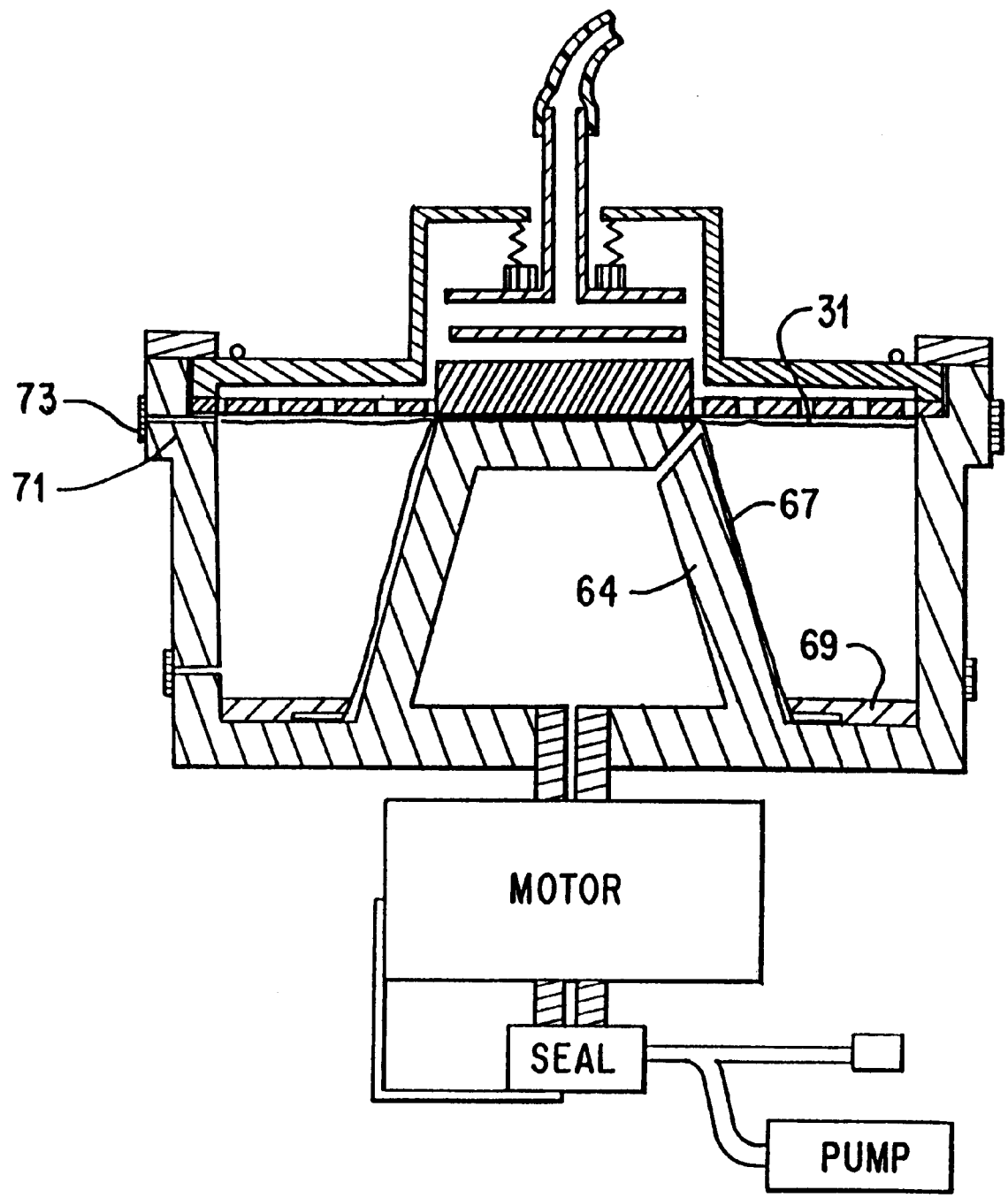
FIG. 9 shows a cross-section of the FIG. 2 rotor in an alternative chuck.

FIG. 9 shows the addition of a secondary elastic wall 67 in the chuck. This secondary elastic wall 67 is held in place by clamp 69. This secondary elastic wall is a barrier between the air in the chuck and the diaphragm 31 of the rotor and would prevent pressurized air entering the rotor's processing chamber in the event of a tear in the diaphragm 31. Operationally, this configuration of the system would work in a manner very similar to that described above except that before blood was allowed to flow into the rotor, the pump would inflate the secondary elastic wall 67 until it completely filled the chuck. The air in the chuck would be forced out holes 71, which are covered by one-way valves 73 to prevent air from re-entering the chuck.

Figure 10:
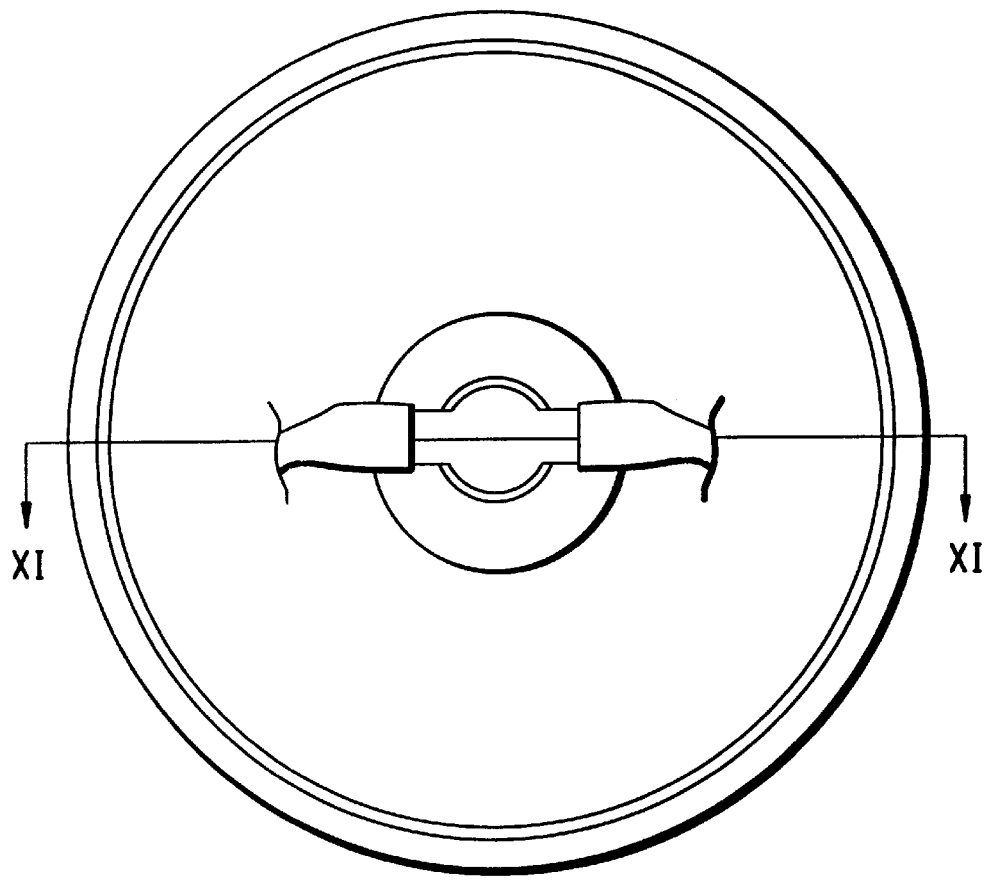
FIG. 10 is a top plan view of a two-conduit rotor.
Figure 11:
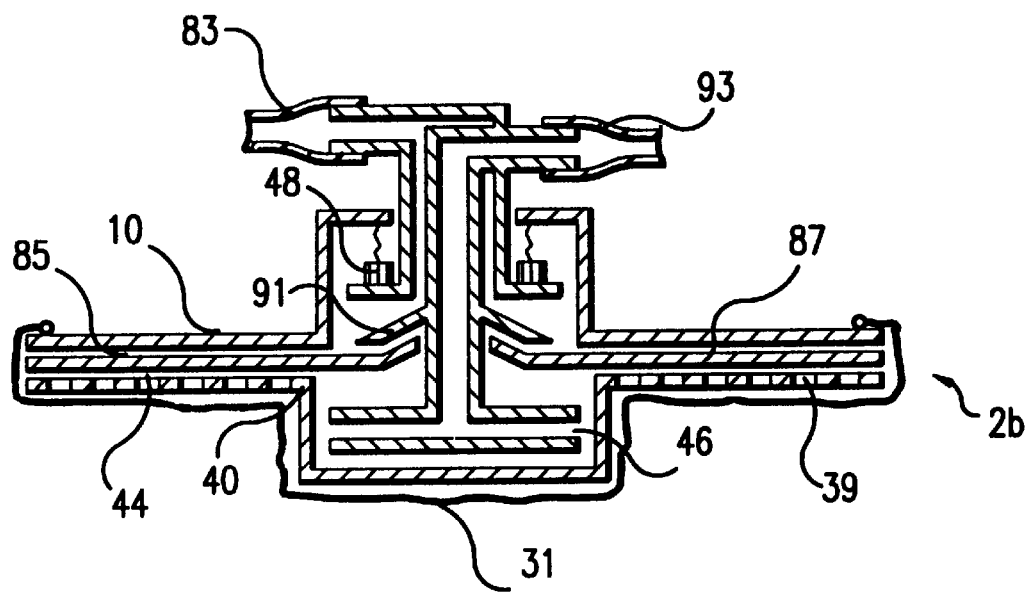
FIG. 11 shows a cross-section of the FIG. 10 rotor.

FIGS. 10 and 11 show respectively a top plan view and a cross-section of a two-conduit, edge-loading rotor, which permits flow into and out of the rotor 2b at the same time. Like the rotor 2a shown in FIG. 2, the FIG. 11 rotor 2b has an elastic diaphragm 31, a plate 40 with holes 39, and a boundary imperforate wall 10. (Most of the boundary imperforate wall, as in an alternative embodiment mentioned above in connection with rotor 2a, can be substituted for with a portion of the diaphragm 31 extending over the top of the rotor and adapting the chuck to include a lid. See FIG. 35.) These portions of the rotor are spun by a chuck. Like the FIG. 2 rotor, the FIG. 11 rotor 2b also has a collector assembly 46, which is held in place while the rest of the rotor is spun. The FIG. 11 rotor may be modified so that the bottom rigid wall, i.e., the perforate interior wall 40, is flat—like the perforate plate 40 shown in FIG. 2.

The FIG. 11 rotor further includes a second imperforate wall 87 (which is also referred to herein as an inlet-control structure or an imperforate interior plate) located between the top imperforate wall 10 and the perforate interior plate 40, so as to form a channel 85 between the two imperforate walls. Like the rigid boundary wall 10, the interior imperforate plate 87, although otherwise imperforate, does define a central opening to permit the collector assembly 46 to pass through. This second plate 87 is also spun along with the perforate interior plate 40, the top wall 10 and the diaphragm 31. The rotor 2b also has an umbrella deflector 91, which directs the unseparated fluid along the top of the imperforate interior plate 87. Instead of a single input/output tube 13 of the FIG. 2 rotor, the FIG. 11 rotor 2b has an input tube 83 and a separate output tube 93, which together with the collector assembly 46 are held in place during centrifugation while the rest of the rotor is spun.

Figure 12:
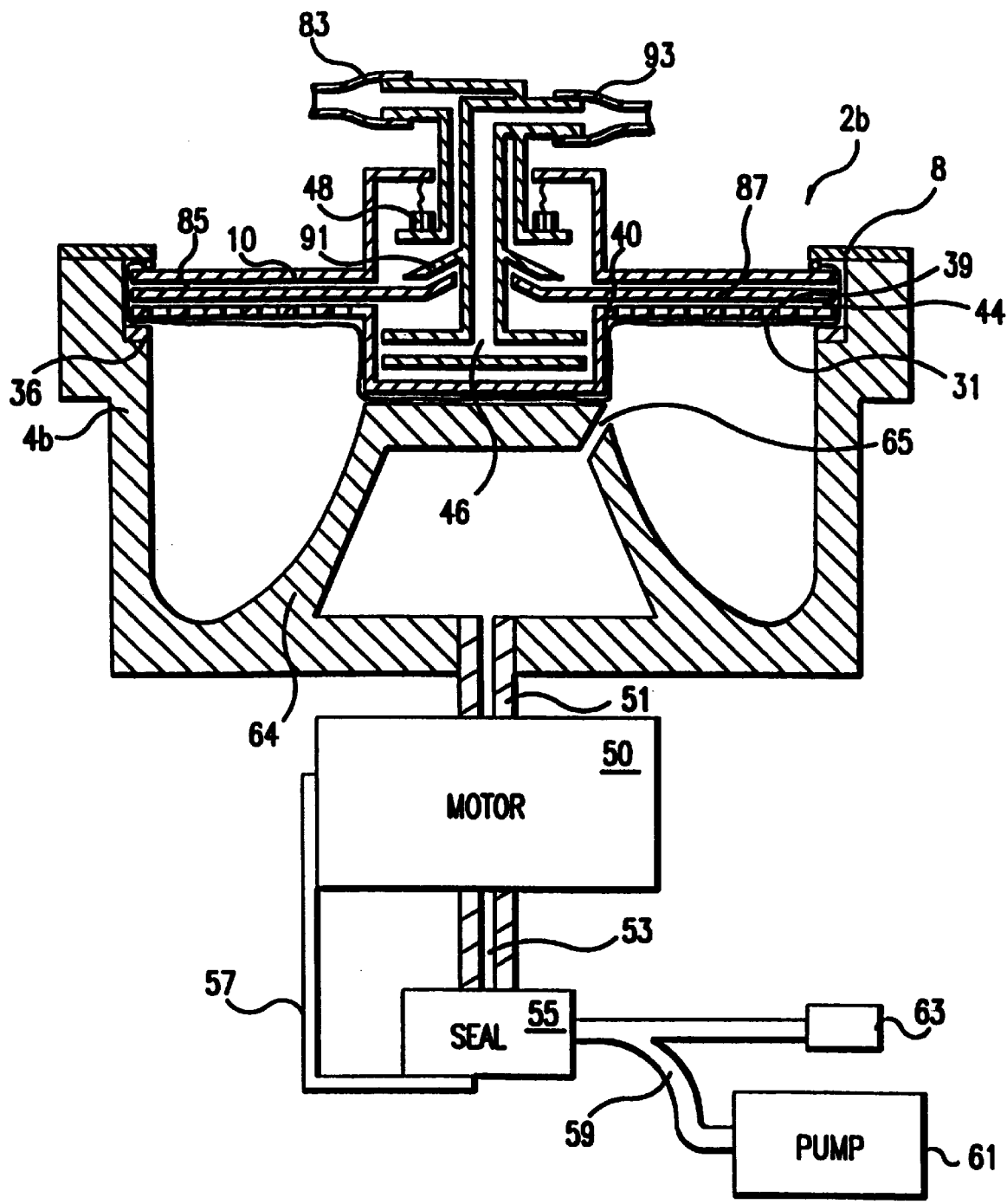
FIG. 12 shows the FIG. 11 rotor mounted in a chuck.

In use, the rotor 2b is placed in centrifuge chuck 4b, as shown in FIG. 12. (The interior of chuck 4b has a somewhat different shape from that of the FIG. 3 chuck 4a. The shape of the chuck's interior may be varied depending on whether the rotor is usually filled while being spun by the chuck or while at rest.) The rotor 2b is held in place by clamp 8. Lip seal 36 interfaces with the rotor to form an air-tight seal. The centrifuge is turned by motor 50 and shaft 51. The shaft 51 has an axial through hole 53 and protrudes below the motor 50. A rotary pneumatic seal 55 connects tubing 59 to the shaft 51 and is held stationary by fixture 57. (Alternative means for providing substantially air-tight fluid communication between the tubing 59 and the axial through hole 53 as discussed above may be used in lieu of the rotary pneumatic seal 55.) The tubing 59 connects the rotary pneumatic seal 55 to the compressor/vacuum pump 61 and to a controllable exhaust valve 63. Holes 65 in the chuck core 64 allow air to flow from the compressor into the space between the chuck and the diaphragm. (As noted above in connection with the FIG. 3 chuck 4a, channels emanating from the holes 65 may be provided in the chuck so that fluid may flow to various points adjacent the exterior of the diaphragm even when the diaphragm is fully extended.)

Figure 13:
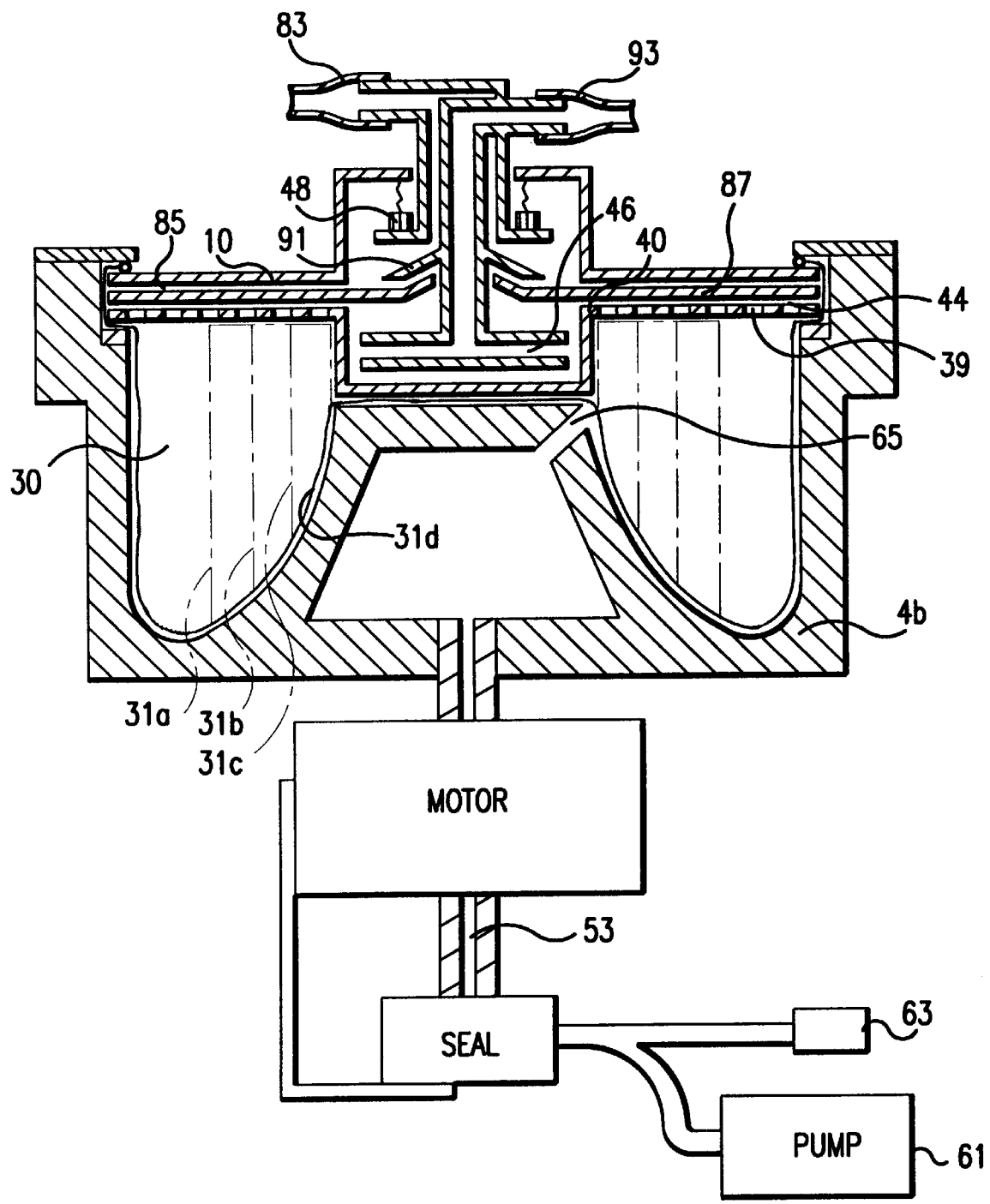
FIG. 13 shows a cross-section of the FIG. 12 rotor and chuck system showing the shapes of the diaphragm with varying volumes of blood in the rotor.

FIG. 13 shows the rotor 2b spinning. Blood flows into the rotor through tube 83, then the blood flows off umbrella deflector 91 and is channeled to the outside edge of the rotor through channel 85. As the volume of the blood in the rotor 2b increases, the diaphragm 31 stretches to allow the blood to fill the processing area and at some point will take on a shape shown by line 31a. As blood enters the rotor, the air in the chuck 4b, which is displaced by the diaphragm 31 and the blood, escapes through hole 65, down the shaft hole 53 and out exhaust valve 63. As more and more blood enters the rotor, the diaphragm changes shape to accommodate the blood. The diaphragm will in turn take on the shapes shown by lines 31b, 31c and 31d.

In the FIG. 11 rotor 2b, unprocessed blood or fluids can flow into the rotor 2b, while the lighter blood elements can simultaneously flow out of the rotor 2b. This flow pattern is similar to the flow pattern in rotors marketed by Haemonetics, Electromedics and Shiley. One distinction between those prior-art rotors and the present invention is that when it is time to harvest the heavier components from the rotor 2b (typically red blood cells) the compressor 61 turns on and increases the air pressure in the chuck 4b, forcing any remaining lighter elements out of the rotor 2b until the desired concentration of remaining products is achieved. Once the desired concentration is achieved, the remaining products can be harvested from the rotor 2b by further increasing the air pressure in the chuck 4b. Alternately, if the rotor 2b is stopped, the remaining elements can be harvested with low air pressures in the chuck 4b or even pumped out through either tube 93 or tube 83.

A further distinction between the FIG. 11 rotor 2b and prior-art rotors is that by controlling the air pressure in the chuck 4b the increase in the volume of blood in the rotor 2b can be stopped at any position such as 31a in FIG. 13. At that time, the flow pattern of unprocessed fluids entering the rotor 2b (via tube 83 and channel 85) simultaneously with the lighter elements leaving the rotor 2b (via channel 44, collector assembly 46 and tube 93) takes place but with a chosen rotor volume that is smaller than the rotor's maximum volume. One important advantage of this rotor 2b and process described herein is that the variable volume of the rotor's processing chamber 30 makes it ideal for use for the intraoperative or post-operative salvage of shed blood. If the patient is small or if the blood loss has been gradual, it may be desirable to harvest the collected RBCs from the rotor 2b before the rotor is completely full of RBCs. This cannot be done in the prior-art systems unless the operator is willing to accept a low hematocrit product. With the FIG. 11 rotor 2b, the operator can keep the rotor's processing chamber 30 at the appropriate volume with air pressure in the chuck to suit the needs of the patient.

If the rotor 2b is already fully expanded but there are not very many RBCs in the rotor when it is desired to harvest those RBCs, the compressor 61 is used to increase the air pressure in the chuck 4b, thereby forcing out the lighter waste products until the desired concentration of RBCs is achieved. The RBCs can then be harvested from the rotor 2b by one of the means described above.

Another important advantage of this rotor 2b and system is that its variable volume makes it ideal for use in blood apheresis. Some apheresis blood collections such as platelet and RBC collections work better or faster if blood entering the rotor is forced to the edge of the rotor. These apheresis blood collections can be performed with less extracorporeal volume and therefore on smaller donors and from donors who are sensitive to blood volume changes. The extracorporeal volume is controlled by keeping the rotor's processing chamber 30 at the appropriate volume with air pressure in the chuck 4b.

Figure 14:
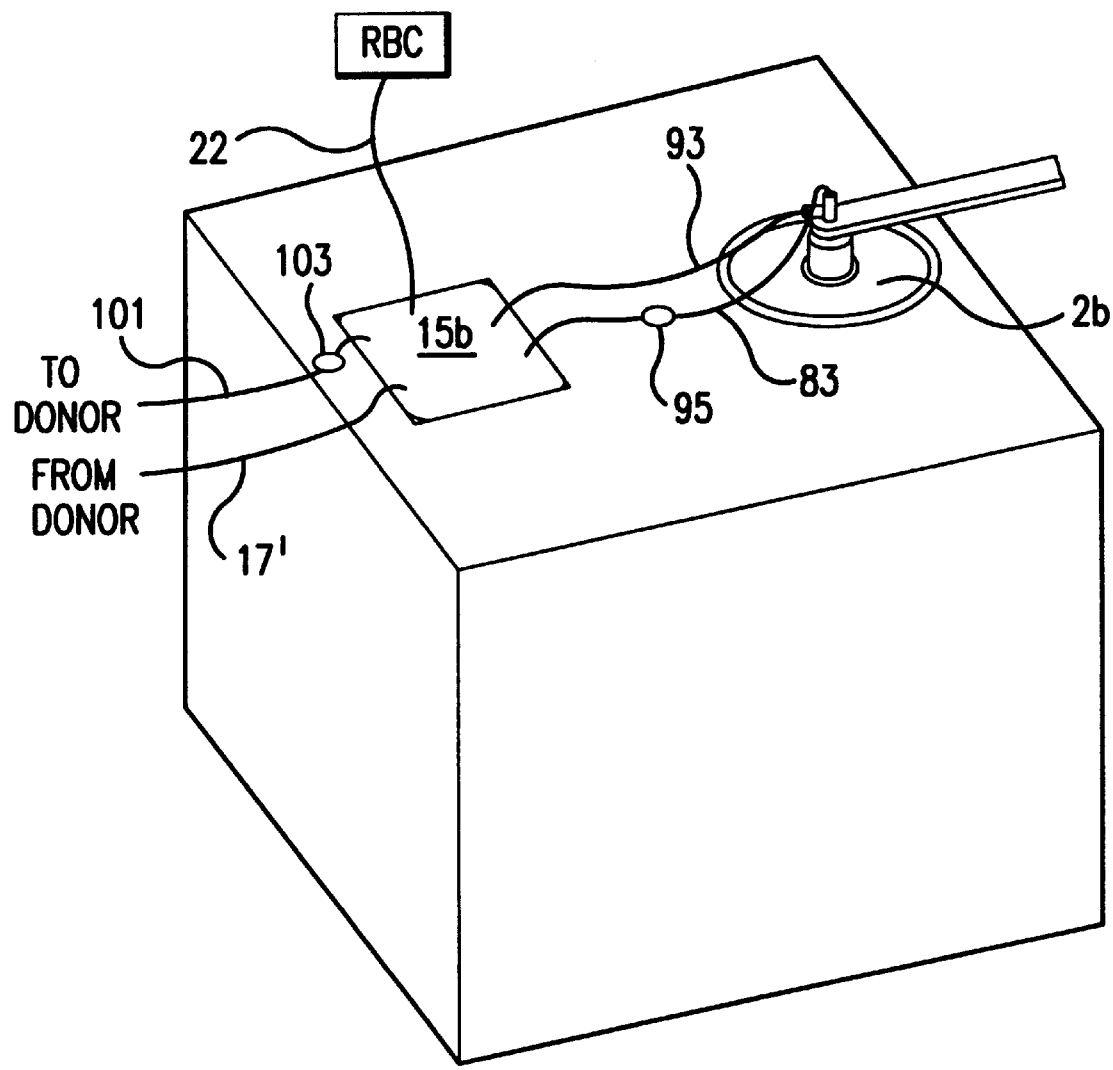
FIG. 14 is a perspective view of a system used in RBC apheresis.

The FIG. 11 rotor 2b may be used in a system, such as that shown in FIG. 14 for performing RBC apheresis. With this system, whole blood is drawn from the donor through tube 17', preferably with the assistance of a pump 95 to the cassette 15b, which directs the whole blood to the input tube 83. With the introduction of fluid into the rotor 2b, the diaphragm 31 is distended in much the same way as shown in FIG. 13. Usually, the rotor 2b is spinning while it is being filled. After separation is complete, while the rotor is still spinning, and while blood is still being introduced into the rotor 2b, the plasma—the lighter blood component—can be forced, by air pressure in the chuck, through the plate's holes 39 (see FIG. 13) to the collector assembly 46 to the output tube 93 to the cassette 15b (see FIG. 14) and finally to the tube 101 for returning the plasma back to the donor. A pump 103 may be used to assist in the return of plasma to the donor. Thus, the plasma may be returned to the donor while whole blood is still being taken from the donor and introduced into the rotor.

Once the desired volume of the processing chamber is established, the air pressure may be used to keep the volume constant; thus, the incoming whole blood will force out a corresponding volume of plasma. Preferably, however, the volume may be allowed to grow so that the volume of plasma exiting the rotor is the same as the volume of the plasma component of the whole blood entering the rotor. At some point the rotor's processing chamber may become filled with RBCs. At that point the pump 95 is turned off so that no more blood is drawn from the donor, and the RBCs are forced out of the rotor 2b through the cassette into a line 22 connected to an RBC bag.

By using the FIG. 11 rotor 2b—or the rotor 2d shown in FIG. 23 and described below—for RBC apheresis, one does not have to wait for the rotor's processing chamber to be filled with whole blood before returning plasma to the donor. Likewise, the chamber does not have to be filled with RBCs before they can be forced out of the rotor's processing chamber through the cassette 15b and into the RBC bag. This flexibility permits the plasma to be returned to the donor gradually, while the donor is still giving blood. This gradual return permits the plasma to be re-introduced to the donor over a longer period of time. This is desirable because the plasma contains most of the anticoagulant, for example, citrate. Citrate can cause an adverse reaction in some donors, especially if introduced into the donor too quickly. The rotor 2b, 2d also permits the processing of any given amount blood up to the maximum amount permitted by the rotor 2b, 2d. As noted previously, prior-art systems using fixed-volume rotors require that a fixed amount of blood be processed. With the variable-volume rotors 2b, 2d, a donor may be allowed to donate less than a standard unit of RBCs, which is advantageous in many situations, such as children and other donors with low body weight. These rotors 2b, 2d may also be used to minimize donor reactions caused by both the total amount of extracorporeal volume and the rate of change of extracorporeal volume.

Figure 15:
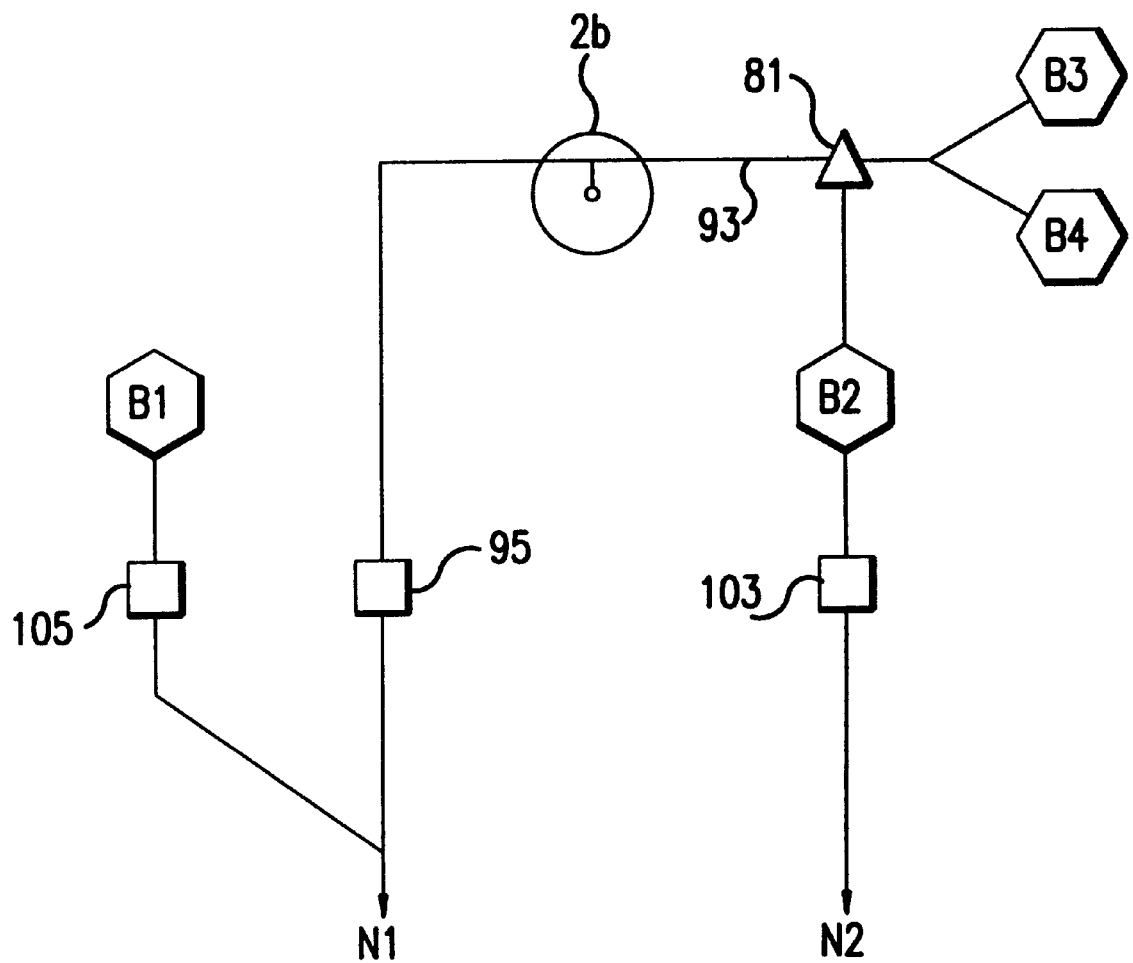
FIG. 15 is a schematic of a system for RBC apheresis.

FIG. 15 schematically represents a particular RBC apheresis process using rotor 2b—or rotor 2d. This process permits the collection of up to two-units of RBCs from a donor quickly and safely. (Donor monitoring and safety systems, such as bubble detection, are not shown in the FIG. schematic for clarity. Likewise, a controller is not shown in FIG. 15. A digital data processor is preferably used for monitoring and controlling the various components of the systems in all of the various processes set forth herein.) Anticoagulant is pumped by pump 105 from bag B1 down to needle N1 which has been inserted in the donor's vein. The anticoagulant mixes with the blood at the needle hub and both are pumped by pump 95 to the rotor 2b—or alternatively rotor 2d. The rotor's processing chamber volume is initially held small by air pressure in the chuck, say at a volume of 100 ml. When plasma starts to emerge into tube 93, the air pressure in the chuck is slowly decreased (by venting air through vent 63 shown in FIG. 13) thereby allowing the rotor's processing chamber to expand at the rate that the RBCs are entering the rotor as part of the whole blood. As the anticoagulated plasma emerges from the rotor, it flows to bag B2 and then is pumped back to the donor by pump 103 via needle N2 inserted in a different vein.

This procedure keeps all the RBCs in the rotor but continues to force the anticoagulated plasma out of the rotor 2b so it can be returned to the donor on a continuous basis. The process continues until the desired amount of RBCs have been collected or until the rotor is full of RBCs. The air pressure in the chuck can then be increased by turning on compressor 61 (see FIG. 13) to achieve the desired concentration of RBC's. The RBCs are then harvested from the rotor and stored in bags B3 and B4 by stopping the rotor, maintaining the proper air pressure to push the RBCs out of the rotor 2b and switching valve 81 to open the passageway to the bags B3 and B4. If desired, RBC preservative solutions can be provided in bags B3, B4. This procedure results in plasma being returned to the donor sooner than is possible with the fixed-volume prior-art rotors and results in plasma being returned to the donor in a continuous stream. Therefore, the peak extracorporeal blood volume is lower and there is less extracorporeal volume fluctuation for the donor, thereby reducing the potential for adverse reactions.

One important factor in RBC apheresis is how long the donor is connected to the system. This factor is particularly important in mobile blood collections where donors are only available for a limited time, such as during blood drives at factories. The system shown in FIG. 15 is particularly fast because the plasma is being returned at the same time whole blood is being drawn and there are no stoppages to empty the rotor until the process is complete and the donor is disconnected from the system.

The plasma in the blood pathway of this FIG. 15 system is always in motion. In addition, the volume of the blood pathway filled with anticoagulated plasma is small, and the length of time any particular drop of plasma is out of the body is short and predictable. Therefore, since there is less propensity for the plasma to clot, the amount of citrate in the anticoagulant may be reduced from standard levels without danger of the plasma starting to clot. With less citrate in the system, the potential for donor citrate reactions is reduced further. (As noted above, the potential for citrate reactions is also reduced because, with the present invention, the anticoagulated blood may be returned to the donor over a longer period of time.)

Another advantage of this system is that it will allow the collection of RBCs from small donors and/or patients whose size or medical condition prevents them from donating with existing systems. Unlike the traditional bag systems and systems that use a fixed volume rotor, the FIG. 15 system causes only a low extracorporeal volume and can be stopped after any amount of RBCs have been collected. Further, the RBCs can be harvested as REC concentrate. The operator simply stops the expansion of the diaphragm after the appropriate amount of RBCs have been collected, increases the air pressure in the chuck slightly to concentrate the cells and then harvests the RBCs.

It is sometimes desirable to replace the blood volume given by the donor. This can be accomplished simply in this process by pre-filling bag B2 with an appropriate amount of an acceptable solution, such as 500 ml of saline. This replacement fluid is then simply reinfused along with the plasma.

Alternatively, the citrate required for proper anticoagulation can be further reduced and the donor can be kept isovolemic simultaneously by putting the replacement fluid such as saline or another injectable solution in bag B1 along with the anticoagulant and increasing the ratio of anticoagulant/saline to blood by adjusting the relative rates of pumps 105 and 95. Adding saline to the blood path in this manner will dilute the plasma, and the saline will travel intermixed with the plasma through the system. Diluting plasma with saline extends the clotting time so that less total citrate is needed to keep the plasma from clotting in the short time the plasma is outside of the donor's body. The same saline thus performs two functions: first, by helping to anticoagulate the plasma and, second, by being the replacement fluid as well. This arrangement has the additional advantage of reducing the percentage of plasma trapped in the RBCs because the plasma is diluted by the saline before it is trapped by the RBCs. The amounts of white blood cells and platelets trapped in the packed RBCs are also reduced because the saline provides a type of elutriation to wash them out with the plasma.

A variation of the above system that requires only one needle but has a longer processing time is achieved by connecting the tube from pump 103 into the tubing between needle N1 and pump 95. With this tubing arrangement and safeguards to insure both pumps are never on at the same time, the system can alternate between drawing blood with pump 95 and returning blood with pump 103 through the same needle N1.

In the FIG. 11 rotor 2b, the spinning top wall 10 and interior plate 40, as noted above, separate the spinning diaphragm 31 from the non-spinning input 83 and output 93 tubes and the top of the collector assembly 46. It is important to keep rigid members that spin with the diaphragm 31 between the diaphragm and the non-spinning components of the rotor, so as to prevent the diaphragm 31 from touching a non-spinning component during centrifugation. (Some embodiments of the rotor do not have a fixed section and therefore do not have to use their interior walls to perform this function. See for example FIG. 28, discussed below.) In addition to preventing the diaphragm 31 from touching the rotor's fixed portion, the plate 40 also serves the important function of controlling flow out of the processing chamber to the collector assembly 46. The interior walls 40 of the rotors 2a, 2b shown FIGS. 2 and 11 (and of the rotors shown in FIGS. 20, 23, 28 and 39, which are discussed below) extend to the periphery of the processing chamber and thus keep a channel 44 open between the periphery of the interior wall 40 and the collector assembly 46, no matter what the position of the diaphragm 31 is. If the interior wall 40 did not extend substantially all the way to the rotor's periphery and did not have holes 39 at the rotor's periphery, the fluid at the periphery of the spinning processing chamber 30 could be prevented from flowing to the collector assembly 46 by the diaphragm 31.

Figure 16:
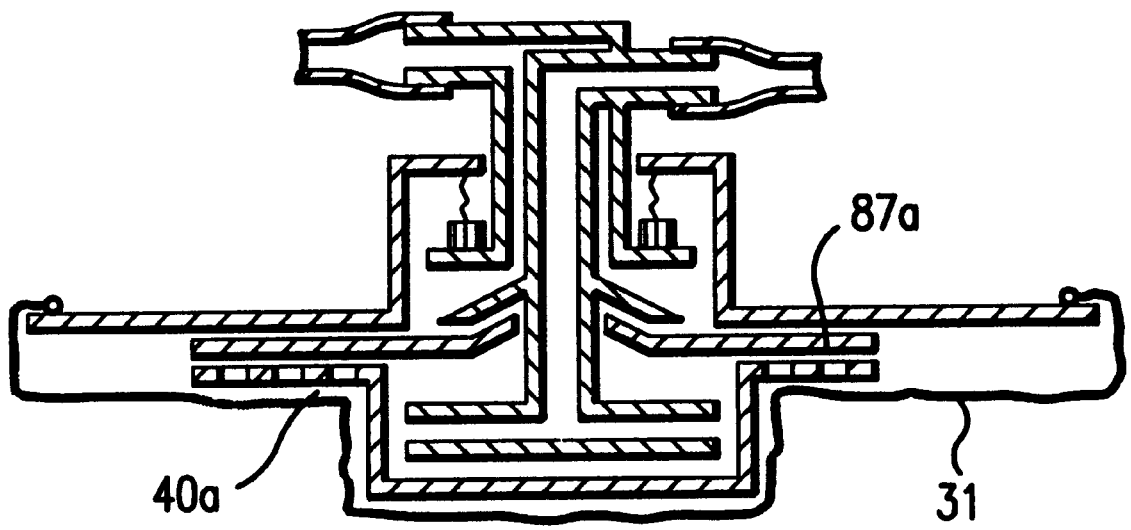
FIGS. 16–18 show cross-sections of several alternative rotors having varying configurations of interior walls and fixed portions.

FIG. 16 shows an example of a rotor with a perforate interior plate 40a and a rigid imperforate interior plate 87a that do not go all the way to the edge of the rotor. In the FIG. 16 rotor, the imperforate interior plate 87a and the perforate interior plate 40a shown extend about halfway to the edge of the FIG. 16 rotor as an example. These perforate and imperforate interior plates (walls) could extend to any desired radius, depending on the desired application of the rotor. With this configuration of interior plates, the channel between the perforate interior plate 40a and the imperforate interior plate 87a remains open during centrifugation as long as the volume of the processing chamber is greater than a defined amount. Once the processing-chamber volume drops below that amount, the diaphragm 31 blocks off further flow out of the processing chamber into the channel. This may be desirable during certain processes involving biological fluids. The imperforate plate 87a does not have to have the same radius as the perforate interior wall 40a. For instance, the imperforate interior wall may extend all the way to the rotor's periphery while the perforate interior wall extends only halfway to the periphery. Such a configuration would allow the rotor to be filled from the outer edge of the imperforate interior wall.

Figure 17:
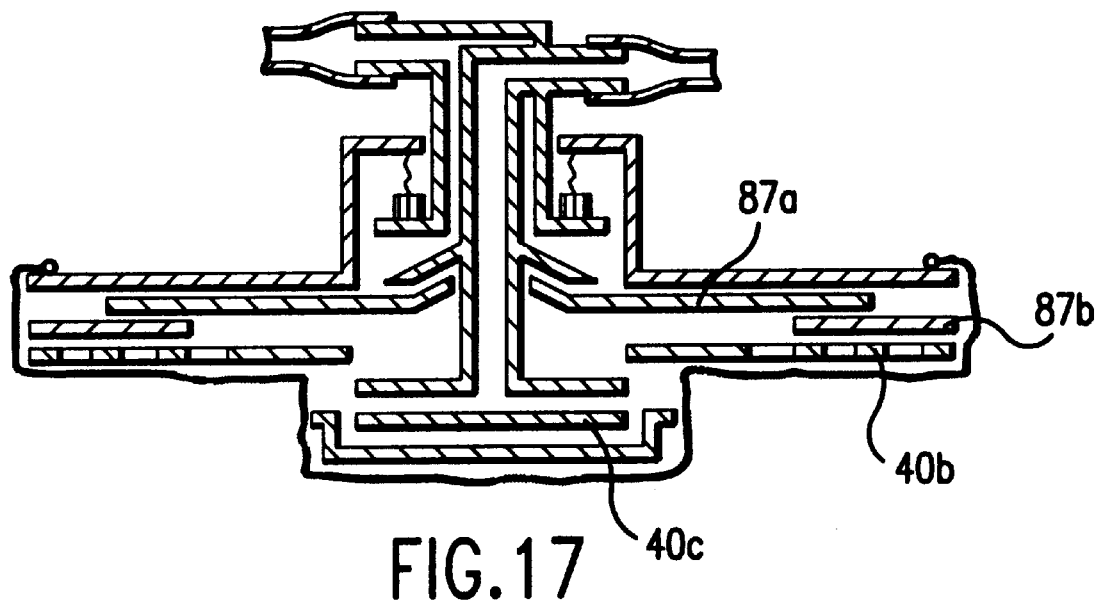

FIG. 17 shows another alternative rotor with a different configuration of interior plates 87a, 87b, 40b and 40c. In this rotor, fluids enter the processing chamber at different radii depending on how full the rotor is; likewise, fluids leave the rotor at different radii depending on how empty the rotor is.

Figure 18:
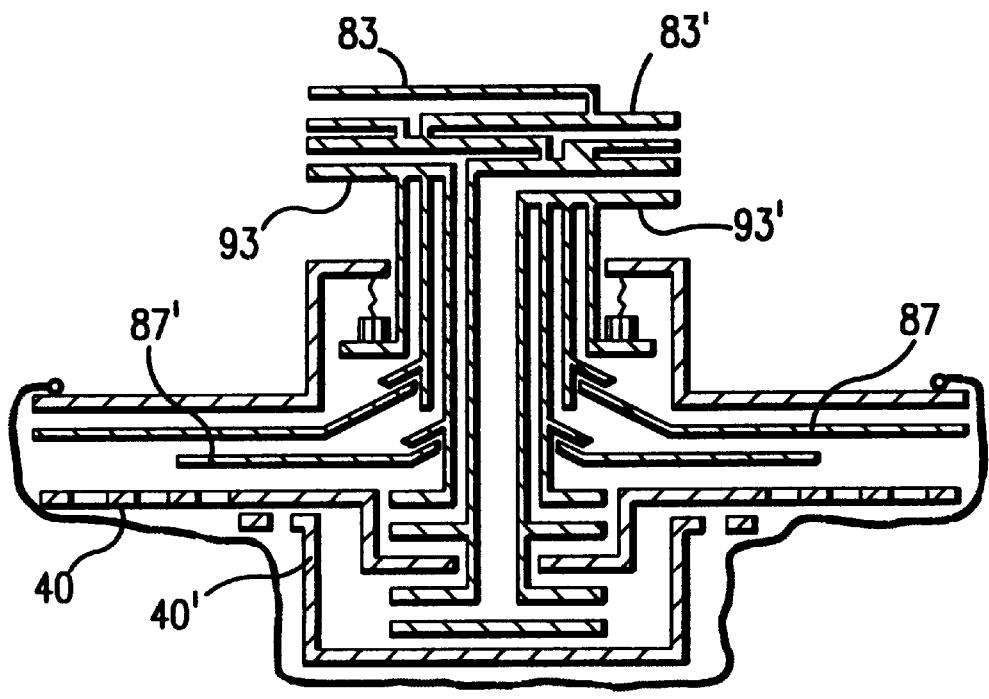

As shown in FIG. 18, the interior walls 87, 87', 40, 40' can be stacked and connected to inlets 83, 83' or outlets 93, 93', so that fluids can enter or leave the processing chamber at different points. In the FIG. 18 rotor, fluids can enter and leave the rotor's processing chamber from multiple radii at the same time. Imperforate plate 87 defines one radius—near the rotor's periphery—where fluid enters the processing chamber, and imperforate plate 87' defines a second, intermediate radius where fluid enters the processing chamber. In the FIG. 18 rotor, like the FIG. 16 rotor, a perforate wall 40' does not extend all the way to the periphery of the processing chamber. Thus, the FIG. 18 rotor, like the FIG. 16 rotor, can prevent further flow over the top of the interior wall 40' to a collector assembly at a particular point during emptying. The rotor in FIG. 18 has two inlets 83, 83' and two outlets 93, 93' allowing a multiplicity of flow patterns depending on how full the rotor is and which tubes connected to the inputs and the outputs are clamped or open.

Another way to use interior plates to accomplish the desired flow patterns is to strategically place holes in the plates. For instance, in FIG. 19A the fluid first exits the rotor in the middle through a set of holes 39', all of which are at a constant radius, even if the rotor is completely full. This configuration permits an intermediate-density fluid, such as platelets, to be emptied from the processing chamber while the lightest and heaviest fluids remain in the rotor.

Figure 19A:
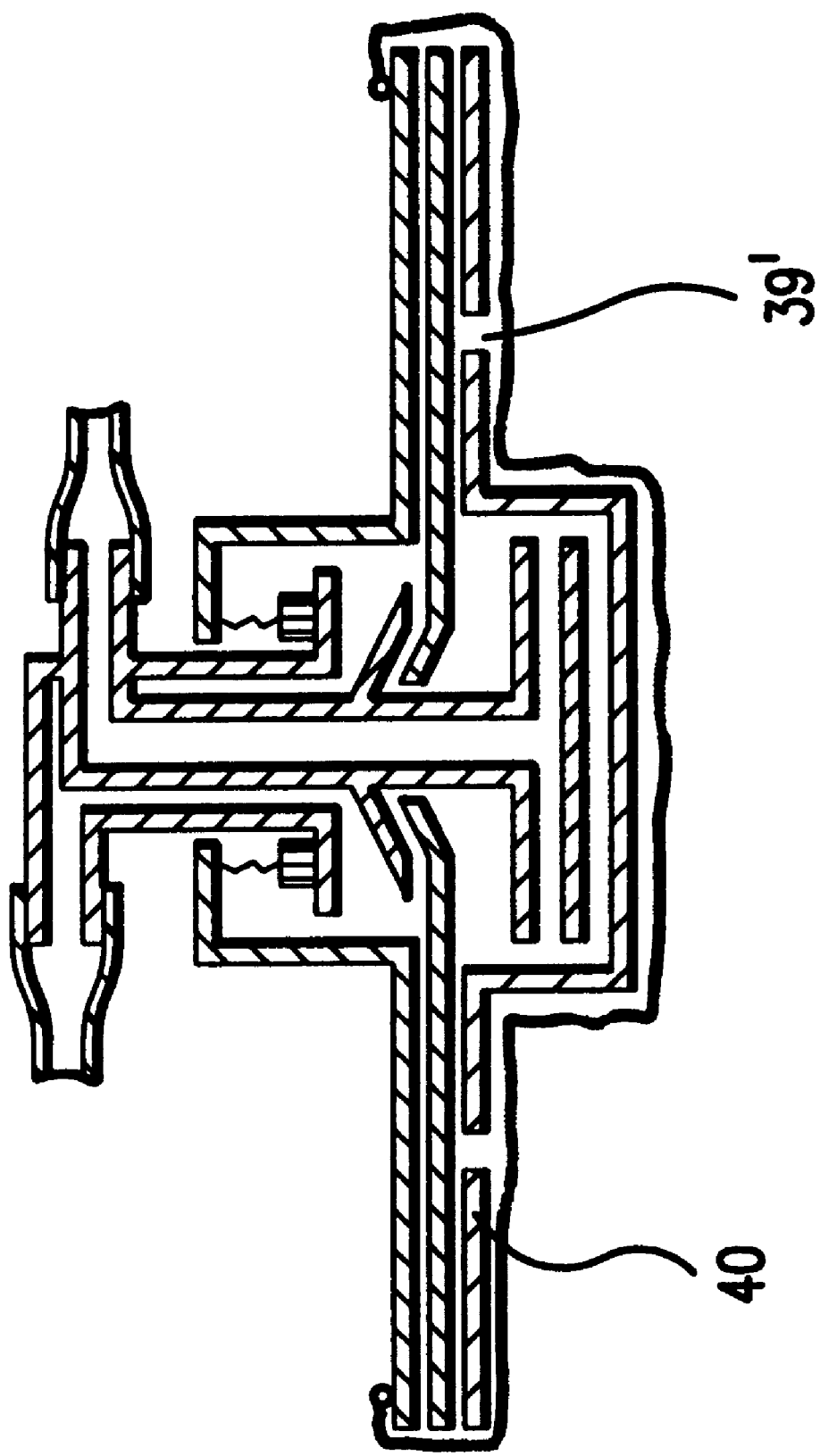
FIGS. 19A–19D show how an alternative rotor may be used to collect platelets.
Figure 19B:
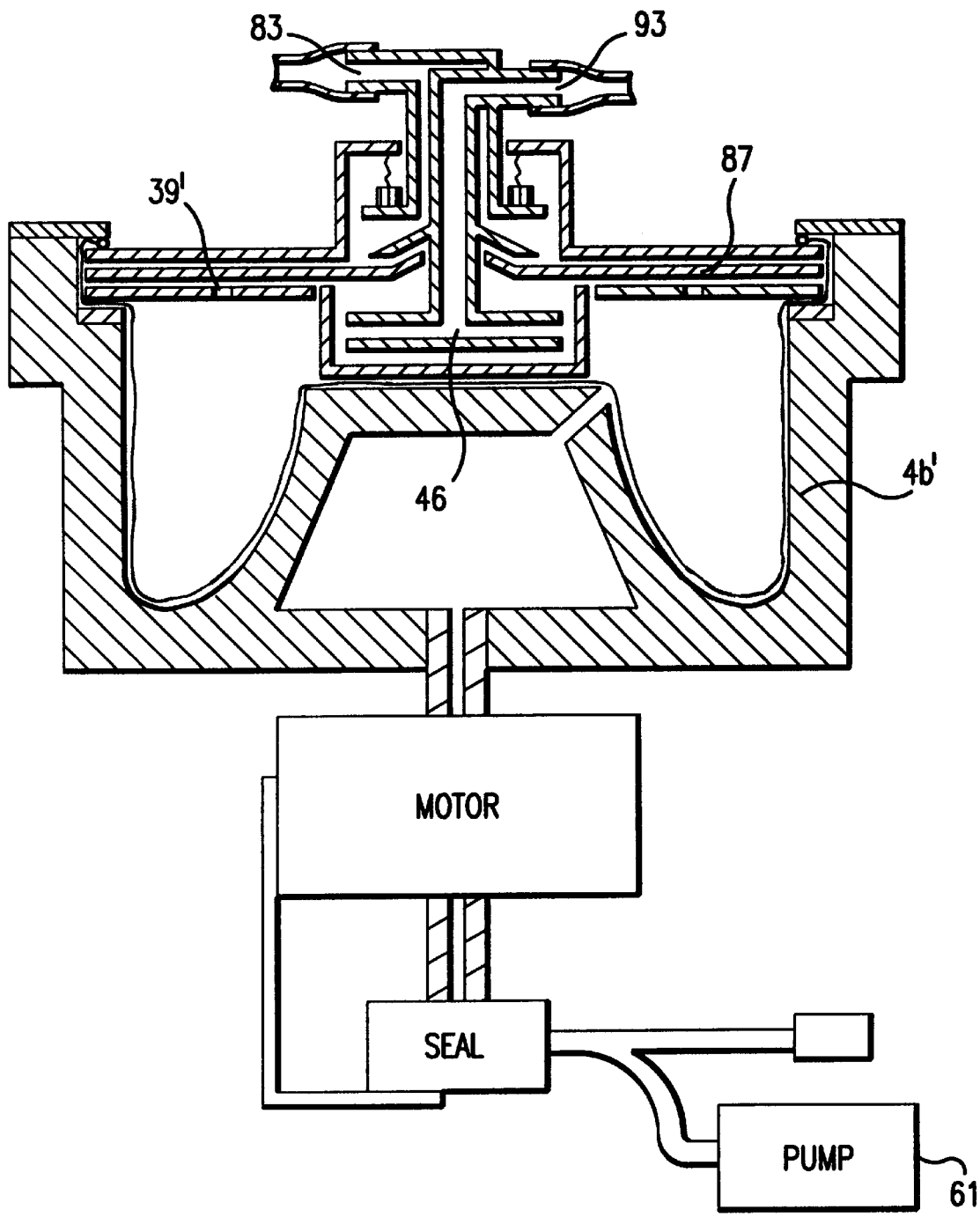

FIG. 19B shows the FIG. 19A rotor mounted in a chuck 4b', which is similar to the chuck shown in FIG. 12. Anticoagulated whole blood may be pumped into the rotor through inlet 83, while the chuck 4b' and the rotor are being spun. Imperforate plate 87 directs the incoming whole blood towards the periphery of the rotor. The rotor is filled with blood, so as to occupy the entire space available in chuck 4b', causing plasma to be forced out of the rotor first, through holes 39'. When a sufficient amount of RBCs is in the rotor, the platelet layer lines up with holes 39'. One way for determining when the platelet layer lines up with holes 39' is an optical detector, which detects the buff color of the platelet layer.

Once the platelet layer is lined up with holes 39', a valve (not shown) connecting the outlet 93 to a platelet-collection bag (also not shown) is opened. Compressor 61 then pumps air into the chuck 4b', causing the platelets to be forced through holes 39'. As some of the platelets are forced out of the rotor, some of the plasma may be able to escape past the platelets through holes 39'. However, the escaping plasma will entrain the platelets nearer the axis of rotation. If the platelet layer begins to move radially outward, away from the axis of rotation and away from holes 39', more whole blood may be added to the rotor so as to reposition the platelet layer directly under the holes 39'.

A significant advantage of this platelet-collection process is that the plasma used to push the platelets out of the rotor comes from the center of the rotor instead of the rotor's periphery. Thus, the plasma pushes out the lightest platelets, which are the youngest platelets and which have the least amount of white blood cells intermixed with them. Prior-art platelet collection processes use fixed-volume rotors and use plasma coming from the periphery of the rotor to push platelets out of the rotor.

Figure 19C:
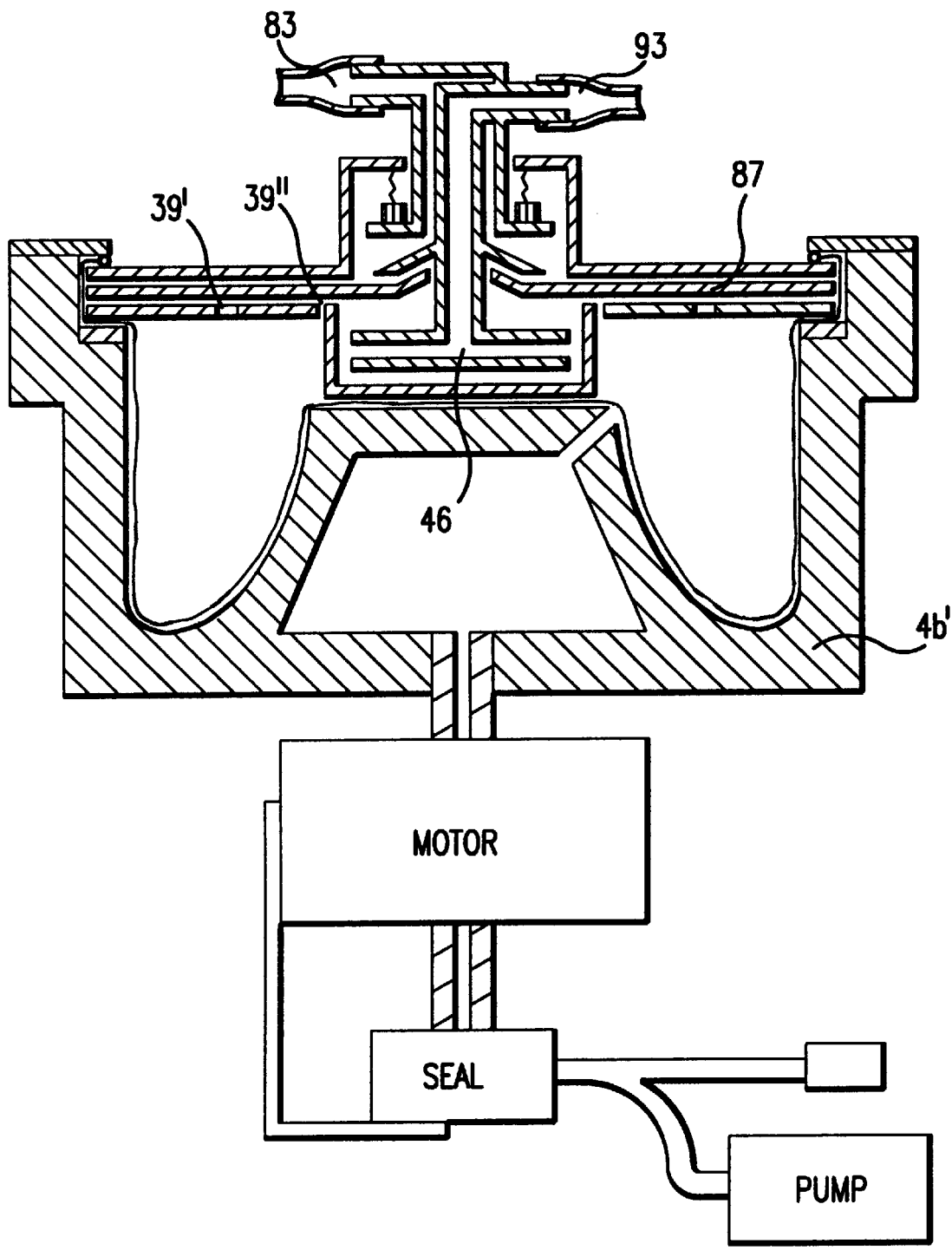

The system shown in FIG. 19C is similar to the system shown in FIG. 19B, except that the rotor has additional holes 39" located at a smaller radius than holes 39'. In using this rotor in the platelet collection process, the plasma flows out of holes 39" as the rotor fills with RBCs. When the platelets are lined up with holes 39', whole blood flow into the rotor is stopped. Air is pumped into the chuck 4b' causing plasma to flow through holes 39" until the diaphragm covers the holes 39". When holes 39" are covered, the platelets, which are lined up with holes 39', are forced out through holes 39'.

Figure 19D:
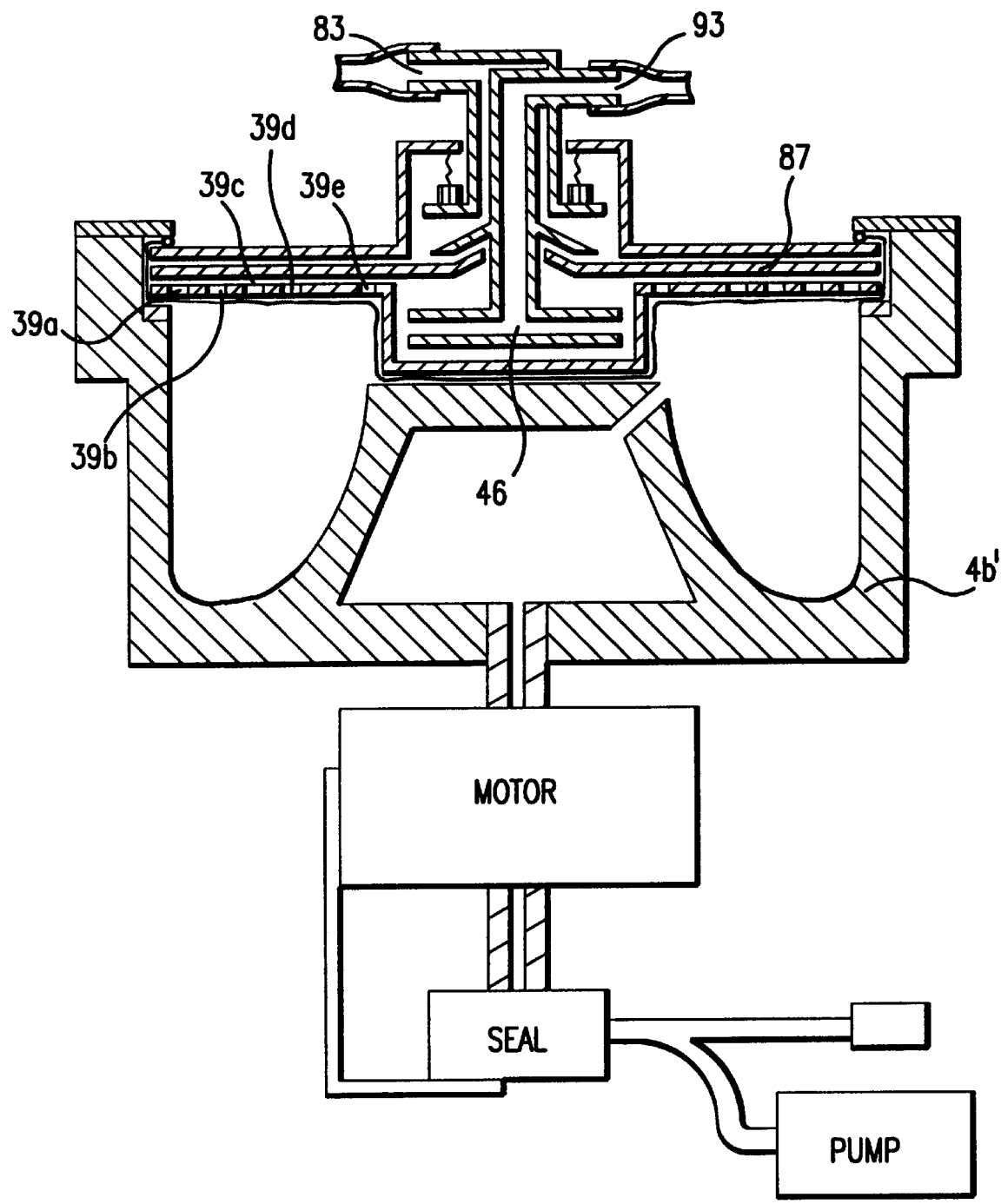

FIG. 19D shows a system that permits platelet collection at various extracorporeal volumes. Sets of holes 39a, 39b, 39c, 39d and 39e are arranged in circles and are spaced by some distances, such as 0.1 to 0.2 inches. There may be more or fewer sets of holes as desired. All of the holes in each set are located at the same radius. Platelets may be collected when there are sufficient RBCs in the rotor to position the platelets at any of the sets of holes.

For example, once the rotor shown in FIG. 19D is filled so that the platelets are located directly under holes 39b, air may be pumped into the chuck 4b' to force the plasma, which is located inside the layer of platelets, out first through holes 39e (assuming that the rotor was completely filled before the platelets became located under holes 39b), then holes 39d and 39c in turn. (The volume of the processing chamber may, of course, be set at less than its maximum volume by maintaining a positive air pressure in the chuck 4b'; in such a case, the plasma would first be forced out through the holes at the smallest radius not covered by the diaphragm.) Once sufficient plasma has been forced out of the rotor so that all the holes located inside of the layer of platelets—holes 39c, 39d and 39e in the example—are covered by the diaphragm, the platelets are forced out of the rotor through holes 39b.

Figure 19E:
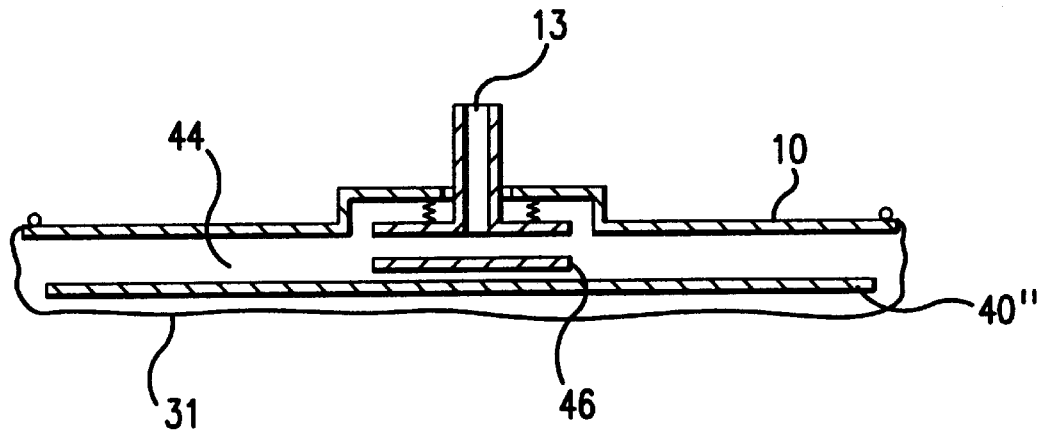
FIG. 19E shows a rotor that may be used to collect the separated fluid component with the greatest density.

FIG. 19E shows a rotor that has as an outlet-control structure an imperforate interior wall 40", instead of a perforate interior wall (like plate 40 discussed above). This rotor has only one conduit 13, which serves both as the inlet and outlet, at different times, to the rotor's processing chamber. This rotor may be used with a chuck, such as that shown in FIG. 3, or with an exterior shell, such as those shown in FIGS. 7 and 8A. Using an imperforate interior wall 40" in this way permits the collection of separated fluid components having the greatest density first, before the collection of intermediate density and lighter density components. After the processing chamber has been filled with desired amount of blood (or other biological fluid) and the blood has been separated, the air pressure against the exterior of the diaphragm 31 is increased or the rotation of the rotor decreased so as to force the concentrated RBCs, which are located furthest away from the rotor's axis of rotation, past the outer edge of the imperforate interior wall 40". Since there may initially be separated blood components in the channel 44 between the boundary wall 10 and the interior wall 40" after separation, there may be a small amount of lighter fluid components exiting the rotor before the concentrated RBCs. After this small amount of lighter blood components—plasma, platelets—are forced out of the channel 44, all the RBCs may be collected before the remaining lighter blood components reach the periphery of the interior wall 40".

Thus, different configurations of the inlet-control and outlet-control structures allow rotors to be optimized for different types of blood-component collection processes, such as plasma collection or platelet collection, or other biological-fluid-component collection processes. In general, the placement of holes in the interior plates and the diameter of the plates can be manipulated in order to accomplish the desired flow patterns out of and/or into the rotor. As is discussed below in connection with FIGS. 30–36, tubes may be used instead of plates (e.g., plates 40, 40', 40", 87, 87', 87a and 87b) to achieve the desired flow patterns into and/or out of the rotor's processing chamber. It will be appreciated that various types of outlet-control structures, including tubes and plates that permit fluid to flow out of the processing chamber at a selected radius or selected radii (like the plates 40 shown in FIGS. 19A–19E), may be used with other types of rotor designs, such as the rotors shown in FIGS. 20 and 23.

For some of the blood-processing procedures which have been discussed in this application, such as post-operative and intraoperative salvage, and RBC and plasma apheresis (see for example the processes represented in FIGS. 6 and 15), it is desirable that the interior plates 40 have holes 39 located at varying and closely spaced distances from the center of the plate 40 to its periphery. This placement of holes 39 ensures that all of a lighter fluid element (e.g., plasma) is forced out of the processing chamber 30, before a heavier fluid element (e.g. RBCs) begins to be forced out.

Figure 20:
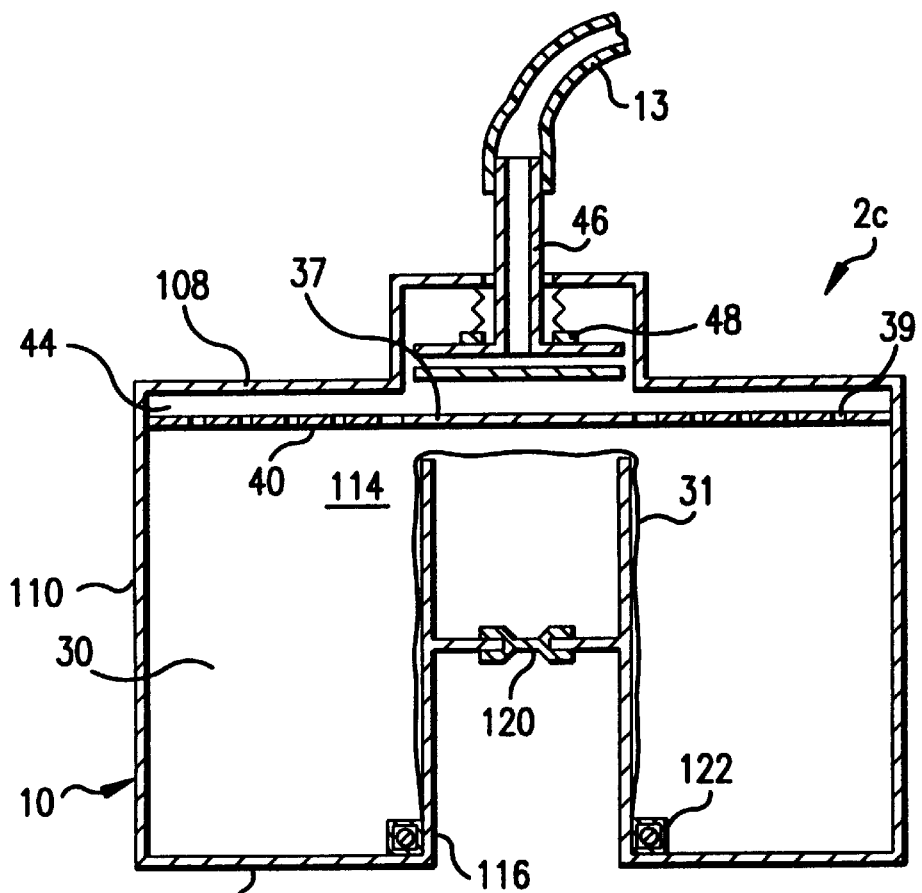
FIG. 20 shows a cross-section of an alternative rotor having a balloon-shaped diaphragm mounted around a core.

FIG. 20 shows an alternative rotor 2c, which may be used in much the same way as the rotor 2a shown in FIG. 2. Like the FIG. 2 rotor 2a, the rotor 2c shown in FIG. 20 allows fluids to flow in or out of the rotor in only one direction at a time. The boundary wall 10 of rotor 2c includes a top portion 108, a circumferential portion 110 and a bottom portion 112, so that the boundary wall 10 forms a shell surrounding the processing chamber 30. Note that the shell formed by the circumferential 110 and bottom 112 portions of the FIG. 20 rotor 2c differ from the exterior shell 3a shown in FIG. 7 and the shell 3b shown in FIG. 8A. The FIGS. 7 and 8A shells 3a and 3b do not directly touch the blood in the processing chamber. The circumferential 110 and bottom 112 portions of wall 10 in FIG. 20 do touch the blood in the processing chamber 30.

The top portion 108, circumferential portion 110 and bottom portion 112 of the boundary wall 10 may be curved, so that the rotor is generally ovoid and the borders between the various wall portions are not distinct. Shaping the boundary wall 10 in this way may reduce the amount of stress on the diaphragm 31 (in much the same way that the shaping of the interior of chuck 4a shown in FIG. 3 reduces stresses in the diaphragm, as discussed above).

The FIG. 20 rotor 2c also includes central core 116. The boundary wall 10 and the core 116 are preferably made of rigid plastic pieces joined together. At the top of the rotor 2c, there is a collector assembly 46 attached to a tube 13 connected to the rest of the disposable blood processing set (e.g., a cassette and additional tubing). The collector assembly 46 also interfaces with a rotary seal 48, like the rotary seals discussed in connection with the FIG. 2 and FIG. 11 rotors 2a, 2b. The rigid core 116 of rotor 2c is covered by an elastic balloon-shaped diaphragm 31, which is held in place with an air-tight seal by a clamp 122. (In alternative embodiments, the diaphragm may be attached to any point on the bottom wall 112, or even to the circumferential wall 110. If the membrane is attached near the top of the circumferential wall, the rotor becomes very similar to the rotor 2a and shell 3b combination of FIG. 8A. In such a rotor, the circumferential and bottom walls would not be considered boundary walls, since they would no longer come into contact with the blood being processed.) Between the diaphragm 31 and the collector assembly 46 is a plate 40. As in the previously discussed rotors 2a, 2b, the plate 40 prevents the diaphragm 31 from touching the collector assembly 46. The plate 40 is held away from the upper part 108 of the boundary wall 10, so as to form a passage 44 between the boundary wall 108 and the plate 40. The plate 40 preferably contains many, preferably small, holes to permit fluid to flow into the passage 44 from almost any point along the plate 40. In a wall within the core 116 separating the core into interior and exterior portions is a pressure-supply port 120, which is blocked by a frangible diaphragm during storage.

Figure 21:
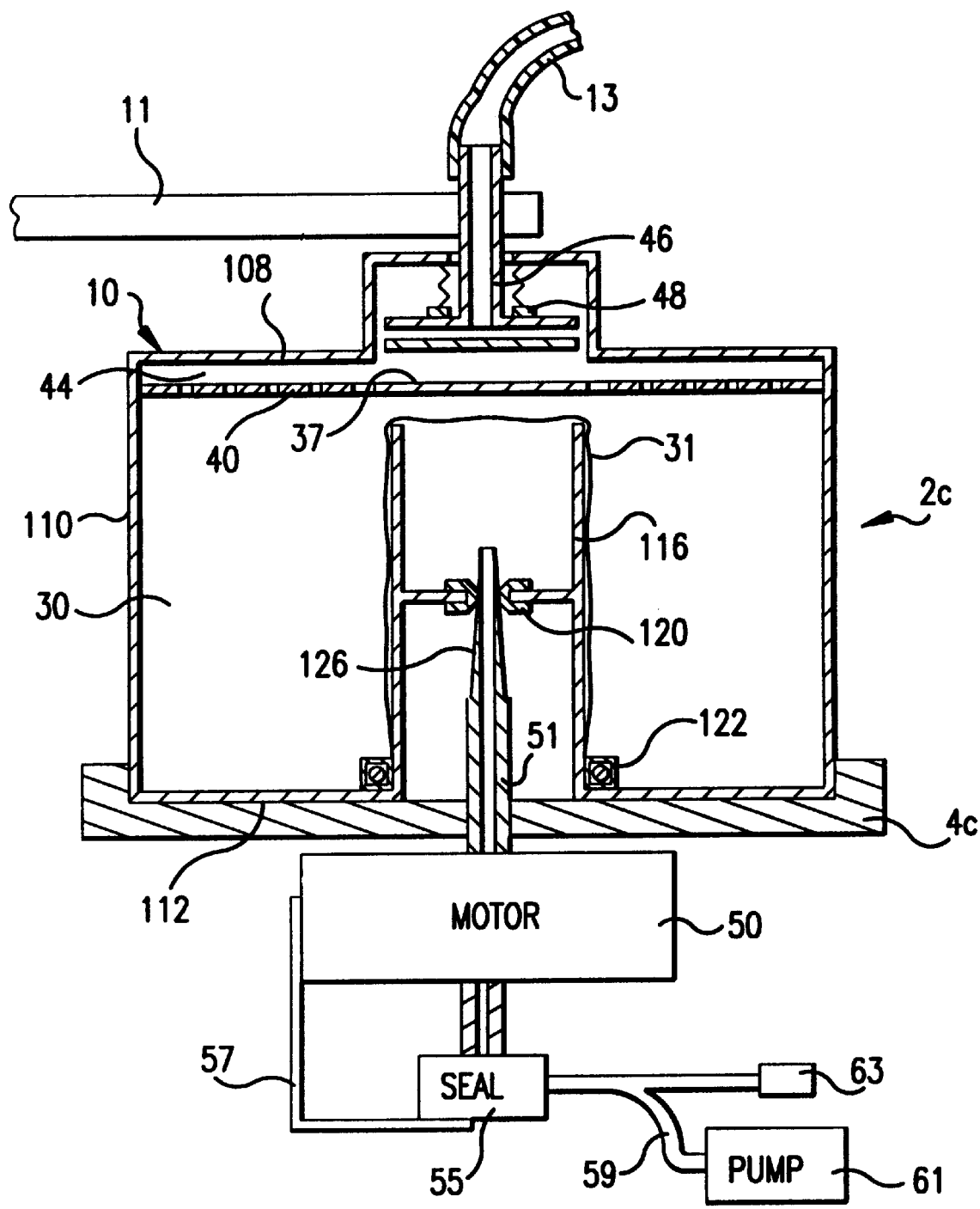
FIG. 21 shows a cross-section of the FIG. 20 rotor mounted in a chuck.

FIG. 21 shows the rotor 2c being held in a chuck 4c, which is turned by a motor 50. As noted above in relation to the rotor/exterior-shell arrangement shown in FIG. 8A, the chuck and motor may be made small enough to fit inside core 116, below pressure-supply port 120; thus the chuck would hold the rotor 2c from inside the core 116 instead of from outside the circumferential wall 110 as shown in FIG. 21. The collector assembly 46 is held stationary and in the proper alignment by brace 11. The shaft 51 projects up past the chuck 4c and narrows into a thinner section 126 (a nozzle), which penetrates the frangible diaphragm on the pressure-supply port 120 and makes an airtight seal. The shaft 51 has an axial through hole and protrudes below the motor 50. A rotary pneumatic seal 55 is attached to the shaft 51 and is held stationary by fixture 57. The pneumatic rotary seal 55 is connected by tubing 59 to the compressor/vacuum-source 61 and to a controllable exhaust valve 63.

Figure 22:
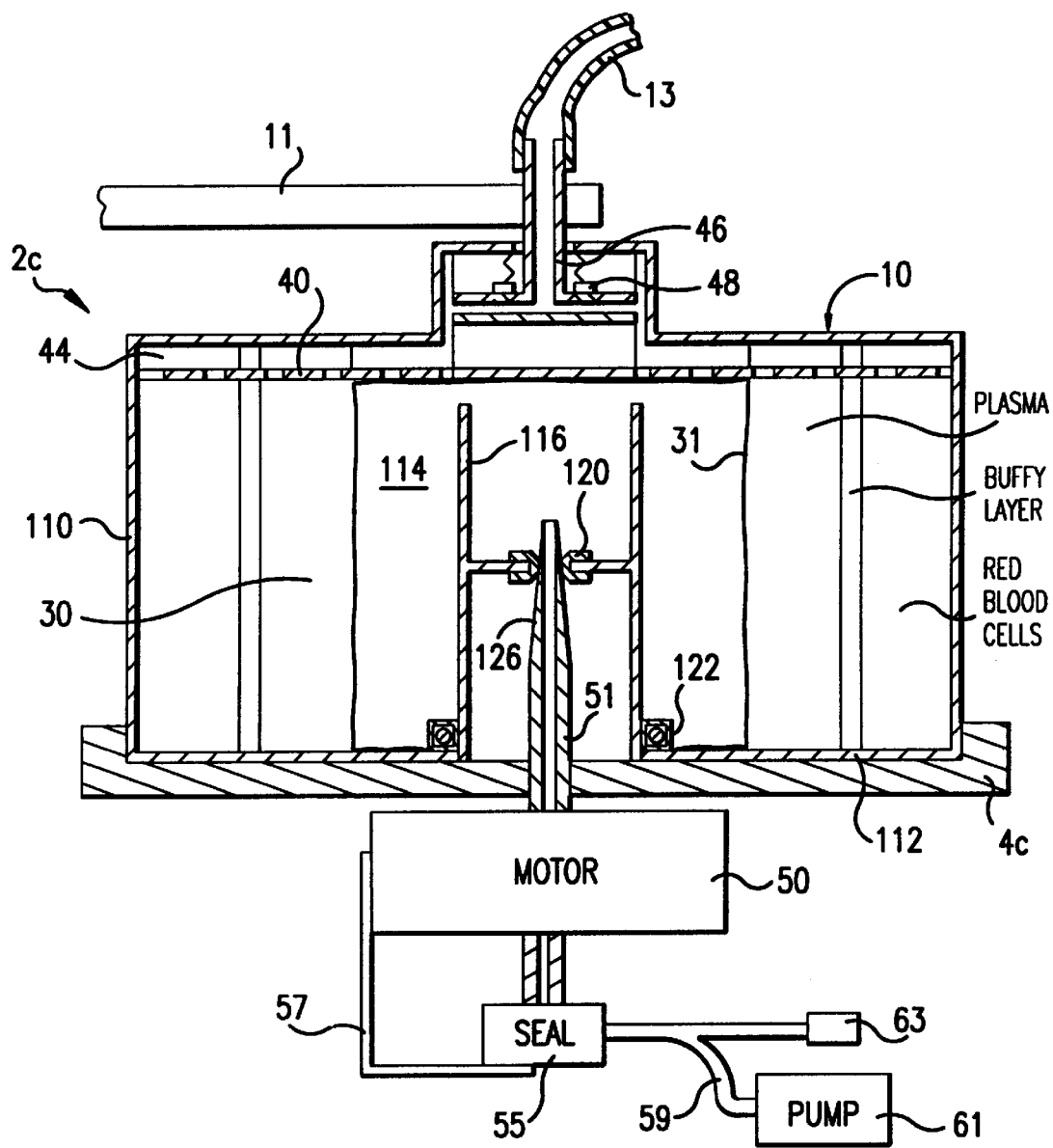
FIG. 22 shows a cross-section of the FIG. 21 system centrifuging blood.

FIG. 22 shows the rotor 2c spinning and partially full. In operation, the motor 50 spins the rotor 2c. The diaphragm 31 is inflated by the compressor 61 until it fully occupies the cavity 114 defined by the plate 40, the core 116 and the boundary wall's circumferential 110 and bottom 112 portions. The inflated diaphragm 31 thus expels all of the air previously in the cavity 114 into the passage 44 and collector assembly 46 and on through a filter in the disposable set out to the room atmosphere. This reduces to its minimum the volume of the processing chamber 30, which is defined by the boundary wall 10 and the diaphragm 31. Donor blood, shed blood or another type of biological fluid then is allowed to flow into the rotor from the rest of the disposable set through tube 13 and collector assembly 46. The blood is propelled by centrifugal force towards the perimeter of the rotor 2c. As more blood enters, it continues to be propelled to the perimeter eventually flowing through the holes in the plate into the cavity 114 defined by the boundary wall 10, the core 116 and the plate 40, thereby increasing the volume of the processing chamber 30. As blood enters the processing chamber 30, the diaphragm 31 slowly collapses around the core 116, and the air between the diaphragm 31 and the core 116 is allowed to escape through exhaust valve 63.

Blood flow into the rotor 2c is stopped when the desired or available amount of blood has entered the rotor 2c or when the cavity 114 is full. The blood is subjected to the centrifugal force as long as is appropriate to separate the various components. When the separation is complete, the compressor 61 begins to re-inflate the diaphragm 31.

The manner of processing blood in the FIG. 20 rotor 2c is very similar to that of the FIG. 2 rotor 2a. When the air pressure acting on the side of the diaphragm 31 opposite the blood exceeds the pressure from the radius of the diaphragm 31 to the skirt of the collector assembly 46, fluid begins to flow from the cavity 114 through the holes in the plate 40, into the passage 44 to the collector assembly 46 and out of the rotor 2c into the rest of the processing set. This fluid may be diverted to a specific container or returned to a donor depending on the intention of the process and the specifics of the processing set. The blood element with the lightest specific gravity first flows out of the cavity 114 through the holes in the plate at the smallest radius not yet covered by the diaphragm 31. Each blood element in turn by specific gravity will flow out of the rotor 2c and can be diverted as desired. The process of emptying the rotor 2c can be stopped at any time by stopping the compressor 61 from increasing the air pressure on the diaphragm 31 (while keeping the chuck's rotational speed constant).

If the rotor 2c is processing blood, one likely place to stop might be when the diaphragm 31 touches the RBC layer and another might be when the rotor 2c is empty. As noted with the FIG. 2 rotor 2a, this cycle can be repeated as desired or, if washing of the blood components left in the rotor 2c is desired, other fluids can be allowed to flow into the rotor 2c and back out again by inflating or deflating the diaphragm 31 and manipulating valves and/or tubes in the processing set. At the end of the last cycle, the diaphragm 31 can be inflated to the proper position to obtain the desired hematocrit in the final product. As noted above, it may be desirable to change the rotor speed at different times while the rotor 2c is filling or emptying in order to achieve the most advantageous combination of centrifugal force for separation and air pressure inside the diaphragm 31 required to overcome the current fluid head.

The core 116 of the FIG. 20 rotor 2c serves a similar purpose to the chuck core 64 of the chuck 4a shown in FIGS. 3–4, 9 and 12–13. The core 116 helps shape the diaphragm 31 when the processing chamber 30 is at its largest volume (which in the FIG. 20 rotor 2c is when the diaphragm 31 is its relaxed position, unlike the FIG. 2 rotor 2a, in which the diaphragm is in its relaxed position when the processing chamber 30 is at its lowest volume). The core 116 ensures that, when the processing chamber 30 is at its largest volume, there are holes 39 located at the innermost radius of the processing chamber 30. (It will be appreciated that by shaping the core 116 so that the top of the core 116 covers the plate's center 37, and so that the diameter of the top of the core 116 is not greater than the diameter at any other point of the core 116, one can ensure that all of the lighter fluid elements can be emptied out of the rotor 2c first, even when the processing chamber 30 is at the greatest volume permitted by the boundary wall 10 and the core 116 of the FIG. 20 rotor 2c.)

Figure 23:
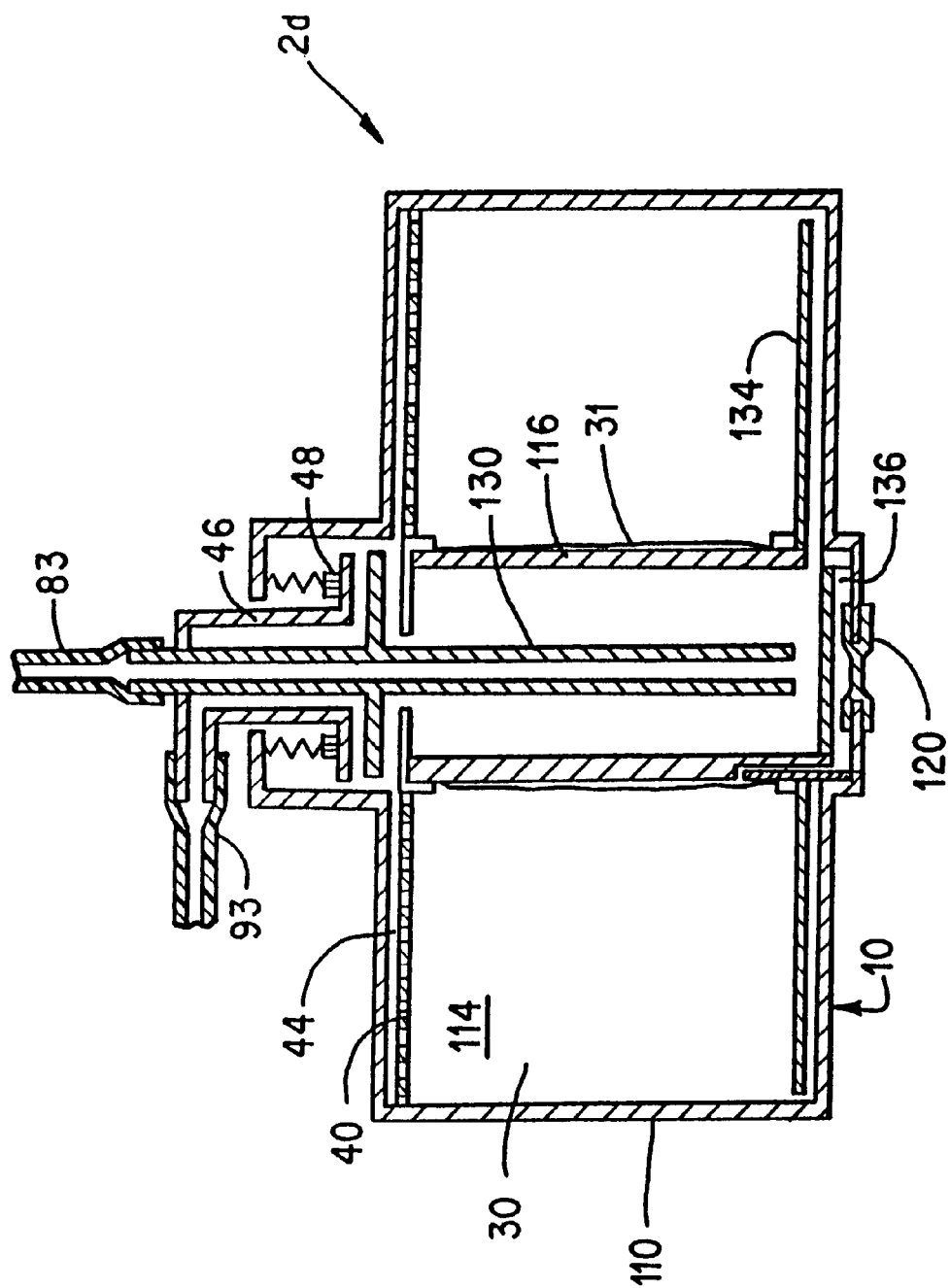
FIG. 23 shows a cross-section of an alternative two-conduit rotor.

FIG. 23 shows an alternative rotor 2d, which can be used in much the same way as the rotor 2b shown in FIG. 11. Like the FIG. 11 rotor 2b, the rotor 2d shown in FIG. 23 permits fluids to flow in and out of the rotor at the same time. The rotor 2d, like the FIG. 20 rotor 2c, has a boundary wall 10 that surrounds the processing chamber 30 and that is preferably made of rigid plastic pieces joined together. At the top of the rotor 2d, there is a collector assembly 46 attached to tubes 83, 93 connected to the rest of the processing set. The collector assembly 46 interfaces with a rotary seal 48. The passage between the skirts of the collector assembly 46 connect with tube 93. The fixed portion of rotor 2d has an extension tube 130, which connects tube 83 with the bottom of the rotor 2d. The rigid core 116 is covered by a sleeve-shaped elastic diaphragm 31, which is held in place with a air-tight seal by the inner portion of a lower, imperforate interior wall 134 and the inner portion of the (upper) plate 40. The lower interior wall 134 is shown in FIG. 23 as extending to the periphery of the cavity 114, but in an alternative embodiment, a smaller-diameter lower interior wall 134 may be used, or the lower interior wall may be left out entirely except for the inner ring portion that is used to clamp the bottom of the diaphragm 31, or a perforate plate, like item 134' in FIG. 24, may be used.

The rigid core 116 is attached to the air-introduction area 136 and has one or more generally vertical holes in it that act as air conduits from the air-introduction area 136 to the space between the diaphragm 31 and the rigid core 116. There are gaps in the rigid core 116 below the lower interior wall 134 and above the air-introduction area 136 that allow blood to flow from the extension tube 130 towards the perimeter of the rotor 2d. The outer wall of the air-introduction area 136 has a pressure-source port 120 covered with a frangible diaphragm.

Figure 25:
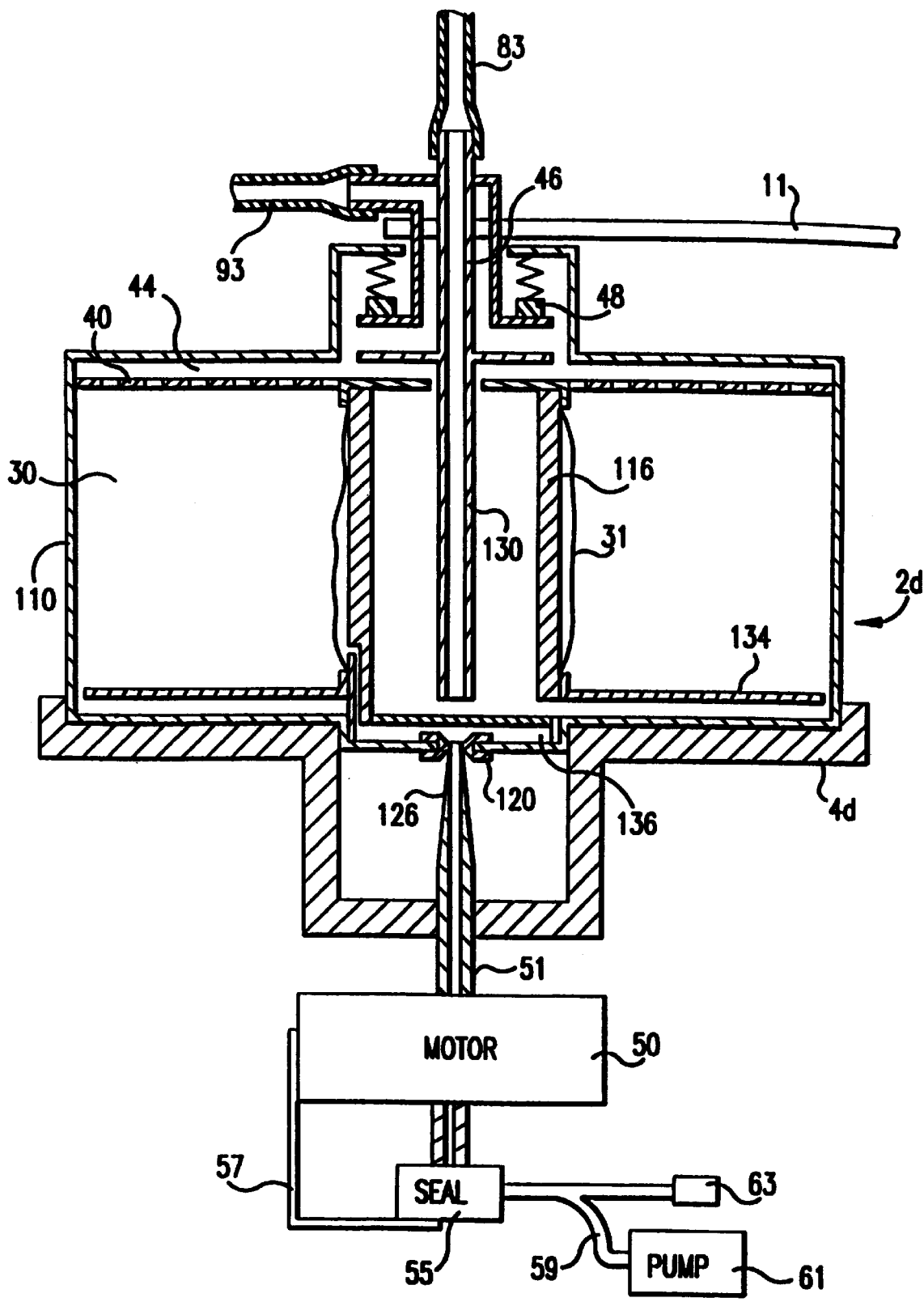
FIG. 25 shows cross-section of the FIG. 24 rotor mounted in a chuck.

FIG. 25 shows the rotor 2d being held in a chuck 4d. The collector assembly 46 is held stationary and in proper alignment by brace 11. The shaft 51 projects up past the chuck 4d and narrows into a thinner section 126, which penetrates the frangible diaphragm covering the pressure-source port 120 and makes an airtight seal with the port 120.

Figure 26:
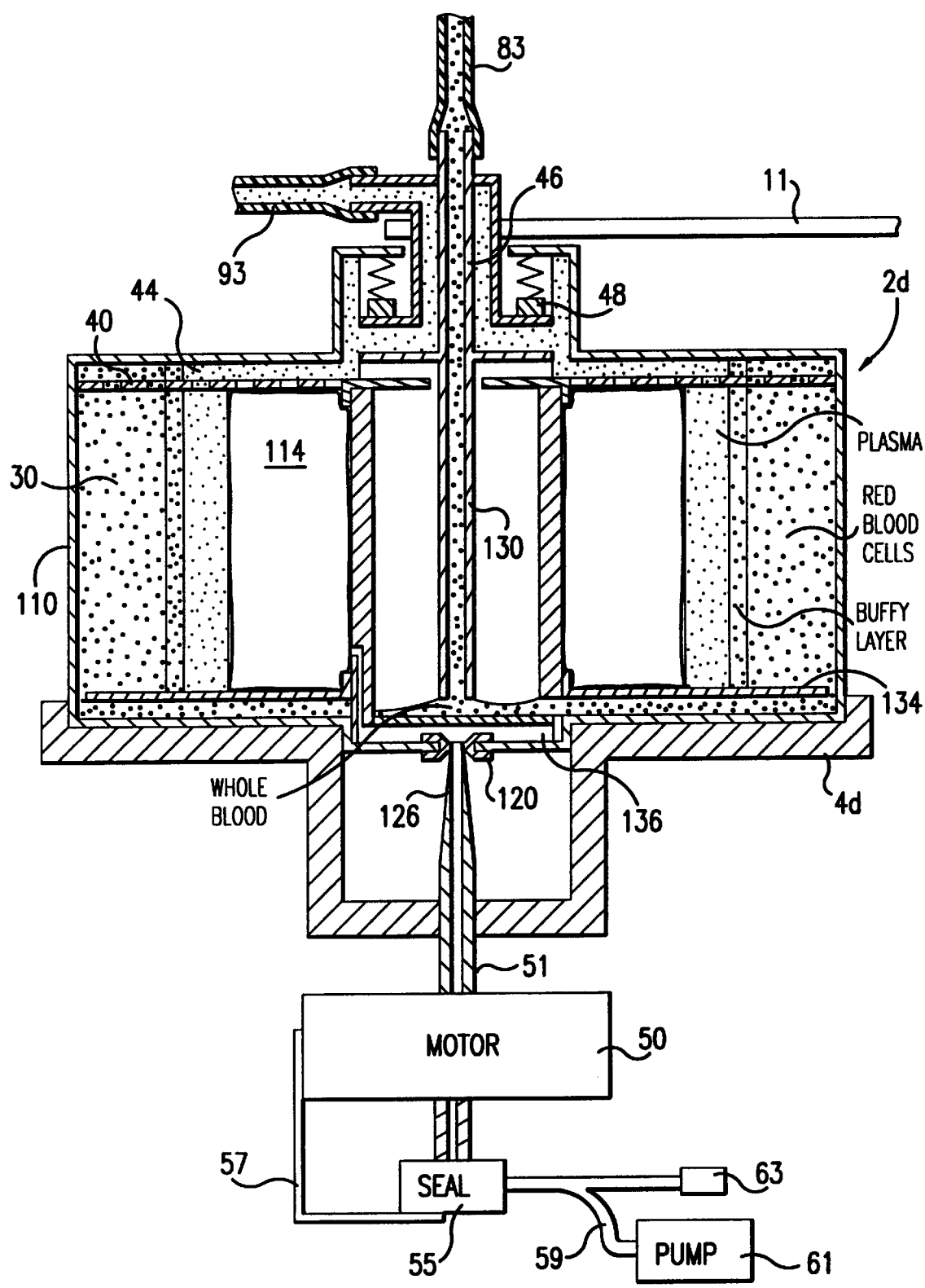
FIG. 26 shows a cross-section of the FIG. 25 system centrifuging blood.

FIG. 26 shows the rotor 2d spinning and partially filled with fluid and with the diaphragm 31 partially inflated. The motor 50 spins the rotor 2d at the proper rate. The process may be started with the diaphragm 31 deflated. Blood or other fluid flows into the rotor 2d from the rest of the processing set through tube 83 and extension tube 130. When the blood touches the bottom of the rotor 2d it is propelled by centrifugal force towards the perimeter of the rotor 2d and into the processing area. As blood enters the rotor 2d, the air in the processing chamber 30 exits through the collector assembly 46 and tube 93 to a holding container in the processing set.

If it is not desired to process a full rotor of blood, the diaphragm 31 can be inflated by compressor 61 when the desired volume of blood has entered the rotor 2d. The diaphragm 31 is inflated until it fills the unwanted rotor volume 138. Operation of the rotor 2d can then continue as normal but with a smaller-volume processing chamber 30.

When the processing chamber 30 is full of blood (with or without the diaphragm 31 inflated), the flow of blood into the rotor can continue through tube 83 and extension tube 130. This new blood simply displaces the elements of blood in the processing chamber 30 with the lowest specific gravity. The elements with the lower specific gravity flow out through the collector assembly 46 and tube 93 to be diverted as desired by the processing set.

The extension tube 130, like the interior imperforate plate 87 of the FIG. 11 rotor 2b, introduces the unprocessed whole blood into the processing chamber 30 at a point spaced away from where the separated blood components exit the chamber 30. If the unprocessed whole blood was introduced into the chamber 30 at a point too close to the point where the separated blood components exit the chamber 30, some unseparated whole blood may be drawn out of the chamber 30 with the separated blood components.

In order to wash RBCs, wash solution may be introduced through tube 83 and extension tube 130. At the end of the process, the diaphragm 31 can be further inflated to push out remaining wash fluid thereby increasing the hematocrit of the final product.

Figure 27:
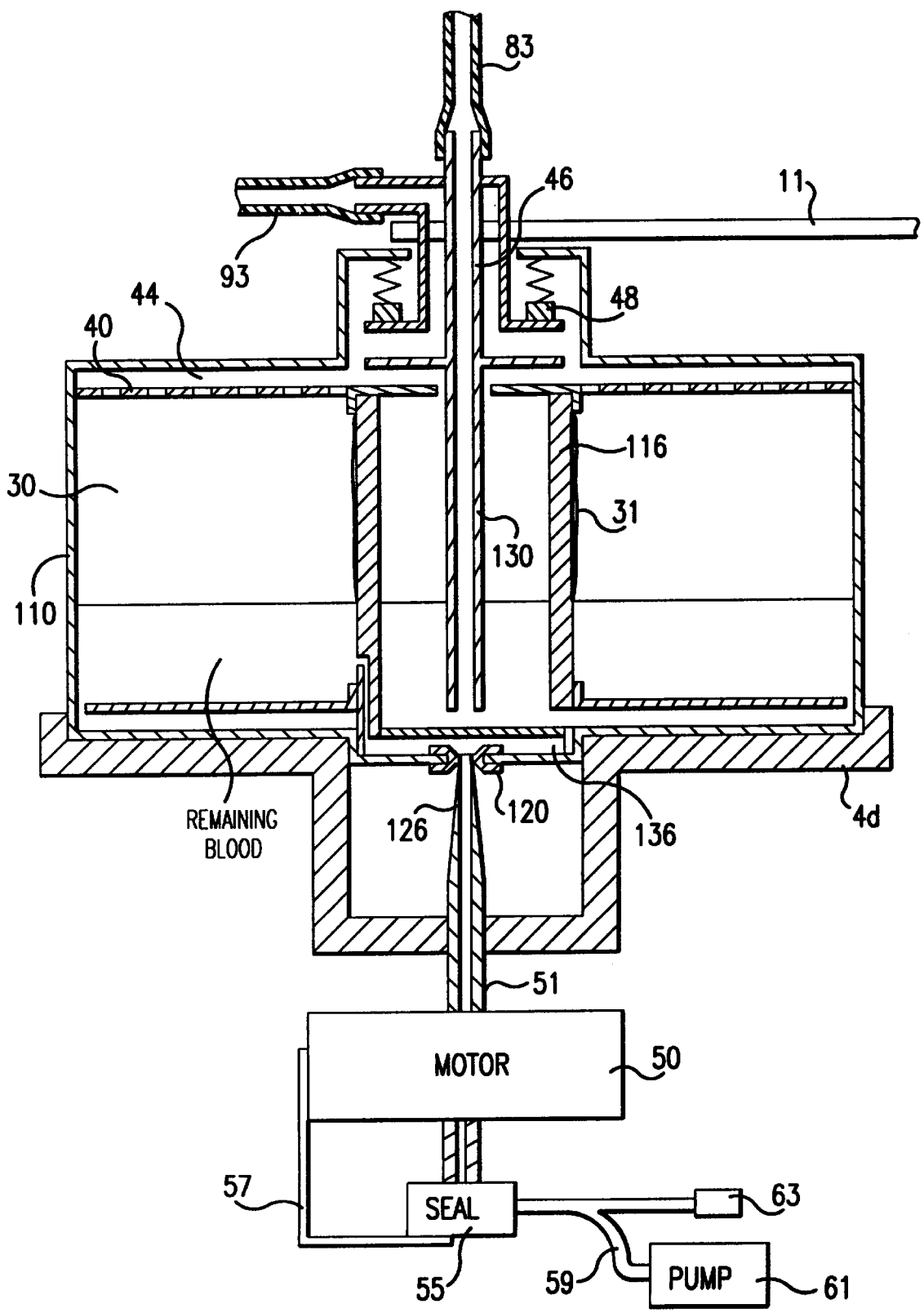
FIG. 27 shows a cross-section of the FIG. 25 system after centrifuging blood.

At the end of the cycle, the air between the diaphragm 31 and the core 116 is vented to exhaust valve 63 and the rotor 2d is stopped. As shown in FIG. 27, the blood remaining in the processing chamber 30 falls to the bottom of the rotor 2d and is pumped out through the extension tube 130 and tube 83 and replaced by the previously collected air.

This cycle may be repeated as desired. As discussed above in connection with the other rotors, it may be desirable to change the rotor speed at different times in order to achieve the most advantageous combination of centrifugal force for separation and air pressure inside the elastic wall member required to overcome the current fluid head.

Figure 24:
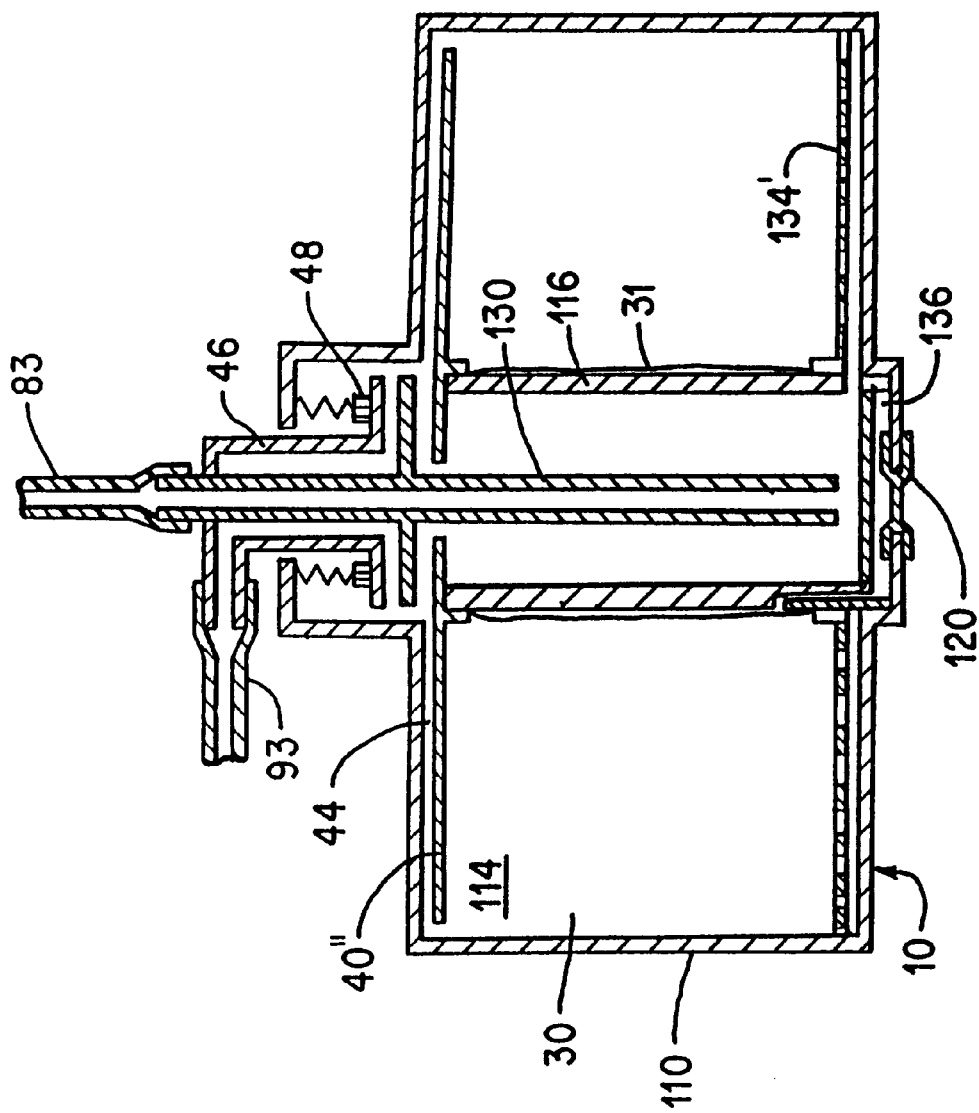
FIG. 24 shows a cross-section of a modified version of the FIG. 23 rotor.

In the modified version of the FIG. 23 rotor shown in FIG. 24, the imperforate interior plate 40" may be substantially imperforate so that fluid can only exit the processing chamber 30, 114 at the periphery of the chamber. The lower interior wall may be perforate. Whole blood may be introduced into the processing chamber through an extension tube, so that the whole blood emerges into the processing chamber near the rotor's axis of rotation. Concentrated RBCs may be collected from the periphery of the processing chamber. The plate 40" of the FIG. 24 rotor may be modified so that intermediate-density blood components, e.g., platelets, may be collected. (See the discussion above regarding FIGS. 19A–19D.)

Figure 28:
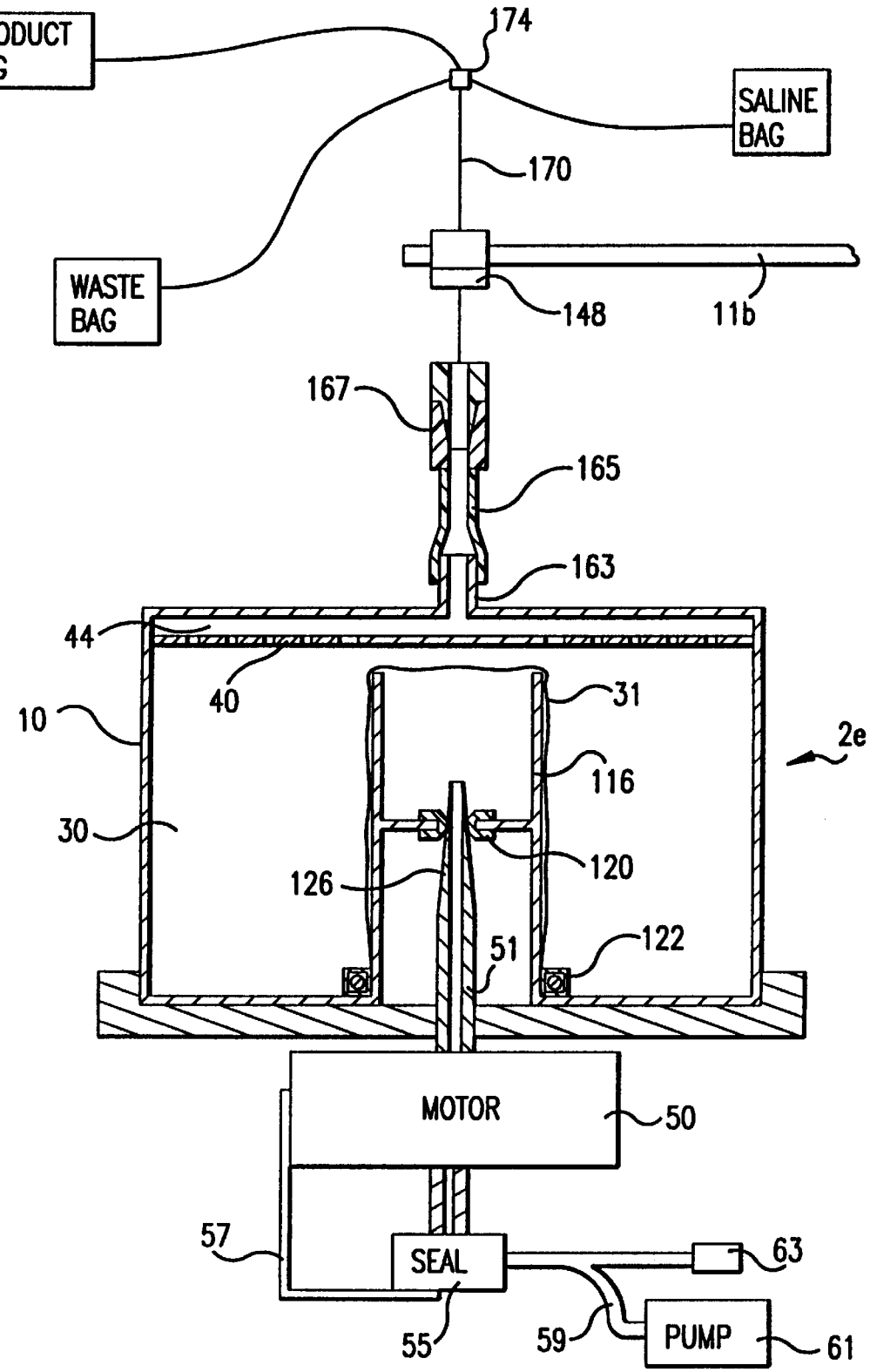
FIG. 28 is a schematic showing how an alternative rotor may be used to process blood.

FIG. 28 shows a rotor 2e having a central port 163 that rotates with the body of the rotor during centrifugation. The rotor 2e can serve both as the reservoir for collecting the blood collected by vacuum (e.g., from a wound drain, i.e., post-operative salvage) and as the centrifugal processing chamber. The rotor 2e consists of a rigid boundary wall 10 and central core 116 made of rigid plastic pieces joined together. In the center at the top of the rotor 2e, there is a port 163 attached to a tube 165 which terminates in a luer-type connector 167. The rigid core 116 is covered by an elastic balloon-shaped diaphragm 31, which is held in place with an air-tight seal by a clamp 122. Between the diaphragm 31 and the central port 163 is a plate 40. In the wall separating the inner and outer portions of the core 116 is a pressure-source port 120 covered with a frangible member. The pressure-source port 120 may be used to connect the rotor to a vacuum source, so that a vacuum may be applied to the diaphragm during the collection of blood. Pressurized gas may also be applied to the diaphragm through the pressure-source port 120 so as to force blood components out of the rotor.

Once the desired amount of blood has been collected in rotor 2e, the vacuum pulling the blood into the rotor 2e is discontinued, and the collected blood may then be processed. The rest of a disposable processing set, such as that shown in FIG. 28, may be connected to the rotor's connector 167. For washing or concentrating the collected blood, the rotor 2e is placed in a chuck as shown in FIG. 28. As with the chuck 4c shown in FIG. 21, a thin section 126 of the shaft 51 penetrates the frangible member on the rotor's pressure-source port 120 and makes an airtight seal with the port 120.

In a variation of the systems discussed above (such as the systems shown in FIGS. 5 and 14), the tubing 170 leading from the rotor 2e may contain the rotary seal 148, instead of a rotary seal being incorporated into the rotor. Alternatively, a skip-rope system, such as those described in U.S. Pat. Nos. 4,151,844 to Cullis et al., 4,283,004 to Lamadrid, 4,734,089 to Cullis, and 4,900,298 to Langley, may be used. (A skip-rope system has the effect of untwisting the tubing connected to the rotor as the tubing is being twisted by the spinning rotor. The skip-rope system results in the tubing having net zero twist, and thus the tubing can be directly attached to both the spinning rotor and the stationary portion of the processing set.)

The tubing 170 in the disposable processing set shown in FIG. 28 branches into three tubes, one of which leads to a bag of saline (which is the wash solution), while another tube leads to the waste bag and the third tube leads to the product bag (where the processed cells are stored). The rotary seal 148 is held stationary and in proper alignment by fixture 11b. (Since the rotary seal 148 is separated from the body of the rotor 2e by tube 165, the outlet-control plate 40 in this rotor 2e does not serve the purpose of protecting the diaphragm 31 from being abraded by a nonrotating portion of the rotor. The plate 40 still serves the purpose of ensuring the proper flow of the separated fluid elements out of the rotor 2e when the rotor is being emptied.) To process the blood in the rotor 2e, the motor 50 spins the chuck and rotor 2e. When separation of the blood components is complete, the compressor 61 begins to inflate the diaphragm 31, so as to cause the fluid to flow through the holes in the plate 40, through the passage 44 and out of the rotor 2e into the rest of the disposable processing set. The blood element with the lightest specific gravity (the plasma, irrigation fluid, anticoagulant, etc.) is forced out of the rotor first and may be diverted to the waste bag by a valve 174. Typically, the process of emptying will be stopped when the diaphragm 31 touches the RBC layer.

At this time, if the user wants to wash the RBCs before concentrating them, the speed of rotation of motor 50 and rotor 2e is reduced to a slow speed. Saline from the saline bag is directed by valve 174 into the rotor 2e. When the rotor 2e is sufficiently full of the saline wash solution, the motor 50 alternately goes forward and backwards to mix the wash solution and the cells. After sufficient mixing, the motor 50 goes forward and gains speed up to its processing speed. In a manner similar to that described above, once the blood is fully separated, the diaphragm 31 is inflated, pushing the used wash solution out into the waste bag. When the diaphragm 31 touches the RBC layer or when sufficient wash solution has been removed to reach the desired final hematocrit, the final emptying process begins. As RBCs emerge from the rotor 2e, they are diverted by valve 174 to the product bag. This process continues until the rotor 2e is empty.

If the user does not want to wash the blood collected in the rotor, the steps of introducing saline into the rotor 2e, washing the cells, centrifuging and forcing out the used saline may be omitted. As with the processes previously discussed, it may be desirable to change the rotational speed at different times while the rotor is emptying in order to achieve the most advantageous combination of centrifugal force for separation and air pressure on the diaphragm 31 to overcome the current fluid head.

Figure 29:
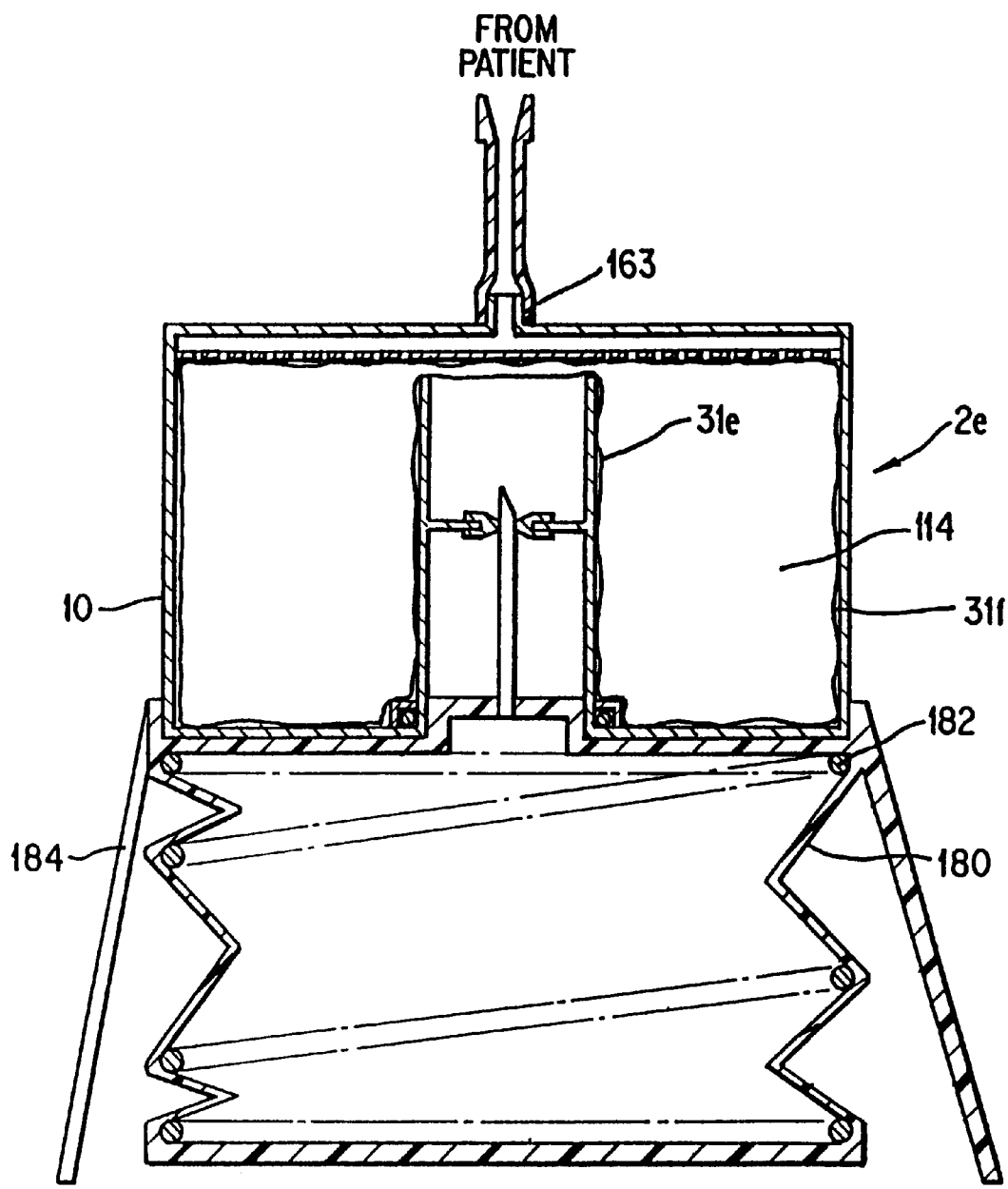
FIG. 29 is a cross-section of the rotor shown in FIG. 28 and a portable device for applying a vacuum.

In order to draw fluid into the rotor 2e, the elastic diaphragm may be used to create the vacuum. Prior to attaching the port 163 to the tubing leading to the patient, the diaphragm is inflated by a source of compressed air, such as pump 61. (FIG. 29 shows the diaphragm in its relaxed position 31e and in its inflated position 31f.) A compressor may be used to inflate the diaphragm to position 31f, and the air in the interior of the rotor 2e is vented to atmosphere through port 163. After the diaphragm 31 is inflated to its maximum diameter, port 163 is attached by means of a tube to a patient, and the compressor 61 is turned off. The air on the core 116 side of the diaphram 31 is vented to atmosphere—through vent 63, if the rotor is mounted in a chuck as shown in FIG. 28. The vacuum caused by the stretched, resilient diaphragm (shown by line 31f in FIG. 29) trying to resume its natural shape (shown by line 31e in FIG. 29) causes blood to flow from the patient into the rotor 2e.

After a vacuum has been pulled on the diaphragm, the vacuum source can be turned off or even disconnected until sufficient blood has flowed into the rotor to reduce the vacuum below an acceptable level. This would allow the patient to be transported (for example between the operating room and the recovery room) without being attached to a vacuum source.

FIG. 29 shows an inexpensive and simple means of providing compressed air to inflate the diaphragm and a vacuum to assist deflating it. The rotor 2e is attached to spring bellows 180 which incorporates a calibrated spring 182. The bellows 180 and the rotor 2e are supported by legs 184. To inflate the diaphragm 31e, the operator squeezes the spring bellows 180. After the patient is connected to port 163 of rotor 2e, the operator allows the spring bellows 180 to re-expand under the force of the spring 182 thereby creating the vacuum assist for the inflated diaphragm 31f for pulling blood into the rotor 2e from the patient.

The rotor 2c shown in FIG. 20 can also be used to collect blood from a wound drain, in much the same way as the rotor 2e of FIGS. 28 and 29. A spring bellows similar to the one shown in FIG. 29 can also be adapted for providing a vacuum to the diaphragm of the rotors 2a of FIG. 2, or for supplementing the vacuum in the rotor/shell combinations shown in FIGS. 7 and 8A.

Figure 30:
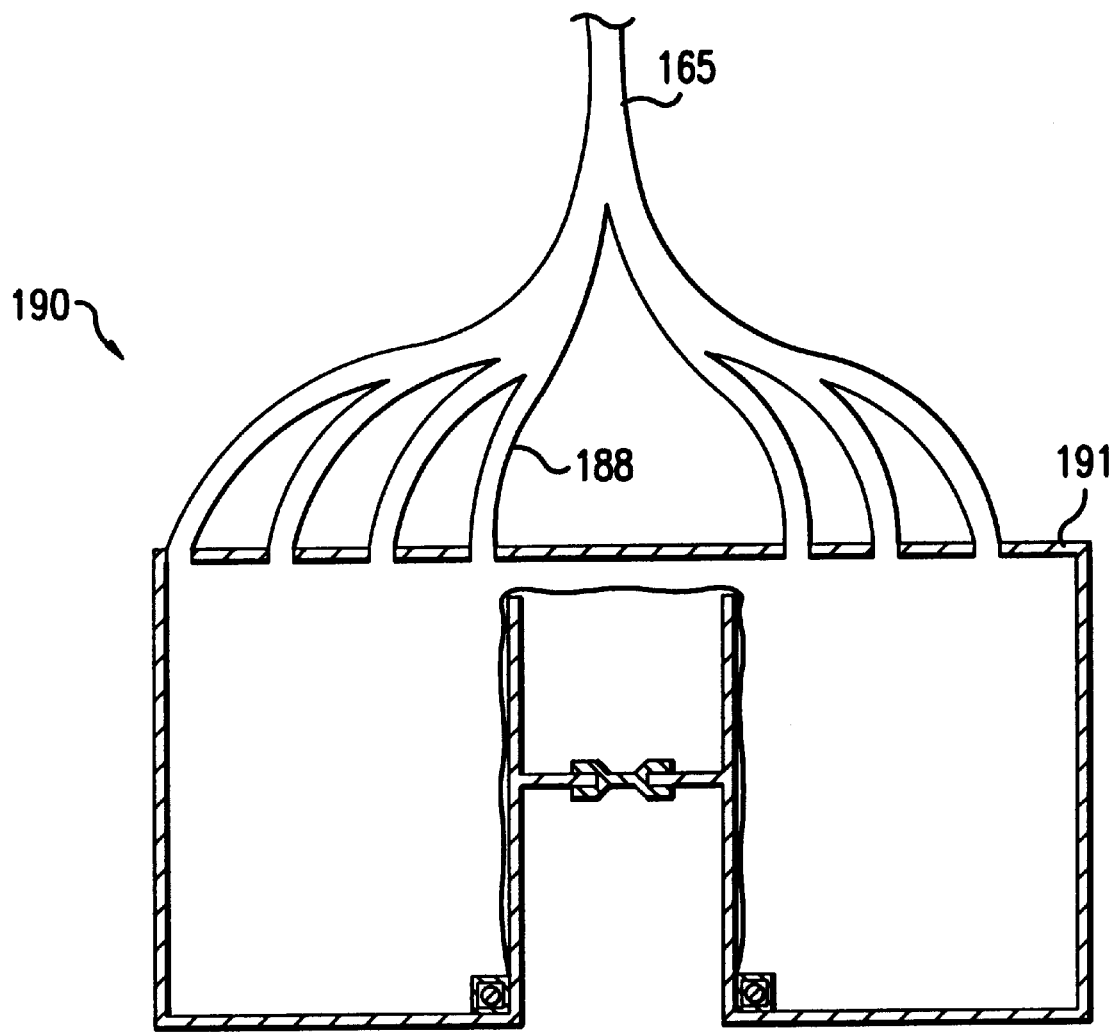
FIG. 30 shows an alternative rotor having a set of tubes, in lieu of a perforate interior wall, for controlling the flow from the processing chamber.

FIG. 30 shows an alternative rotor according to the present invention using a set of tubes 190 extending from the top wall 191 of the rotor. This rotor, unlike all of the previously discussed rotors, does not have an interior wall—i.e., a wall (plate) both sides of which come into contact with the blood or other biological fluid being processed. The set of tubes 190 all join together into a common tube 165, through which fluid both enters and exits the rotor. When this rotor is emptied, fluid first exits the innermost tube or tubes not covered by the diaphragm. Thus, if the processing chamber is at its maximum volume, the innermost tube or tubes 188 provide the first pathway for the exiting fluid. The common tube 165 may be attached to the rest of the processing set (which of course does not rotate) by means of a rotary seal, such as the rotary seal 148 shown in FIG. 28, or a skip-rope system.

Figure 31:
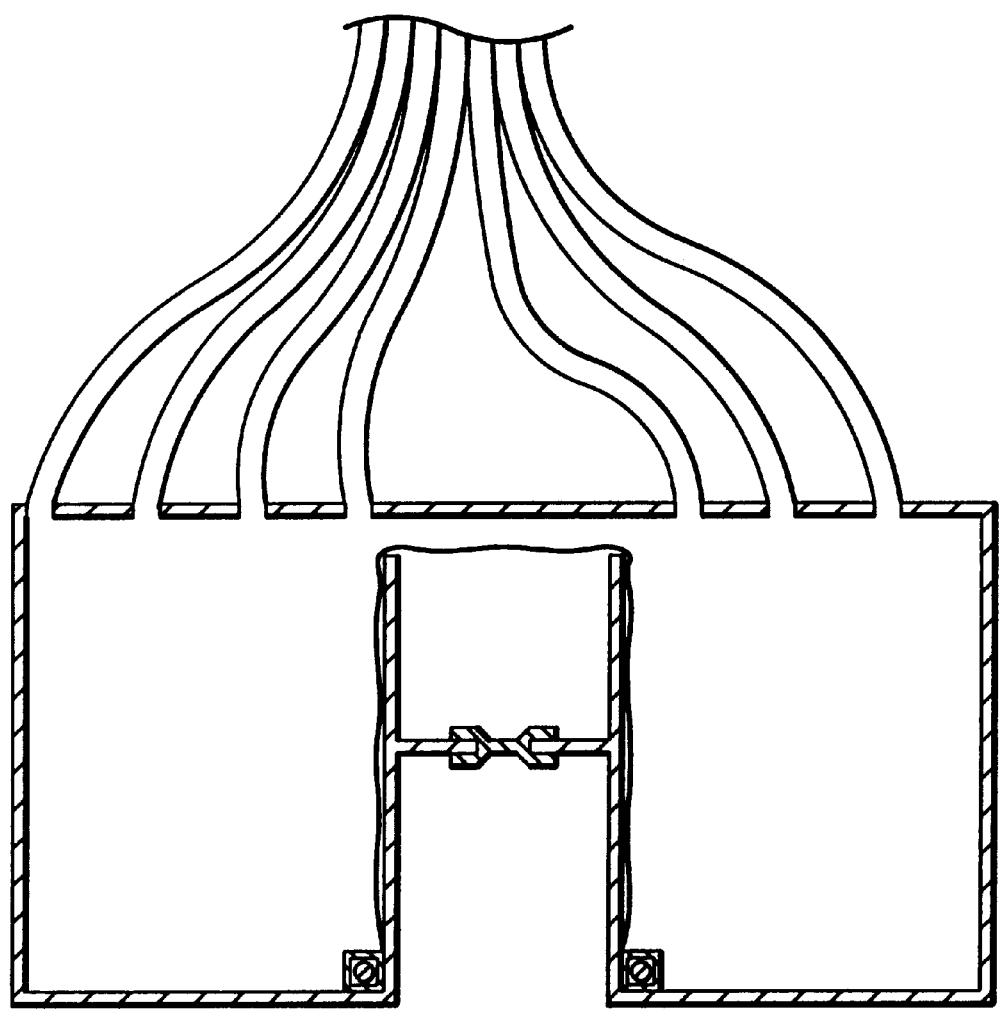
FIG. 31 shows a variation of the rotor shown in FIG. 30, wherein the tubes leading from the processing chamber remain separate.

FIG. 31 shows a rotor similar to the FIG. 30 rotor except that the various tubes connected to the rotor remain separate and attach through a skip-rope system or rotary seal to various parts of the stationary portion of the processing set. These tubes permit the addition of various fluids to the rotor at chosen radii and/or the removal of fluids from chosen points by controls such as pumps or clamps acting on the stationary portion of the processing set.

Figure 32:
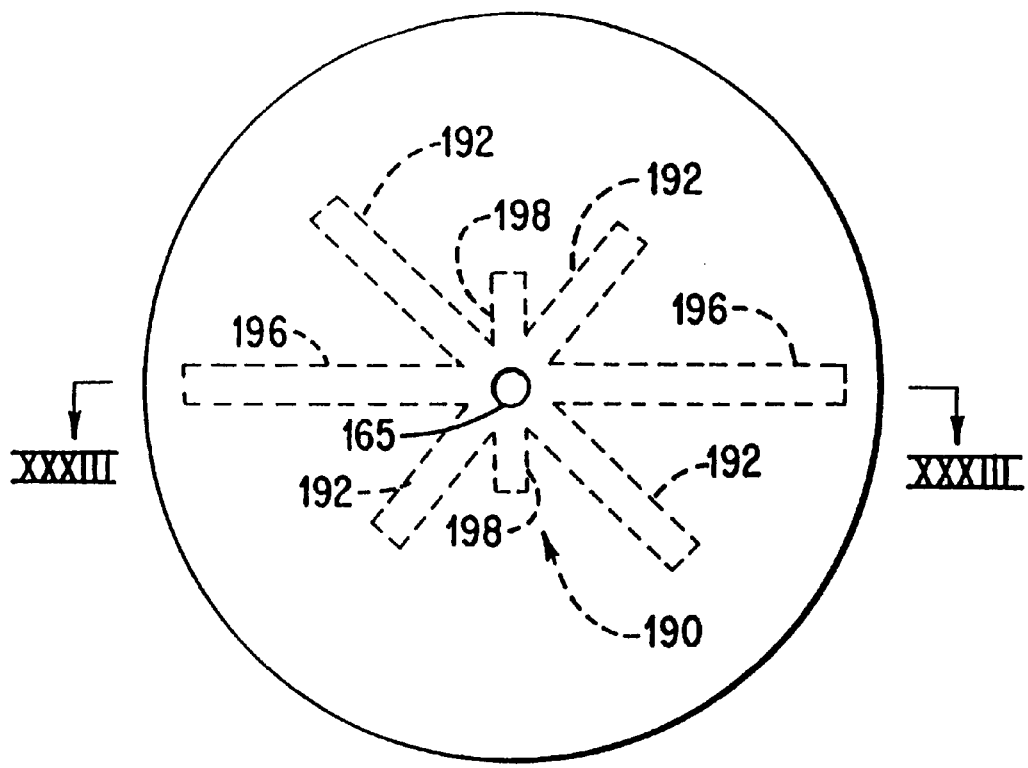
FIG. 32 is a top plan view of a rotor having a set of radially mounted tubes in lieu of a perforate interior wall.
Figure 33:
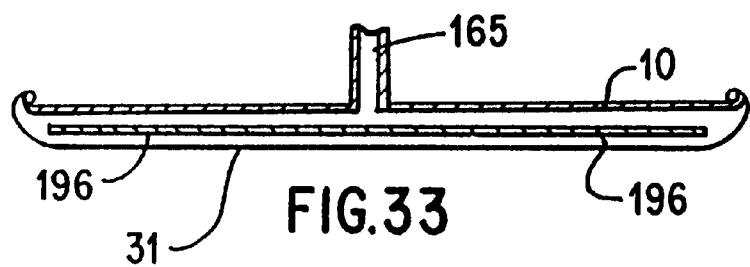
FIG. 33 shows a cross-section of the FIG. 32 rotor.

In an alternative rotor shown in FIGS. 32 and 33, the set of tubes 190 are located within the processing chamber— between the boundary wall 10 and the diaphragm 31. The common outlet tube 165 exits the rotor's top wall 10 at only one location, instead of several locations as shown in FIG. 30. The tubes of the FIG. 32 rotor are oriented radially and may be located adjacent the top wall 10. The tubes may be formed by spot welding a sheet of material that is at least semi-rigid to the bottom of the boundary wall 10. The tubes must be rigid enough to maintain open channels from one end of the tube to the other even when air pressure in the chuck is pressing the diaphragm 31 towards the boundary wall 10. A set of tubes 190 having varying lengths, such as the tubes shown in phantom in FIG. 32, may be used to permit fluid communication between the outlet port 165 and points at various radii in the processing chamber. The set of tubes 190 includes tubes 196 extending substantially to the periphery of the rotor, tubes 198 not extending very far from the rotor's axis of rotation, and tubes 192 of varying intermediate lengths. Of course, more or fewer tubes may be used. In addition, the tubes may include holes to provide the separated fluid elements additional points of exit from the rotor's processing chamber.

In one alternative arrangement, all the tubes extend substantially to the rotor's periphery, and all the tubes have holes in order to provide fluid communication with different points in the rotor's processing chamber. In another alternative embodiment, a single tube having a plurality of holes along its length may be arranged in a spiral extending from the rotor's axis of rotation to its periphery. In all of these embodiments using tubes, the tubes perform the function of the outlet-control plates: they keep open passageways for fluid to flow to and from various points at various radii in the processing chamber. Thus, only tubes 192 of intermediate length may be used to draw fluid components of intermediate density from the rotor's processing chamber (like the plate 40 shown in FIG. 19A), and tubes 196 that extend to the rotor's periphery may be used as an inlet-control structure to introduce unseparated fluid to the periphery of the rotor (like the imperforate plate 87 shown in FIG. 11).

Figure 34:
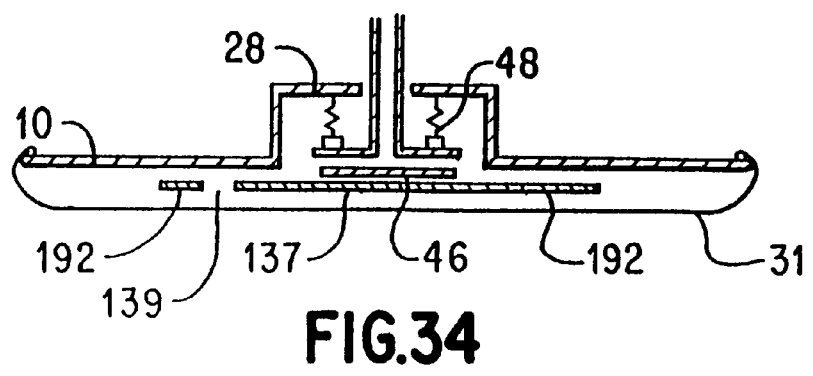
FIG. 34 shows a cross-section of a rotor having a fixed portion and a set of radially mounted tubes in lieu of a perforate interior wall.

FIG. 34 shows a rotor having tubes arranged in a manner similar to the rotor shown in FIGS. 32 and 33. The FIG. 34 rotor has a fixed portion with a collector assembly 46, which is separated from the diaphragm 31 by a small-diameter wall 137, to which all the tubes are attached and which spins with the tubes, the boundary wall 10 and the diaphragm 31. A rotary seal 48 provides the seal between the collector assembly 46 and the collector/rotary-seal area 28 of the boundary wall 10. The rotor's cross-section shown in FIG. 34 shows tubes 192 extending an intermediate distance between the rotor's axis of rotation and the rotor's perimeter. The rotor may also have additional tubes of different lengths. One of the tubes 192 shown in FIG. 34 has a hole 139 to permit flow into the tube 192 from a point closer to the rotor's axis of rotation. Instead of tubes (or an interior plate), grooves may be formed on the bottom of the top wall 10 in order to provide an outlet control means, as shown below in FIGS. 41 and 42.

The FIG. 34 rotor may also be adapted to function like the two-conduit, edge-loading rotor 2b shown in FIG. 11, by adding an imperforate interior wall between the boundary wall 10 and the tubes, and adding a second conduit to the fixed portion. Instead of tubes, radial grooves (like those shown in FIGS. 41 and 42) may be formed on the bottom of the imperforate interior wall. In another alternative embodiment, imperforate tubes extending all the way to the periphery of the processing chamber may be used to introduce unseparated fluid to the edge of the processing chamber, instead of an imperforate interior wall.

Figure 35:
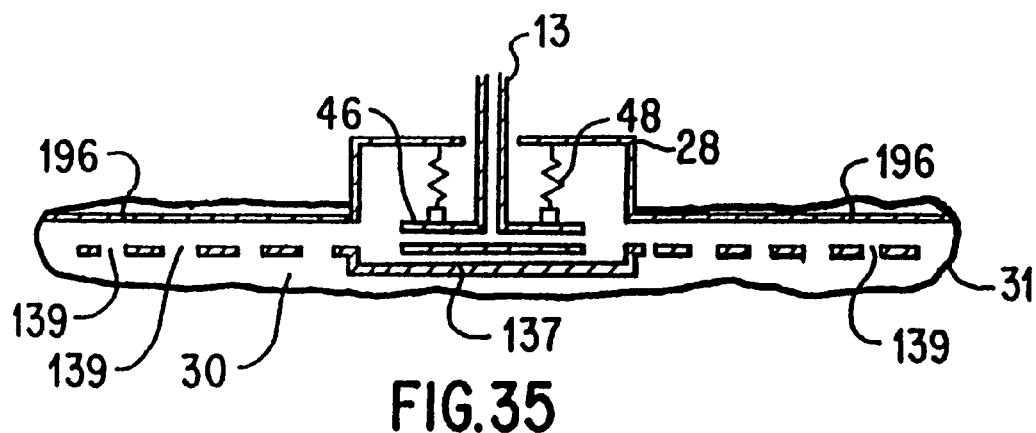
FIGS. 35 and 36 show respectively a cross-section and a top plan view of a rotor having a fixed portion, a set of radially mounted tubes and a diaphragm that covers most of the top of the rotor.
Figure 36:
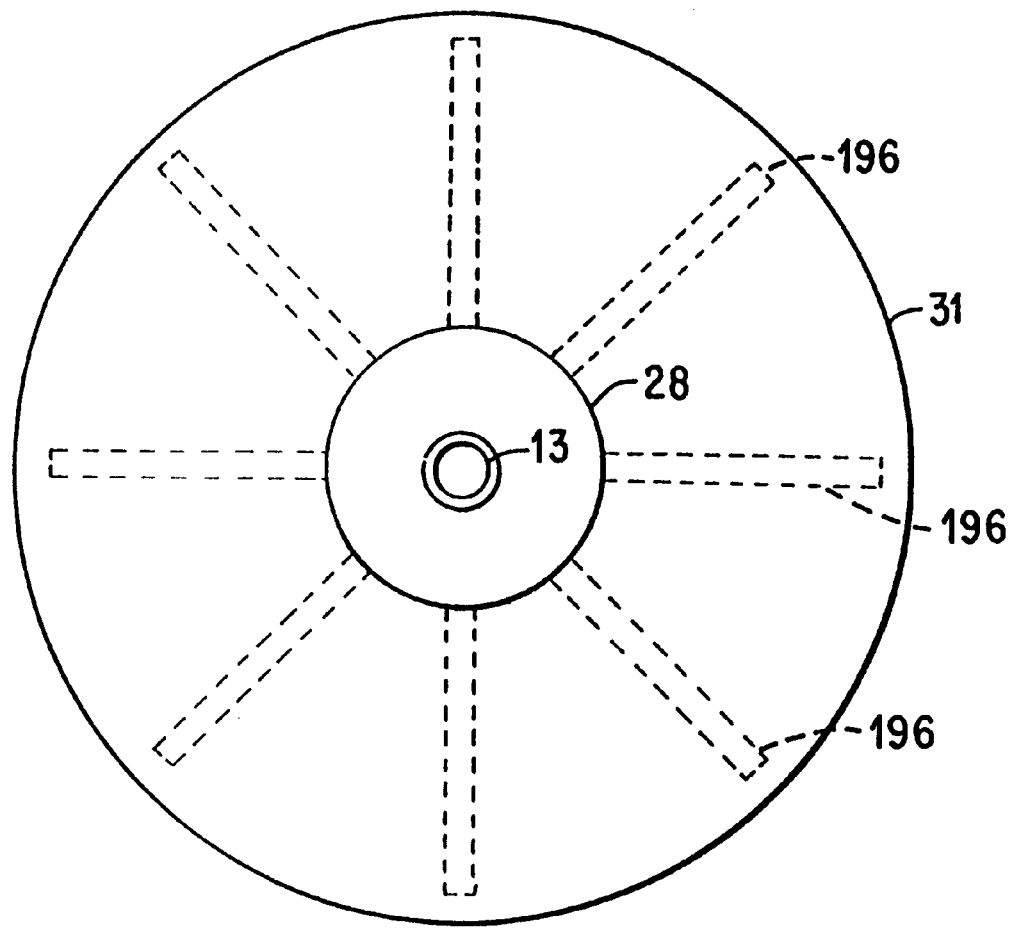

FIGS. 35 and 36 show another alternative rotor. This rotor has a plurality of tubes 196 which extend from a small-diameter wall 137 all the way to the rotor's periphery. The tubes 196 have holes 139 in order to permit flow from the chamber 30 to the collector assembly 46. Instead of having a top wall, this rotor's diaphragm 31 bends around the tubes 196 so as to cover most of the top of the rotor. The rigid rotating portion 28 of the rotor covers the collector assembly 46 and the rotary seal 48. The diaphragm 31 is attached to the circumference of the rigid rotating portion 28. The rigid rotating portion 28 is capable of being held and turned by a chuck so as to cause the diaphragm 31, the tubes 196 and any fluids in the chamber 30 to spin as well. The chuck should also have a lid to cover the top portion of the diaphragm 31 so as to limit how far the diaphragm 31 can expand upwards. The FIG. 35 rotor may also be adapted to function like the two-conduit, edge-loading rotor 2b shown in FIG. 11, by adding a second conduit to the fixed portion, and adding an imperforate interior wall above the tubes 196 or imperforate tubes extending to the periphery of the processing chamber.

It will be appreciated that, during centrifugation in the systems shown in FIGS. 3, 9, 12 and 21, rigid portions of the chuck and/or rotor limit how far the diaphragm 31 can expand outwardly in a radial direction or in an axial direction. For instance, in the system shown in FIG. 3, the chuck 4a limits how far the diaphragm can expand in a radial outward direction and in a downward axial direction. The rotor's rigid boundary wall 10 prevents fluid from flowing upwardly out of the chamber. In the system shown in FIG. 20, the top 108, bottom 112 and circumferential 110 portions of the rotor's boundary wall 10 respectively limit the diaphragm's expansion in the upward and downward axial directions and in the outward radial direction. By limiting the expansion of the diaphragm 31, stresses on the diaphragm during centrifugation may be limited, and better control of the volume of the processing chamber 30 may be maintained.

Figure 37:
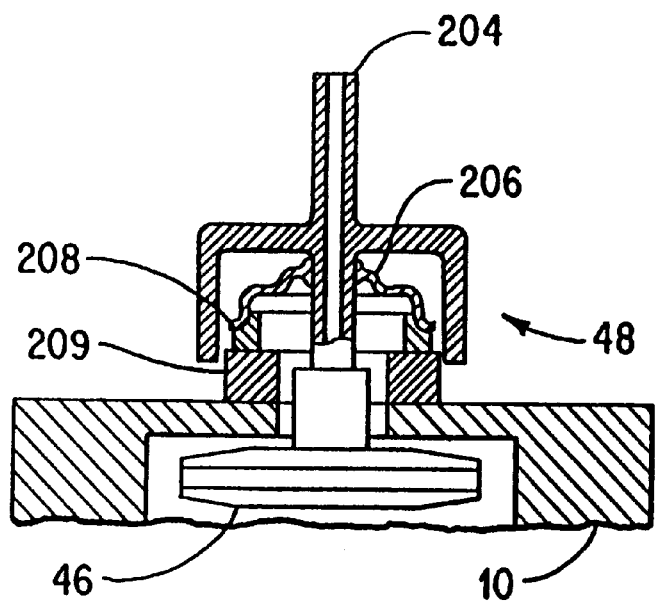
FIG. 37 shows a cross-section of a rotary seal representative of prior-art rotary seals.

The rotors having a fixed portion and a rotatable portion (e.g., the rotors shown in FIGS. 2, 11, 16–18, 19A–19D, 19E, 20, 23, 34 and 35) all have a rotary seal 48. FIG. 37 shows a rotary seal 48 typical of the prior-art rotary seals made by Haemonetics and others. The fixed portion 204 is held in place by a rotor brace (such as item 11 shown in FIGS. 5, 21 and 25) and is thus restrained from vertical, horizontal and rotational movement. While the fixed portion 204 is held in place, the body of the rotor 10, only part of which is shown in FIG. 37, may be spun by a chuck, which restrains the body of the rotor from vertical and horizontal movement while spinning the rotor body. The rotating body 10 of the rotor has rigidly attached and sealed to it an annular rotating seal face 209, which is typically made of ceramic or carbon and is lapped to a very flat surface. The rotating seal face 209 interfaces with an annular non-rotating seal face 208, which is also typically made of ceramic or carbon and lapped to a very flat surface. The non-rotating seal face 208 is held against the rotating seal face 209 by resilient seal member 206. The resilient sealing member 206 is attached and sealed to the fixed portion 204.

This rotary seal 48 is less effective when the pressure inside the rotor becomes greater than the ambient pressure, because the greater inside pressure tends to push up the resilient seal member 206 and thus reduces the force the non-rotating seal face 208 exerts against the rotating seal face 206. The rotors shown hereinabove are subjected to greater internal pressures, especially during the emptying phase, when air pressure in the chuck pushes against the diaphragm in order to force fluid out of the rotor. If the pressure differential becomes large enough, the seal faces 208, 209 will separate momentarily until the internal and external pressures equalize. This momentary separation permits gas to escape from the rotor. Alternately, when a vacuum is created in the interior of the rotor, greater force pushes the seal faces 208, 209 together, thereby creating more heat from friction.

Figure 38:
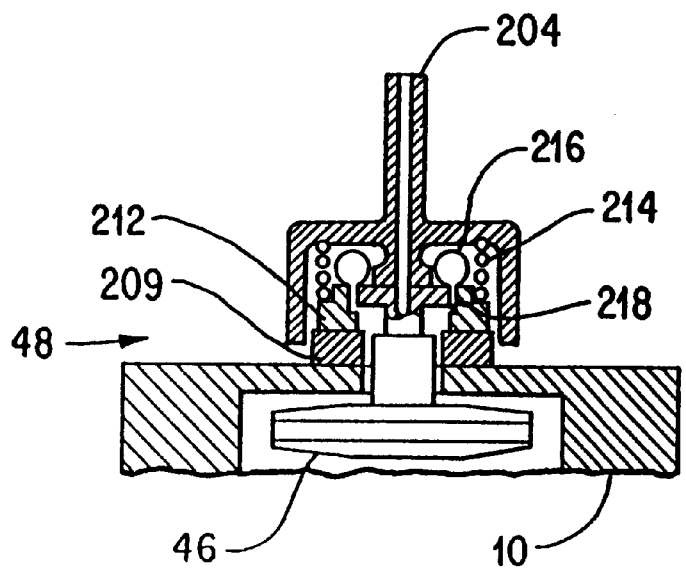
FIG. 38 shows a cross-section of an improved rotary seal, which may be used in the rotors disclosed herein that have fixed and rotating portions.

Although the rotary seal shown in FIG. 37, or another type of rotary seal, may be used in the rotors of the present invention, the improved rotary seal 48 shown in FIG. 38 is preferred. As in the prior-art rotary seal, the fixed portion 204 is held by a brace, preventing vertical, horizontal and rotational movement by the fixed portion 204. The boundary wall 10 of the rotor body is spun by a chuck, which restrains the rotor body from horizontal and vertical movement. The annular rotating seal face 209, preferably made from ceramic or carbon and lapped to a very flat surface is rigidly attached and sealed to the boundary wall 10.

An annular non-rotating seal face 212 is pressed against the rotating seal face 209 by a spring 214, one end of which is attached to the fixed portion 204 and the other end of which is attached to the non-rotating seal face 212. The force applied by this spring 214 is not affected by changes in air pressure within the rotor. The non-rotating seal face 212 can move up and down with respect to the fixed portion 204. The non-rotating seal face 212 is also preferably made of ceramic or carbon and lapped to a very flat surface. A seal is provided between the non-rotating seal face 212 and the fixed portion 204 by flexible seal member 216. The flexible seal member 216 and the spring member 214 are separate members (unlike the prior-art rotary seals). Both seal faces 209, 212, the spring 214 and the flexible seal member 216 surround the rotor's axis of rotation.

It is important that the fixed portion and the rotor body be located an acceptable distance apart, otherwise the spring 214 may not exert the desired amount of force. If the spring is compressed too much (because the fixed portion and the rotor body are too close to each other), the rotary seal may generate excessive heat when the rotor is spun. If the spring is not compressed enough (because the fixed portion and the rotor body are too far from each other), the rotary seal may not exert enough force to keep contaminants from entering the processing chamber between the seal faces 209, 212.

The flexible seal member 216 and the non-rotating seal face 212 may be designed so that any pressure differential between the inside and the outside of the rotor does not affect the force holding the non-rotating seal face 212 against the rotating seal face 209. This may be accomplished by creating opposing surfaces of equal surface area on the flexible seal member 216 and the non-rotating seal face 212, so any effect caused by pressure on one surface is canceled by the effect on the other equal and opposing surface. One way of accomplishing this is to use a flexible seal member 216 with a circular cross-section (as shown in FIG. 38) and to place a small step 218 in the non-rotating seal face 212 (as also shown in FIG. 38) to make up for the small gap in the circular cross-section of the flexible seal member 216. In this design, increases or decreases in pressure act uniformly in all directions and therefore exert no net force. With this design, the seal strength is independent of any pressure differential between the inside and outside of the rotor and is determined solely by the spring constant and the amount of compression of the spring 214.

The rotary seal may be configured so that the spring 214 is connected to and extends from the rotating body of the rotor to the rotating seal face, the flexible seal member 216 connects the rotating body and the rotating seal face, and the non-rotating seal face is rigidly attached to the rotor's fixed portion. Alternatively, two springs and two flexible seal members may be used, so that both seal faces are mounted on springs—one spring being attached to the rotor's fixed portion and the other spring being attached to the rotor's rotating body—and so that a flexible seal member forms a seal between each seal face and its respective portion of the rotor (i.e., the rotating portion or the fixed portion).

Figure 39:
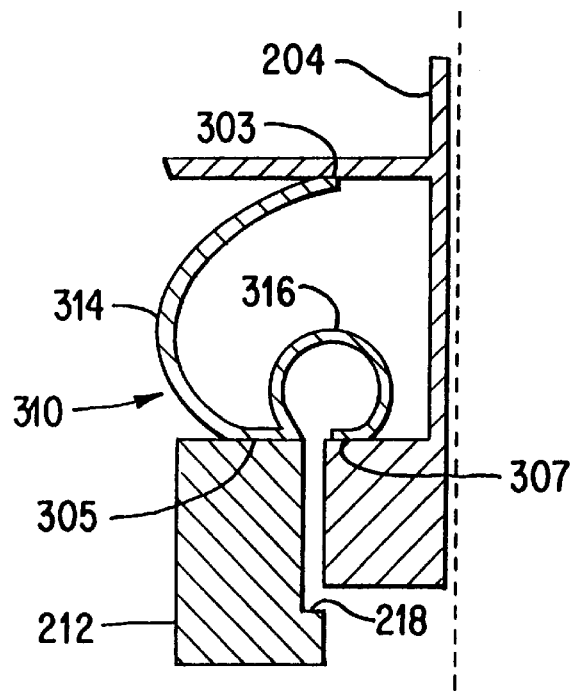
FIG. 39 shows a detail of an alternative rotary seal, wherein the spring and the flexible seal member and the spring are formed out of different portions of the same piece of material.

The rotary seal shown in FIG. 38 may be modified in a number of ways. For instance, as shown in the detail view represented in FIG. 39, the spring 314 and the flexible seal member 316 of the rotary seal may be made out of the same piece of material 310. In addition to manufacturing advantages, such a design has the advantage of providing a spring 314 that applies an even vertical force around the axis of rotation (whereas a coil spring may apply a greater force on some areas of the seal face 212 than on others). One end 303 of the integral spring/seal member 310 is attached to the fixed portion 204 of the rotor. Of course, as noted above with respect to the FIG. 38 rotary seal, the non-rotating seal face 212 can move up and to the fixed pect to the fixed portion 204. The middle 305 of the member 310 is attached and sealed to the seal face 212. The spring portion 314 of the member 310 stretches between these two points of attachment 303, 305. The other end 307 of the member 310 is also attached and sealed to the rotor's fixed portion 204. The flexible-seal-member portion 316 of the member 310 connects the two points of attachment 307 and 305. FIG. 39 also shows the step 218 in the seal face 212 for negating the effects of internal rotor pressure on the force applied to the seal faces.

FIGS. 38 and 39 show the springs 214, 314 located outside of the flexible seal 216, 316, so that the spring is in contact with ambient pressure but is not in direct contact with the rotor air, which air undergoes the rapid pressure variations. The spring may also be located inside the flexible seal. Thus, the spring may be mounted in the region of the step 218, spanning the space between the fixed portion 204 and the non-rotating seal face 212. If the spring is perforated, the changes in internal rotor pressure may pass through the spring to the flexible seal member, so that changes in internal pressure exert no net changes in force between the rotating and non-rotating seal faces 209, 212.

If the flexible seal member 216, 316 is resilient and rigid enough to maintain an adequate seal, it may function as the spring member as well, so that a separate spring member is not required. As long as the components of the rotary seal are shaped properly, changes in internal rotor pressure will exert no net changes in force between the rotating and non-rotating seal faces 209, 212. For example, since the seal portion 316 and the rotating seal face 212 in the rotary seal shown in FIG. 39 have opposing surfaces of equal surface area—so that any effect caused by pressure on one surface is canceled by the effect on the other equal and opposing surface—the separate spring portion 314 may be eliminated without causing the changes in internal rotor pressure to effect the effectiveness of the rotary seal as long as the seal portion 316 is resilient and rigid enough.

Figure 40:
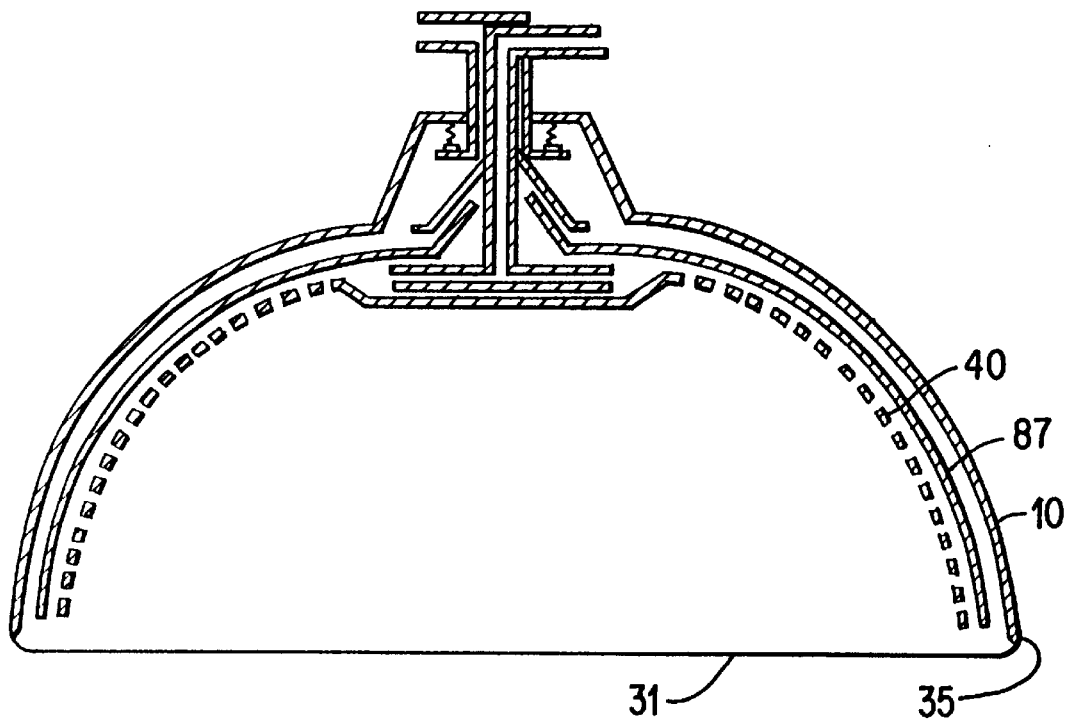
FIG. 40 shows an alternative rotor having a hemispherical boundary wall.

It will be appreciated that the rotors of the present invention can have shapes other than those described hereinabove. For example, FIG. 40 shows a rotor similar in function to the rotor of FIG. 11, but having a generally hemispherical shape.

Figure 41:
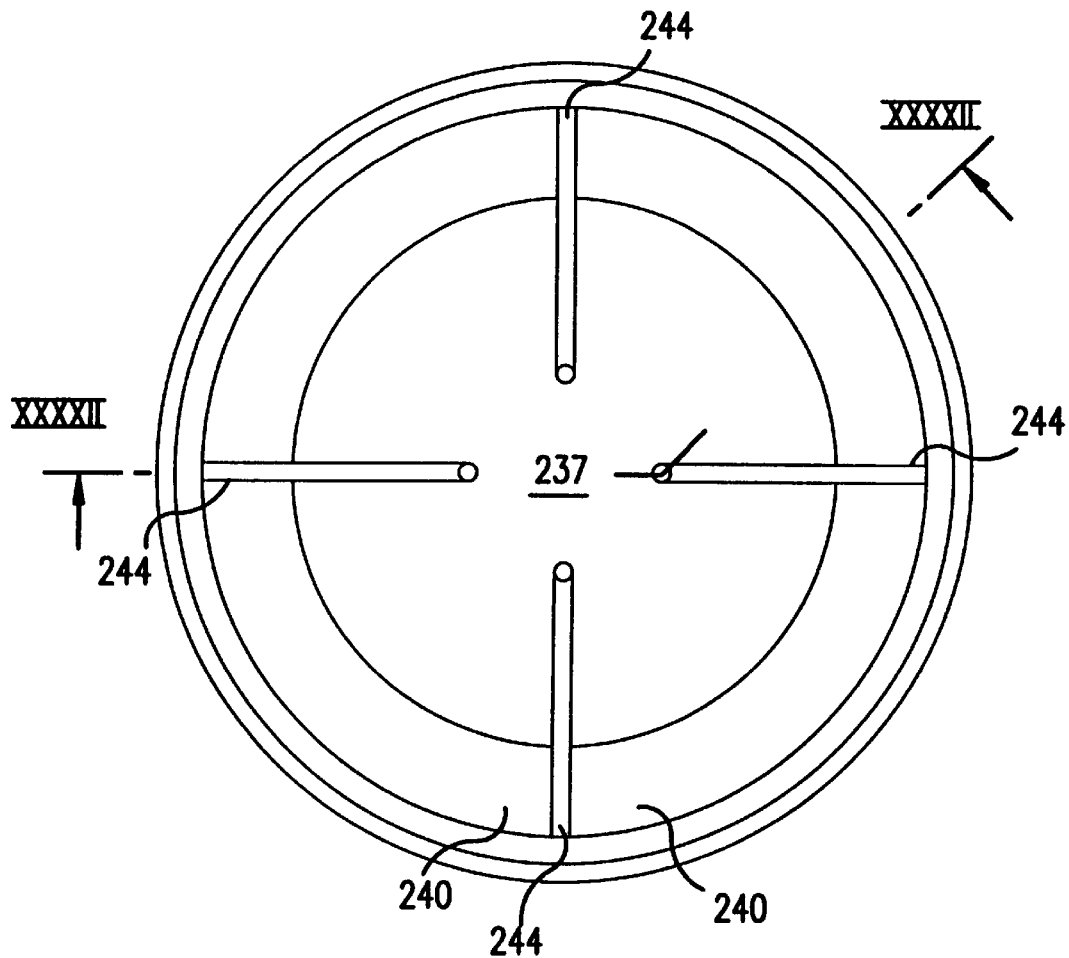
FIG. 41 shows a bottom view of a preferred rotor embodiment without its membrane.
Figure 42:
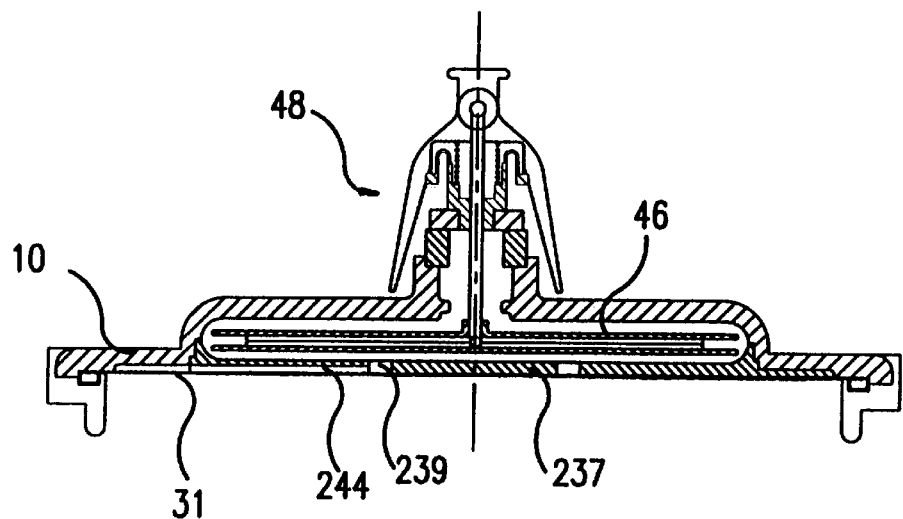
FIG. 42 shows a cross-section of the FIG. 41 rotor with its membrane.

Different types of outlet-control means may be used. For example, FIGS. 41 and 42 show top and cross sectional views of a preferred embodiment of the rotor. This rotor uses grooves 244—preferably radially aligned—formed on the bottom of the top wall 10 as the outlet control means, instead of tubes or an interior perforate wall. The grooves 244 are defined by vertical channel walls 240; if the vertical channel walls 240 are placed close enough to each other, they can keep channels—the grooves 244—open from the holes 239, which connect the processing chamber and the collector assembly 46, to the periphery of the rotor, or to whatever radius it is desired to maintain a channel. The FIG. 42 rotor has a fixed portion (which includes the collector assembly 46 and which interfaces the rotating portion of the rotor at a rotary seal 48), and thus a small-diameter internal wall 237 is necessary to keep the spinning diaphragm 31 from coming into contact with the fixed portion and possibly being abraded.

Although the invention has been described with reference to several preferred embodiments, it will be understood by one of ordinary skill in the art that various modifications can be made without departing from the spirit and the scope of the invention, as set forth in the claims hereinbelow.

What is claimed is:

1. A system for processing blood from a patient's surgery site, the system comprising:
    a rotor having an elastic diaphragm defining a variable-volume chamber;
    means for spinning the rotor around an axis;
    means for changing the pressure of a gas adjacent the rotor's diaphragm, so as to provide a vacuum for drawing fluid into the chamber and so as to provide pressurized gas for forcing fluid out of the chamber;
    a suction tube leading from the surgery site, the suction tube being attached to the rotor, wherein blood drawn from the surgery site through the suction tube may be provided to the rotor; and
    means for directing, after the rotor is spun, lighter blood components to a separate reservoir and returning concentrated red blood cells remaining in the rotor to the patient.

2. A system for separating a fluid having heavier and lighter components, the system comprising:
    a rotor having an elastic diaphragm defining a variable-volume chamber;
    means for spinning the rotor around an axis; and
    means for changing the pressure of a gas adjacent the rotor's diaphragm, so as to provide a vacuum for drawing fluid into the chamber and so as to provide pressurized gas for forcing fluid out of the chamber.

3. The system according to claim 2, wherein the rotor further includes a first conduit for permitting whole blood to flow into the chamber, and a second conduit for permitting separated blood components out of the chamber while whole blood enters the chamber.

4. The system according to claim 2, wherein the pressure against the diaphragm is held constant while the speed the spinning means spins the rotor is reduced, so as to force fluid out of the rotor.

5. The system according to claim 2, wherein the pressure against the diaphragm is increased while the speed the spinning means spins the rotor is reduced, so as to force fluid out of the rotor.

6. The system according to claim 2, wherein the pressure against the diaphragm is increased while the speed the spinning means spins the rotor is kept constant, so as to force fluid out of the rotor.

7. A system for processing blood from a wound drain, the system comprising:
    a rotor having an elastic diaphragm defining a variable-volume chamber;
    means for spinning the rotor around an axis;
    means for changing the pressure of a gas adjacent the rotor's diaphragm, so as to provide a vacuum for drawing fluid into the chamber and so as to provide pressurized gas for forcing fluid out of the chamber;
    a wound drain placed in a patient, the wound drain being attached to the rotor, wherein a vacuum is applied to the diaphragm so as to draw blood from the wound drain into the chamber; and
    means for directing, after the rotor is spun, lighter blood components to a separate reservoir and returning concentrated red blood cells remaining in the rotor to the patient.

8. A system for separating a fluid having heavier and lighter components, the system comprising:
    a rotor having an elastic diaphragm, which defines a chamber, a first conduit for permitting unseparated fluid to flow into the chamber, and a second conduit for permitting separated fluid components to flow out of the chamber while unseparated fluid enters the chamber;
    means for spinning the rotor around an axis; and
    means for changing the pressure of a fluid adjacent the rotor's diaphragm.

9. The system according to claim 8, wherein the pressure-changing means includes means for applying pressurized gas against the diaphragm, so as to force fluid out of the rotor.

10. A system for processing biological fluids of different densities, the system comprising:
    a rotor including
        a variable-volume chamber having an elastic diaphragm defining the chamber,
        a conduit leading from the chamber, and
        outlet-control means for maintaining an open channel to the conduit for fluid at a given radius in the chamber;
    means for holding and spinning the rotor around the axis of rotation so as to separate the fluid into a denser component, a lighter component, and an intermediate-density component;
    means for determining when the intermediate density component is located at the given radius; and means for applying pressure radially outward from the axis of rotation, so as to force the intermediate-density component through the outlet-control means and the conduit.

11. A system for separating fluid into lighter and heavier components, comprising:
 a rotor having an elastic diaphragm defining a variable-volume processing chamber, and having first and second conduits providing fluid communication to the processing chamber;
 means for spinning the rotor; and
 means for introducing the unseparated fluid into the processing chamber through the second conduit while the rotor is being spun and while separated fluid components are forced out of the processing chamber through the first conduit.

12. A system for processing fluids of different densities, the system comprising:
 a rotor including
  a variable-volume chamber having an elastic diaphragm defining the chamber,
  a conduit leading from the chamber, and
  outlet-control means for maintaining an open channel to the conduit for fluid at a given radius in the chamber;
 means for holding and spinning the rotor around the axis of rotation so as to separate the fluid into a denser component and a lighter component; and
 means for forcing one of the denser component and the lighter component from the variable-volume chamber through the outlet-control means to the conduit.

13. The system according to claim 12, wherein the outlet-control means maintains an open channel from the chamber's periphery to the conduit.

14. The system according to claim 12, wherein the outlet-control means includes channel walls, defining a channel from a point in the variable-volume chamber to a point in fluid communication with the conduit, the channel walls being spaced close enough to each other so as to prevent the diaphragm from blocking the channel.

15. The system according to claim 12, wherein the outlet-control means includes a perforate, substantially rigid wall.

16. The system according to claim 12, wherein the outlet-control means includes a set of tubes.

17. The system according to claim 12, wherein the outlet-control means includes at least one tube.

18. A system for processing fluids of different densities, the system comprising:
 a rotor including
  a fixed portion including a conduit assembly,
  an elastic diaphragm rotatably mounted around the fixed portion and the rotor's axis of rotation, the diaphragm defining a chamber of varying volume,
  a rotary seal located around the rotor's axis of rotation, the rotary seal providing a seal between the elastic diaphragm and the fixed portion, and
  an interior wall located between the conduit assembly and the elastic diaphragm;
 means for holding and spinning the rotor around the axis of rotation so as to separate the fluid into a denser component and a lighter component; and
 means for forcing one of the denser component and the lighter component from the chamber to the conduit assembly.

19. In combination,
 a rotor comprised of a rigid wall and an elastic wall defining a first fluid processing chamber therebetween,
 a source of second fluid in fluid communication with the elastic wall for controlling movement of the elastic wall thereby to express or siphon first fluid into or out of said chamber, and
 a mechanism coupled to the rigid wall for rotating the rotor about an axis.

20. A system for separating a fluid having heavier and lighter components, the system comprising:
 a rotor having an elastic diaphragm defining a variable-volume chamber;
 a chuck to which the rotor is mounted to be spun around an axis; and
 a pump which changes the pressure of a gas adjacent the rotor's diaphragm, so as to provide a vacuum for drawing fluid into the chamber and so as to provide pressurized gas for forcing fluid out of the chamber.

21. The system according to claim 20, wherein the rotor further includes a first conduit for permitting whole blood to flow into the chamber, and a second conduit for permitting separated blood components out of the chamber while whole blood enters the chamber.

22. A system for processing blood from a wound drain, the system comprising:
 a rotor having an elastic diaphragm defining a variable-volume chamber;
 a chuck to which the rotor is mounted to be spun around an axis;
 a wound drain placed in a patient, the wound drain being attached to the rotor, wherein a vacuum is applied to the diaphragm so as to draw blood from the wound drain into the chamber; and
 a valving mechanism for directing lighter blood components to a separate reservoir and returning concentrated red blood cells remaining in the rotor to the patient.

23. A system for processing blood from a patient's surgery site, the system comprising:
 a rotor having an elastic diaphragm defining a variable-volume chamber;
 a chuck to which the rotor is mounted to be spun around an axis;
 a pump that changes the pressure of a gas adjacent the rotor's diaphragm, so as to provide a vacuum for drawing fluid into the chamber and so as to provide pressurized gas for forcing fluid out of the chamber;
 a suction tube leading from the surgery site, the suction tube being attached to the rotor, wherein blood drawn from the surgery site through the suction tube may be provided to the rotor; and
 a valving mechanism for directing lighter blood components to a separate reservoir and returning concentrated red blood cells remaining in the rotor to the patient.

24. A system for separating a fluid having heavier and lighter components, the system comprising:
 a rotor having an elastic diaphragm, which defines a chamber, a first conduit for permitting unseparated fluid to flow into the chamber, and a second conduit for permitting separated fluid components to flow out of the chamber while unseparated fluid enters the chamber;
 a chuck to which the rotor is mounted to be spun around an axis; and
 a pump that changes the pressure of a fluid adjacent the rotor's diaphragm.

25. A system for processing fluids of different densities, the system comprising:
- a rotor including
  - a variable-volume chamber having an elastic diaphragm defining the chamber,
  - a conduit leading from the chamber, and
  - an open channel extending from the conduit to permit fluid at a given radius in the chamber to flow to the conduit;
- a chuck in which the rotor is mounted to be spun around an axis of rotation so as to separate the fluid into a denser component and a lighter component; and
- a pump that forces one of the denser component and the lighter component from the variable-volume chamber through the open channel to the conduit.

26. The system according to claim 25, wherein the open channel extends from the chamber's periphery to the conduit.

27. The system according to claim 26, wherein the open channel is defined by channel walls extending from a point in the variable-volume chamber near the periphery to a point in fluid communication with the conduit, the channel walls being spaced close enough to each other so as to prevent the diaphragm from blocking the channel.

28. A system for processing fluids of different densities, the system comprising:
- a rotor including
  - a fixed portion including a conduit assembly,
  - an elastic diaphragm rotatably mounted around the fixed portion and the rotor's axis of rotation, the diaphragm defining a chamber of varying volume,
  - a rotary seal located around the rotor's axis of rotation, the rotary seal providing a seal between the elastic diaphragm and the fixed portion, and
  - an interior wall located between the conduit assembly and the elastic diaphragm;
- a chuck to which the rotor is mounted to be spun around the axis of rotation so as to separate the fluid into a denser component and a lighter component; and
- a pump for forcing one of the denser component and the lighter component from the chamber to the conduit assembly.

29. A system for separating fluid into lighter and heavier components, the system comprising:
- a rotor having an elastic diaphragm that defines a variable-volume processing chamber for as receiving unseparated fluid; and
- a motor for spinning the rotor, so as to cause the fluid to separate into lighter and heavier components.

30. A system for separating fluid into lighter and heavier components, the system comprising:
- a rotor having an elastic diaphragm that defines a variable-volume processing chamber;
- a stationary inlet for introducing unseparated fluid into the processing chamber; and
- a motor for spinning the rotor, so as to cause the fluid to separate into lighter and heavier components.

31. A system according to claim 30 wherein the elastic diaphragm extends across a diameter of the rotor.

32. A system according to claim 30 wherein the rotor has a rim and the elastic diaphragm is attached around the rim.

33. The system according to claim 30, further comprising:
A pump for applying pressure to the diaphragm so as to force A fluid component out of the chamber.

34. The system according to claim 30, further comprising:
A pump for applying a vacuum to the diaphragm so as to force the fluid into the chamber.

35. A system for processing biological fluids of different densities, the system comprising:
- A rotor having a rigid mounting member and an elastic diaphragm attached to the mounting member, the diaphragm extending across a diameter of the rotor and defining a variable-volume processing chamber;
- A stationary inlet rotationally coupled to the rigid mounting member for introducing an unseparated fluid into the chamber;
- A motor coupled to the rotor by the rigid mounting member for spinning the rotor around an axis so as to separate the fluid into denser and lighter components, the denser component congregating away from the axis while the lighter component congregates closer to the axis.

36. A system for processing biological fluids of different densities, the system comprising the steps of:
- A rotor having a rigid mounting member, a rim, and an elastic diaphragm attached around the rim, the diaphragm defining a variable-volume processing chamber;
- A stationary inlet rotationally coupled to the rigid member for introducing an unseparated fluid into the chamber;
- A motor coupled to the rotor by the rigid mounting member for spinning the rotor around an axis so as to separate the fluid into denser and lighter components, the denser component congregating away from the axis while the lighter component congregates closer to the axis.

37. A system for separating fluid into lighter and heavier components, the system comprising:
- A rotor having an elastic diaphragm that defines a variable-volume processing chamber;
- A motor for rotating the rotor around an axis;
- means for drawing unseparated fluid into the variable-volume processing chamber through centrifugal force allowing the fluid to separate into lighter and heavier components.

38. The system according to claim 37, wherein the rotor further comprises:
A non-spinning fluid inlet.

39. The system according to claim 37, wherein the rotor further comprises:
A pump for applying a vacuum to the diaphragm so as to force the fluid into the chamber.

40. A rotor for use with a system for separating fluid into lighter and heavier components, the rotor comprising:
A rigid support member having a fluid inlet; and
an elastic diaphragm that defines a variable-volume processing chamber coupled to the rigid support member; wherein the rotor is spun about an axis, so as to cause the fluid to separate into lighter and heavier components.

* * * * *

UNITED STATES PATENT AND TRADEMARK OFFICE
CERTIFICATE OF CORRECTION

PATENT NO. : 6,099,491
DATED : August 8, 2000
INVENTOR(S) : Thomas D. Headley et al.

It is certified that error appears in the above-identified patent and that said Letters Patent is hereby corrected as shown below:

Claims
32. A system according to claim 30 wherein the rotor has [A] a rim and the elastic diaphragm is attached around the rim 33. The system according to claim 30, further comprising:
[A] a pump for applying pressure to the diaphragm so as to force [A] a fluid component out of the chamber.

34. The system according to claim 30, further comprising:
[A] a pump for applying [A] a vaccuum to the diaphragm so as to force the fluid into the chamber.

35. A system for processing biological fluids of different densities, the system comprising:
[A] a rotor having [A] a rigid mounting member and an elastic diaphragm attached to the mounting member, the diaphragm extending across [A] a diameter of the rotor and defining [A] a variable-volume processing chamber;

[A] a stationary inlet rotationally coupled to the rigid mounting member for introducing an unseparated fluid into the chamber;

[A] a motor coupled to the rotor by the rigid mounting member for spinning the rotor around an axis so as to separate the fluid into denser and lighter components, the denser component congregating away form the axis while the lighter component congregates closer to the axis.

36. A system for processing biological fluids of different densities, the system comprising the steps of:

[A] a rotor having [A] a rigid mounting member, [A] a rim, and an elastic diaphragm attached around the rim, the diaphragm defining [A] a variable-volume processing chamber;

[A] a stationary inlet rotationally coupled to the rigid member for introducing an unseparated fluid into the chamber;

[A] a motor coupled to the rotor by the rigid mounting member for spinning the rotor around an axis so as to separate the fluid into denser and lighter components, the denser component congregating away from the axis while the lighter component congregates closer to the axis.

UNITED STATES PATENT AND TRADEMARK OFFICE
CERTIFICATE OF CORRECTION

PATENT NO. : 6,099,491  
DATED : August 8, 2000  
INVENTOR(S) : Thomas D. Headley et al.

Page 2 of 2

It is certified that error appears in the above-identified patent and that said Letters Patent is hereby corrected as shown below:

37. A system for separating fluid into lighter and heavier components, the system comprising:

[A] a rotor having an elastic diaphragm that defines [A] a variable-volume processing chamber;
[A] a motor for ratating the rotor around the axis;
means for drawing unseparated fluid into the variable-volume processing chamber through centrifugal force allowing the fluid to separate into lighter and heavier components.

38, The system according to claim 37, wherein the rotor further comprises:
[A] a non-spinning fluid inlet.

39. The system according to claim 37, wherein the rotor further comprises:
[A] a pump for applying [A] a vacuum to the diaphragm soas to force the fluid into the chamber.

40. A rotor for use with [A] a system for separating fluid into lighter and heavier components, the rotor comprising"
[A] a rigid support member having [A] a fluid inlet; and
an elastic diaphragm that defines [A] a variable-volume processing chamber coupled to the rigid support member;
wherein the rotor is spun about an axis, so as to cause the fluid to separate into lighter and heavier components.

Signed and Sealed this

Twenty-Seventh of November, 2001

*Attest:*

NICHOLAS P. GODICI

*Attesting Officer*    *Acting Director of the United States Patent and Trademark Office*